United States Patent
Biedermann et al.

(10) Patent No.: US 6,451,816 B1
(45) Date of Patent: *Sep. 17, 2002

(54) USE OF PYRIDYL ALKANE, PYRIDYL ALKENE AND/OR PYRIDYL ALKINE ACID AMIDES IN THE TREATMENT OF TUMORS OR FOR IMMUNOSUPPRESSION

(75) Inventors: Elfi Biedermann, Vaterstetten; Max Hasmann, Neuried; Roland Löser, Feldafing; Benno Rattel, Munich; Friedemann Reiter, Putzbrunn; Barbara Schein, Neufahrn; Klaus Seibel, Gräfelfing; Klaus Vogt, Munich, all of (DE)

(73) Assignee: Klinge Pharma GmbH, Munich (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/216,482

(22) Filed: Dec. 18, 1998

Related U.S. Application Data

(63) Continuation of application No. PCT/EP97/03244, filed on Jun. 20, 1997.

(51) Int. Cl.[7] .................... A61K 31/444; C07D 401/08; C07D 40/12
(52) U.S. Cl. .................... 514/318; 514/317; 546/196; 546/197; 546/198; 546/207; 546/208
(58) Field of Search ................ 546/193, 196, 546/197, 198, 207, 208; 514/211, 212, 222.2, 215, 222.8, 247, 317, 318

(56) References Cited

U.S. PATENT DOCUMENTS

| | | | | |
|---|---|---|---|---|
| 4,283,541 A | | 8/1981 | Shroff et al. | 546/336 |
| 5,169,856 A | * | 12/1992 | Goto et al. | 514/331 |
| 5,260,323 A | | 11/1993 | Baader et al. | 514/356 |
| 5,326,772 A | | 7/1994 | Klemm et al. | 514/318 |

FOREIGN PATENT DOCUMENTS

| | | | |
|---|---|---|---|
| CA | 2085954 | 6/1993 | |
| DE | 40 20 570 A1 | 1/1992 | C07D/213/89 |
| EP | 048045 | 3/1982 | |
| EP | 0 210 782 A2 | 2/1987 | C07D/213/56 |
| EP | 271023 | 6/1988 | |
| EP | 0 330 026 B1 | 2/1989 | |
| EP | 0 330 026 A1 | 2/1989 | C07D/211/26 |
| EP | 0 343 307 A1 | 11/1989 | C07D/211/58 |
| EP | 416581 | 3/1991 | |
| EP | 471236 | 2/1992 | |
| EP | 479601 | 4/1992 | |
| EP | 522606 | 1/1993 | |
| EP | 0 530 444 A1 | 3/1993 | C07D/213/82 |
| EP | 0 548 883 A1 | 6/1993 | C07D/213/89 |
| EP | 512902 | 4/1994 | |
| EP | 428434 | 5/1994 | |
| GB | 2304714 | 11/1998 | |
| JP | 57136518 | 8/1982 | |
| JP | 63179869 | 7/1988 | |
| WO | WO89/07443 | 8/1989 | |
| WO | WO 91/15484 A1 | 10/1991 | C07D/401/06 |
| WO | WO 91/15485 A1 | 10/1991 | C07D/401/12 |
| WO | 9313083 | * 7/1993 | |
| WO | WO93/14113 | 7/1993 | |
| WO | WO 95/10514 A1 | 4/1995 | C07D/401/04 |
| WO | WO95/10515 | 4/1995 | |
| WO | WO95/10516 | 4/1995 | |
| WO | WO95/24894 | 9/1995 | |
| WO | WO93/14070 | 3/1996 | |
| WO | WO96/31478 | 10/1996 | |
| WO | WO94/01402 | 3/1997 | |
| WO | WO97/48397 | 12/1997 | |
| WO | WO96/31477 | 1/1998 | |
| WO | WO97/48695 | 1/1998 | |

OTHER PUBLICATIONS

Nishikawa et al., Acrylamide Derivatives as Antiallergic Agents. 2. Synthesis and Structure–Activity Relationships of N–[4–[4–. (Diphenymethyl) –1–piperaziny1]butyl] 3–(3–pyridyl) acrylamides J. Med. Chem. 1989, 32, 583–593.
Ishihara et al., "Central Cholinergic Agents. II. Synthesis and Acetylcholinesterase Inhibitory Activities of N–[w–[N–Alkyl–N–(phenylmethyl) amino] alkyl] –3–arylprope-namides" Chem. Pharm. Bull. 39 (12) 3236–3234 (1991).
Rote Liste. 1997, (2 pages).
Chemical Abstracts, 15–Immunochemistry. vol. 124, No. 13, 1996, (1 page).
Chemical Abstracts. vol. 115, 1991, (1 page).
Nishikawa et al., "Acrylamide Derivatives as Antiallergic Agents." Chem. Pharm. Bull. 37, No. 1, 1989, (6 pages).
W. C. J. Ross. "The Preparation of Some 4–Substituted Nicotinic Acids and Nicotinamides." J. Chem. Soc. 1966, (6 pages).
R. Fischer, "Allgemeine Pathologie und Pathologische Anatomie." Published before filing date, (7 pages).

* cited by examiner

*Primary Examiner*—Alan L. Rotman
*Assistant Examiner*—Rita Desai
(74) *Attorney, Agent, or Firm*—Fitch, Even, Tabin, & Flannery

(57) ABSTRACT

The invention relates to the use of pharmacologically valuable pyridyl alkane, pyridyl alkene and/or pyridyl alkine acid amides according to general formula (I) in the treatment of tumors or for immunosuppression.

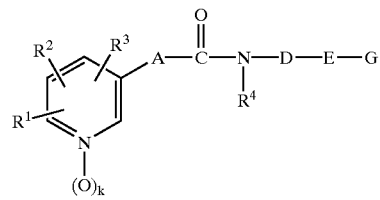

18 Claims, No Drawings

USE OF PYRIDYL ALKANE, PYRIDYL ALKENE AND/OR PYRIDYL ALKINE ACID AMIDES IN THE TREATMENT OF TUMORS OR FOR IMMUNOSUPPRESSION

This application is a continuation of PCT/EP97/03244, filed Jun. 20, 1997.

The invention relates to the use of pyridyl aklane, pyridyl alkene and/or pyridyl alkine acid amides, especially in the treatment of tumor conditions and/or as cytostatic agents or as immunosuppressive agents as well as medicaments with an amount of these compounds in combination with other cytostatic agents or immunosuppresive agents.

A strong need exists for the enrichment of cytostatic therapy to provide pharmaceuticals and/or medicaments which not only possess a strong activity, but also exert diminished side effects in comparison to many classical cancerostatic agents, whereby treatment of a broad as possible spectrum of tumors should be made accessible. Furthermore, effective cytostatic agents for an efficient therapy should be made available. Active ingredients of this type should also be exceptionally suitable in the mentioned indications for a combination therapy, be it in connection with other cytostatic agents or with radiation (for example X-rays, radioactive elements, such as cobalt, or linear accelerator. etc.), with operative procedures, heat treatment, etc. As a consequence, further subject-matter of the invention relates to new medicaments in the form of combinations of the compounds defined below and used according to the invention together with other compounds or immunosuppressive agents customary in the therapy of tumors.

In this connection, a strong need also exists in tumor therapy to open up new possibilities which were not usable up to now in these indications, for example for overcoming or preventing resistances.

This object was successfully solved in a completely suprising manner by making available the specially structured pyridyl derivatives defined below.

It was known that various pyridine compounds substituted in a specific manner have pharmacologically useful properties which lie however in completely different indication areas.

Thus, ω-pyridyl alkane and/or alkene amides with anti-allergic activity are described in EP 0 210 782 which are referred to as having a 5-lipoxygenase-inhibiting and anti-histamine action, wherein the amide components of these compounds contain a piperizine or homopiperizine ring and the pyridine ring can be linked together in the 2-, 3- or 4-position. JP 63,179,869 describes further pyridyl amides, ω-pyridyl alkane and alkene amides as anti-allergic effective substances containing a substituted piperidine ring in the amine component. Such compounds with the same properties are mentioned in Chem. Pharm. Bull 37, 100–105 (1989) and in J. Med. Chem. 1989, 583–593.

Pyridyl ureas, pyridyl thioureas and pyridyl carbonamides, wherein the amide portion is bound over an aryl substituted alkyl chain with a piperidine ring or piprazine ring, are described for example in EP-A-0 428 434 or in EP-A-0 512 902 as antagonists of the neurokinin receptor and substance P. Furthermore, the pyridyl(alkyl)carbonamides, pyridyl(alkyl)sulfonamides and analogous ureas, wherein the amide portion is bound over an alkyl chain with a piperidine ring are disclosed in EP-A-0 479 601 as active ingredients with anti-arrhythmic properties.

In WO 91/15 485, the production of pyridine-3,5-dicarboxylic acid esters and amides as well as their use for the treatment of tumor conditions is described. These compounds differ from the compounds according to the invention described below in very important structural features, for example by the dicarboxyl grouping on the pyridine ring or the absence of the hydrocarbon chain between the pyridine ring and the amide grouping. The compounds disclosed in WO 89/07 443 in the form of optically pure R(-)-Niguldipine and further analogous dihydropyridines with cytotoxic activity have larger structural differences. However, the compounds according to the invention unexpectedly possess a better activity and a wider spectrum of action despite the large structural differences.

Further structurally closely related compounds are represented by the antagonists of the histimine-$H_1$-receptor described in EP-A-0 343 307 which discloses a series of substituted piperidine derivatives without naming concrete examples for special 3-pyridyl substitutions.

EP-A-0 330 026 also discloses substituted piperidine derivatives with possible, generic pyridyl substitutions for which, however, merely a single concrete example is disclosed, namely (E)-3-(3-pyridyl)-N-[2-(1-benzylpiperidin-4-yl)ethyl]-2-propenamide hydrochloride. These compounds are distinguished by an anti-cholinesterase activity, an anti-amnesia activity as well as activities directed against hyperkinesia, senile demensia, mania and Alzheimer's disease.

In view of this art, the finding that the compounds according to the general formula (I) defined below have activities which make them particularly suitable in an excellent manner for the therapy of tumor illnesses was completely unexpected. Equally unexpected was the pharmacological finding that the compounds according to the invention also possess immunosuppressive properties besides cytostatic activity.

Considering the above-mentioned completely different known medical indications of known piperidine derivatives, such as neurokinin receptor antagonism, hyperkineses, amnesias, allergies, or rhythm disorders, the activity of the compounds used according to the invention with the structural modifications as they are defined below with respect to the present general formula, and the combinations according to the invention in the form of the detected excellent cytostatic or immunomodulatory activity with advantageous therapeutic properties was completely surprising for the person skilled in the art.

Pharmacological test results from which this conclusion must be drawn, as well as the concrete tumor indications and combination possibilities are detailed and illustrated in the last part of the description.

Therefore, subject-matter of the invention relates to the use of one or more compounds of formula (I)

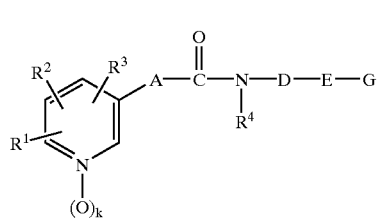

wherein
$R^1$ is hydrogen, halogen, cyano, trifluoromethyl, hydroxy, benzyloxy, aminocarbonyl, carboxy, phenyl, phenoxy, phenylthio, pyridyloxy, pyridylthio, alkyl, especially $C_1$–$C_6$-alkyl, alkenyl, especially $C_3$–$C_6$-alkenyl, alkinyl, especially $C_3$–$C_6$-alkinyl, hydroxyalkyl, especially $C_1$–$C_6$-hydroxyalkyl, alkoxy, especially $C_1$–$C_6$- alkoxy, alkenyloxy, especially $C_3$–$C_6$-alkenyloxy, alkinyloxy, especially $C_3$–$C_6$-alkinyloxy, alkanoyloxy, especially $C_1$–$C_7$-alkanoyloxy, alkoxycarbonyloxy, especially $C_2$–$C_7$-alkoxycarbonyloxy, alkylthio, especially $C_1$–$C_6$-alkylthio, alkenylthio, especially $C_3$–$C_6$-alkenylthio, alkinylthio, especially $C_3$–$C_6$-alkinylthio, cycloalkyl, especially $C_3$–$C_8$-cycloalkyl, cycloalkyloxy, especially $C_3$–$C_8$-cycloalkyloxy, cycloalkylthio, especially $C_3$–$C_8$-cycloalkylthio, alkoxycarbonyl, especially $C_2$–$C_7$-alkoxycarbonyl, alkylaminocarbonyl, especially $C_2$–$C_7$-alkylaminocarbonyl, dialkylaminocarbonyl, especially $C_3$–$C_{13}$-dialkylaminocarbonyl, or $NR^5R^6$, wherein $R^5$ and $R^6$ are selected independently of each other from hydrogen, alkyl, especially $C_1$–$C_6$-alkyl, alkenyl, especially $C_3$–$C_6$-alkenyl and alkinyl, especially $C_3$–$C_6$-alkinyl, $R^2$ is hydrogen, halogen, cyano, hydroxy, trifluoromethyl, benzyloxy, alkyl, especially $C_1$–$C_6$-alkyl, alkoxy, especially $C_1$–$C_6$-alkoxy or alkanoyloxy, especially $C_1$–$C_7$-alkanoyloxy, wherein $R^1$ and $R^2$, if they are adjacent, optionally form a bridge which is selected from —$(CH_2)_4$—, —$(CH=CH)_2$— and —$CH_2O$—$CR^7R^8$—$O$—, wherein $R^7$ and $R^8$ are, independently of each other, hydrogen or alkyl, especially $C_1$–$C_6$-alkyl, $R^3$ is hydrogen, halogen, alkyl, especially $C_1$–$C_6$-alkyl, trifluoromethyl or hydroxyalkyl, especially $C_1$–$C_6$-hydroxyalkyl and $R^4$ is hydrogen, hydroxy, benzyloxy, alkyl, especially $C_1$–$C_6$-alkyl, alkenyl, especially $C_3$–$C_6$-alkenyl, alkinyl, especially $C_3$–$C_6$-alkinyl, cycloalkyl, especially $C_3$–$C_6$-cycloalkyl or alkoxy, especially $C_1$–$C_6$-alkoxy, k is 0 or 1, A is alkylene, especially $C_1$–$C_6$-alkylene, which is optionally substituted once to three-fold by alkyl, especially $C_1$–$C_3$-alkyl, hydroxy, alkoxy, especially $C_1$–$C_3$-alkoxy, fluorine or phenyl, or 1,2-cyclopropylene or alkenylene with at least two C-atoms, especially $C_2$–$C_6$-alkenylene, which is optionally substituted once to three-fold by $C_1$–$C_3$-alkyl, hydroxy, $C_1$–$C_3$-alkoxy, fluorine, cyano or phenyl, alkadienylene with at least four C-atoms, especially $C_4$–$C_6$-alkadienylene, which is optionally substituted once or twice by $C_1$–$C_3$-alkyl, fluorine, cyano or phenyl, 1,3,5-hexatrienylene, which is optionally substutited by $C_1$–$C_3$-alkyl, fluorine, cyano, or phenyl, ethinylene or alkylene with at least two C-atoms, especially $C_2$–$C_6$-alkylene in which a methylene unit can be isosterically replaced by O, S, $NR^9$, CO, SO or $SO_2$, wherein the isosteric substitution, with the exception of =CO, cannot be adjacent to the amide group and wherein $R^9$ is selected from hydrogen, alkyl, especially $C_1$–$C_6$-alkyl, alkenyl, especially $C_3$–$C_6$-alkenyl, alkinyl, especially $C_3$–$C_6$-alkinyl, acyl, especially $C_1$–$C_6$-acyl or alkylsulfonyl, especially $C_1$–$C_6$-alkylsulfonyl, D is selected from alkylene, especially $C_1$–$C_{10}$-alkylene, optionally substituted once or twice by alkyl, especially $C_1$–$C_6$-alkyl, hydroxy, or alkoxy, especially $C_1$–$C_6$-alkoxy, alkenylene with at least two C-atoms, especially $C_2$–$C_{10}$-alkenylene, which is optionally substituted once or twice by alkyl, especially $C_1$–$C_6$-alkyl, hydroxy, or alkoxy, especially $C_1$–$C_6$-alkoxy, wherein the double bond can also be to ring E, alkinylene with at least three C-atoms, especially $C_3$–$C_{10}$-alkinylene, optionally substituted once or twice by alkyl, especially $C_1$–$C_6$-alkyl, hydroxy or alkoxy, especially $C_1$–$C_6$-alkoxy, and alkylene, especially $C_1$–$C_{10}$-alkylene, alkenylene with at least two C-atoms, especially $C_2$–$C_{10}$-alkenylene or alkinylene with at least three C-atoms, especially $C_3$–$C_{10}$-alkinylene, whereby one to three methylene units are each isosterically replaced by O, S, $NR^{10}$, CO, SO or $SO_2$ wherein $R^{10}$ has the same meaning as $R^9$ but is selected independently thereof, E is selected from

 (E1)

or

 (E2)

wherein the heterocyclic ring can also optionally have a double bond and n and p can be, independently of one another, 0, 1, 2 or 3, with the proviso that n+p≦4 and q is 2 or 3, $R^{11}$ is hydrogen, alkyl, especially $C_1$–$C_6$-alkyl, hydroxy, hydroxymethyl, carboxy or alkoxycarbonyl with at least two C-atoms, especially $C_2$–$C_7$-alkoxycarbonyl and $R^{12}$ is hydrogen, alkyl, especially $C_1$–$C_6$-alkyl or an oxo group adjacent to the nitrogen atom, wherein $R^{11}$ and $R^{12}$ optionally together, form an alkylene bridge with 1, 2, 3, 4 or 5 C-atoms, especially a $C_1$–$C_3$-alkylene bridge under formation of a bicyclic ring system, G is selected from hydrogen, G1, G2, G3, G4 and G5, wherein G1 represents the residue

 (G1)

wherein r is an integer from 1 to 3 or 0 and s is 0 or 1, $R^{13}$ is selected from hydrogen, alkyl, especially $C_1$–$C_6$-alkyl, alkenyl with at least three C-atoms, especially $C_3$–$C_6$-alkenyl, alkinyl with at least three C-atoms, especially $C_3$–$C_6$-alkinyl, cycloalkyl with at least three C-atoms, especially $C_3$–$C_8$-cycloalkyl, saturated, five to seven membered heterocycles, which can contain one or two hetero-atoms from the group N and/or S and/or O, benzyl or phenyl, monocyclic aromatic five or six-membered heterocycles, which can contain one to three heteroatoms from the group N and/or S and/or O and are either bound directly or over a methylene group, anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic or a hydrated ring and either directly or over a methylene group, $R^{14}$ has the same meaning as $R^{13}$, but is selected independently thereof, $R^{15}$ is selected from hydrogen, hydroxy, methyl, benzyl, phenyl, monocyclic aromatic five- or six-membered heterocycles, which can contain one to three heteroatoms selected from the group N and/or S and/or O and are either bound directly or over a methylene group, anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic or a hydrated ring and either directly or over a methylene group, G2 is the residue

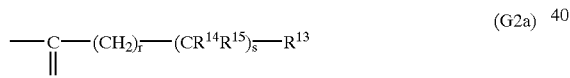 (G2a)

or

wherein the substituents $R^{13}$ and $R^{15}$ can have the above meaning or the grouping

can also be a nitrogen heterocycle bound over the nitrogen atom, selected from saturated or unsaturated monocyclic, four- to eight-membered heterocycles, which, aside from the essential nitrogen atom, can optionally contain one or two further hetero-atoms selected from the group N and/or S and/or O, or saturated or unsaturated bi- or tricyclic, anellated or bridged heterocycles with 8 to 16 ring atoms, which, aside from the essential nitrogen atom, can optionally contain one or two further hetero-atoms selected from the group N and/or S and/or O, G3 is the residue

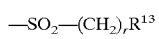 (G3)

and

G4 is the residue

 (G4)

wherein $Ar^1$ and $Ar^2$ are selected independently from one another from phenyl, pyridyl or naphthyl and G5 is the residue

 (G5)

wherein $R^{16}$ is selected from trifluoromethyl, alkoxy, especially $C_1$–$C_6$-alkoxy, alkenyloxy, especially $C_3$–$C_6$-alkenyloxy, or benzyloxy, wherein any aryl residues and/or aromatic ring systems in the substituents $R^1, R^2, R^4, R^{13}, R^{14}, R^{15}, R^{16}, Ar^1$ and $Ar^2$ and/or in the ring system —$NR^{13}R^{15}$ can be substituted independently from each other by one to three of the same or different residues which are selected from halogen, cyano, alkyl, especially $C_1$–$C_6$-alkyl, trifluoromethyl, cycloalkyl, especially $C_3$–$C_8$-cycloalkyl, phenyl, benzyl, hydroxy, alkoxyl, especially $C_1$–$C_6$-alkoxy, alkoxy, substituted entirely or partially by fluorine, substituted alkoxy, especially $C_1$–$C_6$-alkoxy, benzyloxy, phenoxy, mercapto, alkylthio, especially $C_1$–$C_6$-akylthio, carboxy, alkoxycarbonyl, especially $C_1$–$C_6$-alkoxycarbonyl, benzyloxycarbonyl, nitro, amino, monoalkylamino, especially mono-$C_1$–$C_6$-alkylamino, dialkylamino, especially di-($C_1$–$C_6$-alkyl)-amino and methylenedioxy for two adjacent groups on the aromatic ring or ring system, wherein each of the residues alkyl, alkenyl, alkinyl, hydroxyalkyl, alkoxy, alkenyloxy, alkinyloxy, alkanoyloxy, alkoxycarbonyl, alkoxycarbonyloxy, alkylthio, alkenylthio, alkinylthio, alkylene, acyl, alkylsulfonyl, alkenylene, alkinylene, cycloalkyl, cycloalkyloxy, alkoxycarbonyl, alkylaminocarbonyl or dialkylaminocarbonyl of the substituents $R^1$ to $R^{14}$ can have 1 to 2 or 4, 6, 8, 10 or 12 C-atoms and/or 2 or 3 to 5, 7, 9, 11 or 13 and/or 15 C-atoms or 4, 5, 6, 7, 8, 9, 10, 11, 12, 13, 14 or 15 C-atoms depending on the structure, as well as stereoisomers and/or mixtures thereof and pharmacologically acceptable acid addition salts thereof for the production of medicaments for cytostatic or immunomodulatory and/or immunosuppressive treatment.

A preferred embodiment according to the invention relates to the use of compounds of formula (I)

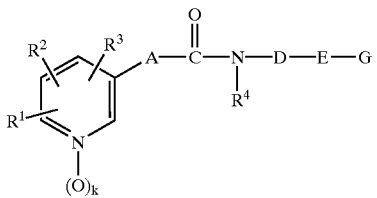

(I)

for the production of medicaments for the indications named above, wherein in the general formula (I)

$R^1$ is a hydrogen, halogen, cyano, $C_1$–$C_6$-alkyl, $C_3$–$C_6$-alkenyl, $C_3$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkylaminocarbonyl, $C_3$–$C_{13}$-dialkylaminocarbonyl, carboxy, phenyl, phenoxy, phenylthio, pyridyloxy, pyridylthio, or $NR^5R^6$, wherein $R^5$ and $R^6$ are selected independently from each other from hydrogen, $C_1$–$C_6$-alkyl, $C_3$–$C_6$-alkenyl and $C_3$–$C_6$-alkinyl, $R^2$ is hydrogen, halogen, cyano, $C_1$–$C_6$-alkyl, trifluoromethyl, hydroxy, $C_1$–$C_6$-alkoxy, benzyloxy or $C_1$–$C_7$-alkanoyloxy,
wherein $R^1$ and $R^2$, in case they are adjacent, optionally form a bridge which is selected from the bridge members —(CH$_2$)$_4$— and —(CH═CH)$_2$— and —CH$_2$O—CR$^7$R$^8$—O—, wherein $R^7$ and $R^8$ are, independently from each other, hydrogen or $C_1$–$C_6$-alkyl, $R^3$ is hydrogen, halogen, $C_1$–$C_6$-alkyl, trifluoromethyl or $C_1$–$C_6$-hydroxyalkyl and $R^4$ is hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy or benzyloxy, k is 0 or 1, A is $C_1$–$C_6$-alkylene, which is optionally substituted once to three-fold by $C_1$–$C_3$-alkyl, hydroxy, $C_1$–$C_3$-alkoxy, fluorine or phenyl, or
1,2-cyclopropylene or
$C_2$–$C_6$-alkenylene, which is optionally substituted once to three-fold by $C_1$–$C_3$-alkyl, hydroxy, $C_1$–$C_3$-alkoxy, fluorine, cyano or phenyl,
$C_4$–$C_6$-alkadienylene, which is optionally substituted once or twice by $C_1$–$C_3$-alkyl, fluorine, cyano or phenyl
1,3,5-hexatrienylene, which is optionally substituted by $C_1$–$C_3$-alkyl, fluorine, cyano or phenyl
ethynylene or
$C_2$–$C_6$-alkylene, wherein a methylene unit can be isosterically replaced by O, S, NR$^9$, CO, SO or SO$_2$, wherein the isosteric substitution, with the exception of ═CO, cannot be adjacent to the amide group, and $R^9$ is selected from hydrogen, $C_1$–$C_6$-alkyl, $C_3$–$C_6$-alkenyl, $C_3$–$C_6$-alkinyl, $C_1$–$C_6$-acyl or $C_1$–$C_6$-alkylsulfonyl, D is selected from $C_1$–$C_{10}$-alkylene, optionally substituted once or twice by $C_1$–$C_6$-alkyl, hydroxy or $C_1$–$C_6$-alkoxy, $C_2$–$C_{10}$-alkenylene, which is optionally substituted once or which by $C_1$–$C_6$-alkyl, hydroxy, or $C_1$–$C_6$-alkoxy, wherein the double bond can also be to ring E, $C_3$–$C_{10}$-alkinylene, optionally substituted once or twice by $C_1$–$C_6$-alkyl, hydroxy, or $C_1$–$C_6$-alkoxy, and $C_1$–$C_{10}$-alkylene, $C_2$–$C_{10}$-alkenylene or $C_3$–$C_{10}$-alkinylene, wherein one to three methylene units are each isosterically replaced by O, S, NR$^{10}$, CO, SO or SO$_2$, wherein $R^{10}$ has the same meaning as $R^9$, but is selected independently therefrom, E is selected from

(E1)

or

(E2)

wherein the heterocyclic ring can optionally have a double bond and n and p can be, independently of each other, 0, 1, 2 or 3, with the proviso that n+p≦4 and q is 2 or 3, $R^{11}$ is hydrogen, $C_1$–$C_6$-alkyl, hydroxy, hydroxymethyl, carboxy or $C_2$–$C_7$-alkoxycarbonyl and $R^{12}$ hydrogen, $C_1$–$C_6$-alkyl or an oxo group adjacent to the nitrogen atom, wherein $R^{11}$ and $R^{12}$ optionally together form a $C_1$–$C_3$-alkylene bridge under formation of a bi-cyclic ring system, G is selected from hydrogen,
G1, G2, G3, G4 and G5, wherein
G1 represents the residue

(G1)

wherein r is an integer from 1 to 3 or 0 and s is 0 or 1, $R^{13}$ is selected from hydrogen, $C_1$–$C_6$-alkyl, $C_3$–$C_6$-alkenyl, $C_3$–$C_6$-alkinyl, $C_3$–$C_8$-cycloalkyl,
saturated, five- to seven-membered heterocycles, which can contain one or two hetero-atoms from the group N and/or S and/or O,
benzyl or phenyl,
monocyclic aromatic five or six-membered heterocycles, which can contain one to three hetero-atoms from the group N and/or S and/or O and are either bound directly or over a methylene group,
anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group,
anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic ring or a hydrated ring and either directly or over a methylene group, $R^{14}$ has the same meaning as $R^{13}$, but is selected independently thereof, $R^{15}$ is selected from hydrogen, hydroxy, methyl, benzyl, phenyl, monocyclic aromatic five- or six-membered heterocycles, which can contain one to three heteroatoms selected from the group N and/or S and/or O and are either bound directly or over a methylene group, anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic ring or a hydrated ring and either directly or over a methylene group.

G2 is the residue

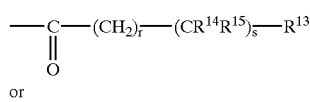

(G2a)

or

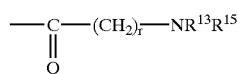

(G2b)

wherein the substituents $R^{13}$ and $R^{15}$ can have the above meaning or the grouping

can also be a nitrogen heterocycle bound over the nitrogen atom, selected from saturated or unsaturated monocyclic, four- to eight-membered heterocycles, which, aside from the essential nitrogen atom, can optionally contain one or two further hetero-atoms selected from the group N and/or S and/or O, or saturated or unsaturated bi- or tricyclic, anellated or bridged heterocycles with 8 to 16 ring atoms, which, aside from the essential nitrogen atom, can optionally contain one or two further hetero-atoms selected from the group N and/or S and/or O, G3 is the residue

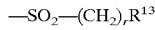 (G3)

and

G4 is the residue

 (G4)

wherein $Ar^1$ and $Ar^2$ are selected independently from one another from phenyl, pyridyl or naphthyl and G5 is the residue

 (G5)

wherein $R^{16}$ is selected from trifluoromethyl, $C_1$–$C_6$-alkoxy, $C_3$–$C_6$-alkenyloxy, or benzyloxy, and wherein aromatic ring systems in the substituents $R^1$, $R^2$, $R^4$, $R^{13}$, $R^{14}$, $R^{15}$, $R^{16}$, $Ar^1$ and $Ar^2$ and/or in the ring system $-NR^{13}R^{15}$ can be substituted independently from each other by one to three of the same or different residues which are selected from halogen, cyano, $C_1$–$C_6$-alkyl, trifluoromethyl, $C_3$–$C_8$-Cycloalkyl, phenyl, benzyl, hydroxy, $C_1$–$C_6$-alkoxy, which can optionally be entirely or partially substituted by fluorine, benzyloxy, phenoxy, mercapto, $C_1$–$C_6$-alkylthio, carboxy, $C_1$–$C_6$-alkoxycarbonyl, benzyloxycarbonyl, nitro, amino, mono-$C_1$–$C_6$-alkylamino or di-($C_1$–$C_6$-alkyl)-amino and methylenedioxy for trio adjacent groups on the aromatic ring or ring system, stereoisomers thereof and/or mixtures thereof and pharmacologically acceptable acid addition salts.

A further preferred embodiment of the invention constitutes the use of compounds for the indications named above, which are distinguished in that substituents $R^1$, $R^2$, $R^3$, $R^4$, $R^5$, $R^6$, $R^7$, $R^8$ $R^9$, $R^{10}$, $R^{13}$, $R^{14}$, $R^{15}$ and $R^{16}$ as well as A and D indicated for formula (I) have the following meaning in connection with the given substitutions according to this formula

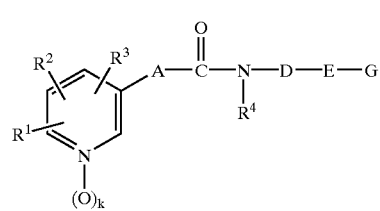 (I)

wherein halogen is fluorine, chlorine, bromine or iodine, $C_1$–$C_6$-alkyl can be straight chain or branched and is preferably a methyl-, ethyl-, propyl-, isopropyl-, butyl-, isobutyl-, sec-butyl-, tert-butyl-, cyclopropylmethyl-, pentyl-, isopentyl-, tert-pentyl-, neopentyl-, cyclopropylethyl-, cyclobutylmethyl- or a hexyl group, alkylene is for example methylene, ethylene, propylene, tetramethylene, pentamethylene, hexamethylene, heptamethylene, octamethylene, nonamethylene or decamethylene, $C_3$–$C_6$-alkenyl can be straight chain or branched and is preferably an allyl-, 2-butenyl-, 3-butenyl-, 2-methyl-2-propenyl-, 2-pentenyl-, 4-pentenyl-, 2-methyl-2-butenyl-, 3-methyl-2-butenyl-, 2-hexenyl-, 5-hexenyl-, 4-methyl-3-pentenyl- or 2,2-dimethyl-3-butenyl group, alkenylene is for example ethenylene, propenylene, butenylene, pentenylene, hexenylene, hexathenylene, heptenylene, octenylene, nonenylene or decenylene, $C_3$–$C_6$-alkinyl can be straight chain or branched and is preferably a propargyl-, 2-butinyl-, 3-butinyl-, 4-pentinyl-, 5-hexinyl- or 4-methyl-2-pentinyl group, alkinylene is for example propinylene, butinylene, pentinylene, hexinylene, heptinylene, octinylene, noninylene or decinylene, $C_3$–$C_8$-cycloalkyl is preferably cyclopropyl, cyclobutyl, cyclopentyl, cyclohexyl, cycloheptyl or cyclooctyl, $C_1$–$C_6$-hydroxyalkyl contains a hydroxyl group in one of the above-named $C_1$–$C_6$-alkyl residues, especially in the form of the hydroxymethyl- and hydroxyethyl group, wherein $C_1$–$C_6$-alkoxy, $C_3$–$C_6$-alkenyloxy, $C_3$–$C_6$-alkinyloxy each contain, aside from the oxygen atom, one of the $C_1$–$C_6$-alkyl-, $C_3$–$C_6$-alkenyl- and/or $C_3$–$C_6$-alkinyl groups named above and the methoxy)-, ethoxy-, isopropoxy-, tert-butoxy-, allyloxy- and propargyloxy group are preferred and is to be understood as among $C_1$–$C_6$-alkoxy entirely or partially substituted with fluorine, for example difluormethoxy, trifluormethoxy or 2,2,2-trifluorethoxy, $C_1$–$C_6$-alkylthio. $C_3$–$C_6$-alkenylthio, $C_3$–$C_6$-alkinylthio each contain, aside from the sulfur atom, one of the $C_1$–$C_6$-alkyl-, $C_3$–$C_6$-alkenyl- or $C_3$–$C_6$-alkinyl group named above, especially the methylthio-, ethylthio-, isopropylthio- and tert-butylthio groups, $C_3$–$C_8$-cycloalkyloxy and $C_3$–$C_8$-cycloalkylthio are preferred as cyclopentyloxy- and cyclopentylthio- and/or cyclohexyloxy- and cyclohexylthio groups, $C_1$–$C_7$-alkanoyloxy groups contain, aside from the oxygen atom, an aliphatic acyl residue with 1 to 7 carbon atoms, especially the acetoxy-, propionyloxy- and pivaloyloxy group, $C_2$–$C_7$-alkoxycarbonyl groups contain, aside from the carbonyl group, one of the $C_1$–$C_6$-alkoxy groups mentioned above, especially the methoxycarbonyl-, ethoxycarbonyl-, isopropoxycarbonyl-, isobutoxycarbonyl- and tert-butoxycarbonyl group, $C_2$–$C_7$-alkoxycarbonyloxy groups contain, aside from the oxygen atom, one of the $C_2$–$C_7$-alkoxycarbonyl residues mentioned above, especially the methoxycarbonyloxy-, ethoxycarbonyloxy-, isopropoxycarbonyloxy-, isobutoxycarbonyloxy- and tert-butoxycarbonyl group as well as the allyloxycarbonyloxy group, $C_2$–$C_7$-alkylaminocarbonyl and $C_3$–$C_{13}$-dialkylaminocarbonyl groups contain, beside the carbonyl group, an alkylamino- and/or dialkylamino residue, whose $C_1$–$C_6$-alkyl groups have the above meanings, wherein the dimethylaminocarbonyl-, diethylaminocarbonyl- and the diisopropylaminocarbonyl groups are preferred, and aside from the unsubstituted amino group, one of the following $C_1$–$C_6$-alkylamino groups and/or di-($C_1$–$C_6$-alkyl)amino groups are to be understood under the amino groups of the formula $NR^5R^6$, $C_1$–$C_6$-alkylamino contains one of the $C_1$–$C_6$-alkyl groups mentioned above, especially in form of the methylamino-, ethylamino-, propylamino-, isopropylamino-, butylamino- and the tert-butylamino group, di-($C_1$–$C_6$-alkyl)amino carries two of the same or different of the above named $C_1$–$C_6$-alkyl groups on the nitrogen atom, especially in form of the dimethylamino-, diethylamino-, dipropylamino-, diisopropylamino-, isopropylmethylamino-, dibutylamino- or tert-butylmethylamino group, $C_1$–$C_6$-acyl is the residue of an aliphatic saturated or unsaturated, straight chain, branched or cyclic carboxylic acid, especially in form of the formyl-, acetyl-, propionyl-, acryloyl-, butyryl-, isobutyryl-, methacryloyl-, cyclopropylcarbonyl-, pentanoyl-, pivaloyl-, cyclobutylcarbonyl-, hexanoyl- and the dimethylacryloyl group, $C_1$–$C_6$-alkansulfonyl is preferably the methanesulfonyl-, ethanesulfonyl-, propanesulfonyl-, butanesulfonyl-, pentanesulfonyl- and the hexanesulfonyl group, saturated five- to seven-membered heterocycles with one or two hetero-atoms are especially tetrahydrofuryl, tetrahydrothienyl, pyrrolidinyl, tetrahydropyranyl, piperidinyl, hexahydroazepinyl, piperazinyl, hexahydrodiazepinyl or morpholinyl, monocyclic aromatic five- or six-membered heterocycles with one to three hetero-atoms are especially furyl, thienyl, pyrrolyl, oxazolyl, isoxazolyl, thiazolyl, isothiazolyl, imidazolyl, pyrazolyl, oxadiazolyl, thiadiazolyl, triazolyl, pyridyl, pyrazinyl, pyridazinyl, pyrimidinyl or triazinyl, anellated bi- and tricyclic aromatic or partially hydrated carbocycle ring systems with 8 to 16 ring atoms and at least one aromatic ring are preferably benzocyclobutyl, indanyl, indenyl, naphthyl, dihydronaphthyl, tetrahydronaphthyl, biphenylenyl, fluorenyl, anthryl, dihydroanthryl, phenanthryl, dihydrophenanthryl, dibenzocycloheptenyl, dihydrodibenzocycloheptenyl, dihydrodibenzocyclooctenyl or tetrahydrodibenzocyclooctenyl, wherein mono- or dioxo-derivates, wherein the residues of indanone, tetralone, anthrone, anthraquinone, fluorenone, phenanthrone, dibenzocycloheptenone, dihydrodibenzocycloheptenone or tetrahydrodibenzocyclooctenone are for example also to be understood as partially hydrated carbocyclic ring systems, anellated bi- and tricyclische aromatic or partially hydrated heterocyclic ring systems with 8 to 16 ring atoms and at least one aromatic ring are, for example, imidazothiazolyl, benzofuryl, dihydrobenzofuryl, benzothienyl, dihydrobenzothienyl, indolyl, indolinyl, benzimidazolyl, indazolyl, benzoxazolyl, benzisoxazolyl, benzothiazolyl, benzoisothiazolyl, benzofurazanyl, benzothiadiazolyl, benzotriazolyl, oxazolopyridyl, thiazolopyridyl, isothiazolopyridyl, imidazopyridyl, pyrazolopyridyl, thienopyrimidinyl, chromanyl, benzopyranyl, quinolyl, isoquinolyl, dihydroquinolyl, tetrahydroquinolyl, benzodioxanyl, quinoxalinyl, quinazolinyl, naphthyridinyl, carbazolyl, tetrahydrocarbazolyl, pyridoindolyl, acridinyl, phenothiazinyl, dihydrodibenzoxepinyl, benzocycloheptathienyl, dihydrothienobenzothiepinyl, dihydrodibenzothiepinyl, octahydrodibenzothiepinyl, dihydrodibenzazepinyl, octahydrodibenzazepinyl, benzocycloheptapyridyl, dihydropyridobenzodiazepinyl, dihydrodibenzoxazepinyl, dihydropnridobenzoxepinyl, dihydropyridobenzoxazepinyl, dihydrodibenzothiazepinyl or dihydropyridobenzothiazepinyl, wherein their mono- or dioxo-derivates and/or optionally their possible tautomeres are also to be understood as partially hydrated heterocyclic ring systems, for example, the residues of indolinone, isatin, benzoxazol one and/or its tautomeres hydroxybenzoxazol, of benzisoxazolone, benzothiazolone, benzoisothiazolone and benzimidazolone and/or their tautomeres, hydroxybenzisoxazol, hydroxybenzothiazol, hydroxybenzoisothiazol and hydroxybenzimidazol, of indazolinone, of oxazolopyridinone, thiazolopyridinones, pyrazolopyridinones and imidazopyridinones and/or their tautomeres hydroxyoxazolopyridine, hydroxythiazolopyridines, hydroxypyrazolopyridines and hydroxyimidazopyridines, the residues of chromanone, chromone, quinolinone, di-hydroquinolinone, tetrahydrocarbazolone, acridone, of dihydrodibenzoxepinones, benzocycloheptathiophenones, dihydrothienobenzothiepinones, dihydrodibenzothiepinones, dihydrodibenzoazepinones, benzocycloheptapyridinones, dihydropyridobenzoxazepinones, dihydrodibenzothiazepinones and of dihydropyridobenzothiazepinones, saturated and unsaturated monocyclic, four- to eight-membered heterocycles are $—NR^{13}R^{15}$ as a grouping which, aside from the essential nitrogen atom, can optionally contain one or two further hetero-atoms selected from N and/or S and/or O, for example azetidine, pyrrolidine, piperidine, (1H) tetrahydropyridine, hexahydroazepine, (1H) tetrahydroazepine, octahydroazocine, pyrazolidine, piperazine, hexahydrodiazepine, morpholine, hexahydrooxazepine, thiomorpholine or thylomorpholine-1,1-dioxide, saturated or unsaturated bi- or tricyclic, anellated or bridged heterocycles with 8 to 16 ring atoms, represent $—NR^{13}R^{15}$ as a grouping which, aside from the essential nitrogen atom optionally contain one or two further hetero-atoms, selected from N and/or S and/or O, for example 5-aza-bicyclo[2.1.1]hexane, 2-aza-bicyclo[2.2.1]heptane, 7-aza-bicyclo[2.2.1]heptane, 2,5-diaza-bicyclo[2.2.1]heptane, 2-aza-bicyclo[2.2.2]octane, 8-aza-bicyclo[3.2.1]octane, 2,5-diaza-bicyclo[2.2.2]octane, 9-aza-bicyclo[3.3.1]nonane, indoline, isoindoline, (1H)-dihydroquinoline, (1H)-tetrahydroquinoline, (2H)-tetrahydroisoquinoline, (1H)-tetrahydroquinoxaline, (4H)-dihydrobenzoxazine, (4H)-dihydrobenothiazine, (1H)-tetrahydrobenzo[b]azepine, (1H)-tetrahydrobenzo[c]azepine, (1H)-tetrahydrobenzo[d]azepine, (5H)-tetrahydrobenzo[b]oxazepine, (5H)-tetrahydrobenzo[b]thiazepine, 1,2,3,4-tetrahydro-9H-pyrido[3,4-b]indol, (10H)-dihydroacridine, 1,2,3,4-tetrahydroacridanone, (10H)-phenoxazin, (10H)-phenothiazine, (5H)-dibenzazepine, (5H)-dihydrodibenzazepine, (5H)-octahydrodibenzazepine, (5H)-dihydrodibenzodiazepine, (11H)-dihydrodibenzo[b,e]oxazepine, (11H)-dihydrodibenzo[b,e]thiazepine, (10H)-dihydro-dibenzo[b,f]oxazepine, (10H)-dihydrodibenzo[b,f]thiazepine or (5H)-tetrahydrodibenzazocine, as well as optionally possible tautomeres in the case of substitution of the heterocycle as such or in an anellated ring system by free hydroxy-, mercapto- and/or amino groups, and their stereoisomers such as, if applicable, cis/trans-isomers, endo/exo-isomers, optic isomers such as enantiomers, diastereomers as pure isomers or mixtures and/or racemic mixtures as well as the pharmacologically acceptable acid addition salts with inorganic or organic acids, wherein the hydrochlorides, hydrobromides, hydroiodides, sulfates and phosphates, are preferred as addition salts with suitable inorganic acids and acetates, benzoates, 4-methoxaybenzoate, 2- or 4-hydroxybenzoate, 4-chlorobenzoate, ascorbate, salicylate, formiate, glutarate, tricarballylate, citrates, fumarates, gluconates, malates, maleates, methanesulfonates, lactates, oxalates, succinates, tartrates and toluolsulfonates, for example p-toluolsulfonate are preferred as addition salts of organic acids.

The use of compounds in which the substitutents labelled in formula (I)

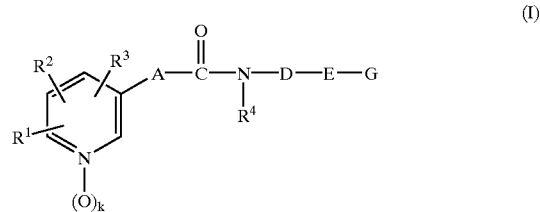

(I)

have the following, meanings, are especially preferred $R^1$ is hydrogen, halogen, cyano, $C_1$–$C_6$-alkyl, trifluoromethyl, $C_3$–$C_8$-cycloalkyl, $C_1$–$C_4$-hydroxyalkyl, hydroxy, $C_1$–$C_4$-alkoxy, benzyloxy, $C_1$–$C_4$-alkanoyloxy, $C_1$–$C_4$-alkylthio, $C_2$–$C_5$-alkoxycarbonyl, aminocarbonyl, $C_3$–$C_9$-dialkylaminocarbonyl, carboxy, phenyl, phenoxy, pyridyloxy or $NR^5R^6$, wherein $R^5$ and $R^6$ are selected independently from each other form hydrogen and $C_1$–$C_6$-alkyl, $R^2$ is hydrogen, halogen, $C_1$–$C_6$-alkyl, trifluoromethyl or hydroxy, wherein $R^1$ and $R^2$, in the case they are adjacent, optionally form a bridge which are selected from the group of bridge members $—(CH_2)_4—$ and $—(CH=CH)_2—$ and $—CH_2O—CR^7R^8—O—$, wherein $R^7$ and $R^8$ can be, independently from each other, hydrogen and $C_1$–$C_6$-alkyl, $R^3$ is selected from hydrogen, halogen and $C_1$–$C_6$-alkyl and $R^4$ is selected from hydropgen, $C_1$–$C_6$-alkyl, $C_3$–$C_6$-alkenyl, hydroxy, $C_1$–$C_6$-alkoxy and benzyloxy, k is 0 or 1, A is $C_1$–$C_6$-alkylene, which is optionally substituted once to three-fold by $C_1$–$C_3$-alkyl, hydroxy, fluorine or phenyl, 1,2-cyclopropylene, $C_2$–$C_6$-alkenylene, which is optionally substituted one to three-fold by $C_1$–$C_3$-alkyl, hydroxy, fluorine, cyano, or phenyl, $C_4$–$C_6$-alkadienylene, which is optionally substituted once or twice by $C_1$–$C_3$-alkyl, fluorine, cyano, or phenyl, 1,3,5-hexatrienylene, which is optionally substituted by $C_1$–$C_3$-alkyl, fluorine, or cyano, ethinylene or $C_2$–$C_6$-alkylene, wherein a methylene unit can be isosterically replaced by O, S, $NR^9$, CO, SO or $SO_2$, and wherein the isosteric substitute, with the exception of =CO, cannot be adjacent to the amide group, and wherein $R^9$ is hydrogen, $C_1$–$C_3$-alkyl, $C_1$–$C_6$-acyl or methanesulfonyl, D is selected from $C_1$–$C_{10}$-alkylene, which is optionally substituted once or twice by $C_1$–$C_3$-alkyl or hydroxy, $C_2$–$C_{10}$-alkenylene, optionally substituted once or twice by $C_1$–$C_3$-alkyl or hydroxy, wherein the double bond can also be to ring E or $C_3$–$C_{10}$-alkinylene, which is optionally substituted once or twice by $C_1$–$C_3$-alkyl or hydroxy, and can be selected as well from $C_1$–$C_{10}$-alkylene, $C_2$–$C_{10}$-alkenylene or $C_3$–$C_{10}$-alkinylene, in which one to three methylene units are isosterically replaced by O, S, $NR^{10}$, CO, SO or $SO_2$, wherein $R^{10}$ has the same meaning as $R^9$, but is selected independently therefrom, E is

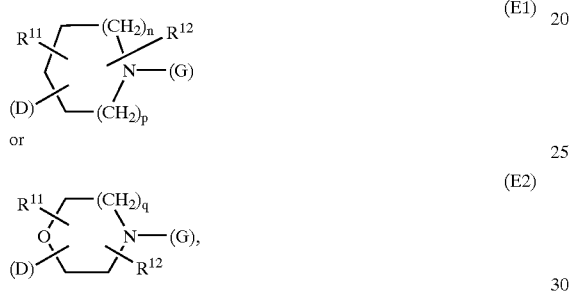

or wherein the heterocyclic ring can optionally have a double bond and n and p can be, independent of each other, 0, 1, 2 or 3, with the proviso that n+p≦4, q is 2 or 3, $R^{11}$ is selected from hydrogen, $C_1$–$C_3$-alkyl, hydroxy, hydroxymethyl, carboxy or $C_2$–$C_7$-alkoxycarbonyl and $R^{12}$ is selected from hydrogen or an oxo group adjacent to the nitrogen atom, G is selected from hydrogen, G1, G2, G3, G4 and G5, wherein G1 represents the residue

wherein
   r is 0, 1 or 2 and
   s is 0 or 1, $R^{13}$ is selected from hydrogen, $C_1$–$C_6$-alkyl, $C_3$–$C_6$-alkenyl, $C_3$–$C_6$-alkinyl, $C_3$–$C_8$-cycloalkyl, benzyl, phenyl, monocyclic aromatic five- or six-membered heterocycles, which contain one to three hetero-atoms from the group N and/or S and/or O and are either bound directly or over a methylene group, anellated bi- and tricyclic aromatic or partially hydrated carbocyclic ring systems with 8 to 16 ring atoms and at least one aromatic ring, whereby the bond can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from the groups N and/or S and/or O and the bond can occur either over an aromatic or a hydrated ring and either directly or over a methylene group, $R^{14}$ has the same meaning as $R^{13}$, but is selected independently thereof, $R^{15}$ is selected from hydrogen, hydroxy, methyl, benzyl or phenyl, monocyclic aromatic five- or six-membered heterocycles, which can contain one to three hetero-atoms selected from the group N and/or S and/or O and are bound either directly or over a methylene group, anellated bi- and tricyclic aromatic or partially hydrated carbocyclic ring systems with 8 to 16 ring atoms and at least einem aromatic ring, wherein the bond can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from the group N and/or S and/or O and the bond can occur either over an aromatic or a hydrated ring and either directly or over a methylene group, G2 is selected from the residues

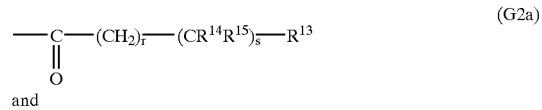

and

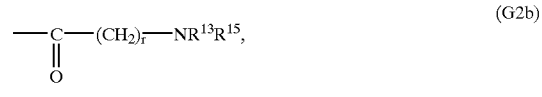

wherein the substituents $R^{13}$ and $R^{15}$ the can have the above meaning, or the grouping

can also be a nitrogen heterocycle bound over the nitrogen atom, selected from saturated or unsaturated monocyclic, four- to eight-membered heterocycles, which, aside from the essential nitrogen atom, can optionally contain one or two further hetero-atoms selected from N and/or S and/or O, or saturated or unsaturated bi- or tricyclic, anellated or bridged heterocycles with 8 to 16 ring atoms, which, aside from the essential nitrogen atom, can optionally contain one or two further hetero-atoms selected from N and/or S and/or O, G3 is the residue

G4 is the residue

wherein
   $Ar^1$ and
   $Ar^2$ are selected independently of each other from phenyl, pyridyl or naphthyl, G5 is the residue $$—COR^{16} \quad (G5)$$

wherein

R$^{16}$ is trifluoromethyl, C$_1$–C$_6$-alkoxy, C$_3$–C$_6$-alkenyloxy or benzyloxy and aromatic ring systems in which the substituents R$^1$, R$^2$, R$^4$, R$^{13}$, R$^{14}$, R$^{15}$, R$^{16}$, Ar$^1$ and Ar$^2$ and/or in the ring system —NR$^{13}$R$^{15}$ can carry independently of each other one to three of the same or different substituents from the series halogen, cyano, C$_1$–C$_6$-alkyl, trifluoromethyl, C$_3$–C$_8$-cycloalkyl, phenyl, benzyl, hydroxy, C$_1$–C$_6$-alkoxy, which is optionally entirely or partially substituted by fluorine, benzyloxy, phenoxy, mercapto, C$_1$–C$_6$-alkylthio, carboxy, C$_1$–C$_6$-alkoxycarbonyl, benzyloxycarbonyl, nitro, amino, mono-C$_1$–C$_6$-alkylamino, di-(C$_1$–C$_6$-alkyl)-amino, wherein two adjacent groups on the aromatic ring or ring system can form an additional ring over a methylenedioxy bridge.

The use of compounds in which the substiutents labelled in formula (I)

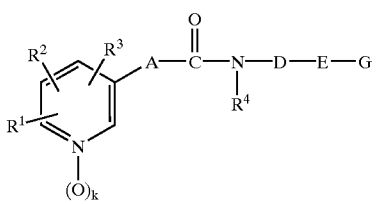

have the following meanings are particularly preferred:

R$^1$ is hydrogen, halogen, cyano, methyl, trifluoromethyl, hydroxy, C$_1$–C$_4$-alkoxy, ethylthio, methoxycarbonyl, tert-butoxycarbonyl, aminocarbonyl, carboxy, and phenoxy, R$^2$ is hydrogen, halogen, trifluoromethyl or hydroxy, R$^3$ is hydrogen or halogen, R$^4$ is selected from hydrogen, C$_1$–C$_3$-alcyl, hydroxy and C$_1$–C$_3$-alkoxy, k is 0 or 1, A is C$_2$–C$_6$-alkylene, which is optionally substituted once or twice by C$_1$–C$_3$-alkyl, hydroxy or fluorine, as well as C$_2$–C$_6$-alkenylene, which is optionally substituted once or twice by C$_1$–C$_3$-alkyl, hydroxy or fluorine C$_4$–C$_6$-alkadienylene, which is optionally substituted by is C$_1$–C$_3$-alkyl or by one or two fluorine atoms, 1,3,5-hexatrienylene, which is optionally substituted by fluorine, or C$_2$–C$_6$-alkylene, wherein a methylene unit can be isosterically replaced by O, S, CO or SO$_2$, and the isosteric substitute, with the exception of =CO, cannot be adjacent to the amide group and, D is C$_1$–C$_8$-alkylene, which is optionally substituted once twice by methyl or hydroxy, C$_2$–C$_8$-alkenylene, which is optionally substituted once or twice by methyl or hydroxy, wherein the double bond can also be to ring E, C$_3$–C$_8$-alkinylene, which is optionally substituted once or twice by methyl or hydroxy, as well as C$_1$–C$_8$-alkylene, C$_2$–C$_8$-alkenylene or C$_3$–C$_8$-alkinylene, in which one to three methylene units can be isosterically replaced by O, S, NH, N(CH$_3$), N(COCH$_3$), N(SO$_2$CH$_3$), CO, SO or SO$_2$, E is

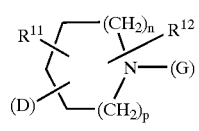

or

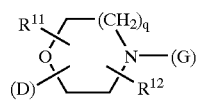

wherein the heterocyclic ring can optionally have a double bond and n and p can be independent of each other 0, 1, 2 or 3, with the proviso that n+p≦3, q is 2 or 3, R$^{11}$ is selected from hydrogen, C$_1$–C$_3$-alkyl, hydroxy, hydroxymethyl and R$^{12}$ is selected from hydrogen or an oxo group which is adjacent to the nitrogen atom, G is hydrogen or G1, G2, G3, G4 and G5, wherein G1 represents the residue $$—(CH_2)_r—(CR^{14}R^{15})_s—R^{13} \quad (G1)$$

wherein r is 0, 1 or 2 and s is 0 or 1,

R$^{13}$ is selected from hydrogen, C$_1$–C$_6$-alkyl, C$_3$–C$_8$-cycloalkyl, benzyl or phenyl, benzocyclobutyl, indanyl, indenyl, oxoindanyl, naphthyl, dihydronaphthyl, tetrahydronaphthyl, oxotetrahydronaphthyl, biphenylenyl, fluorenyl, oxofluorenyl, anthryl, dihydroanthryl, oxodihydroanthryl, dioxodihydroanthryl, phenanthryl, dihydrophenanthryl, oxodihydrophenanthryl, dibenzocycloheptnyl, oxodibenzocycloheptenyl, dihydrodibenzocycloheptenyl. oxodihydrodibenzocycloheptenyl, dihydrodibenzocyclooctenyl, tetrahydrodibenzocyclooctenyl and oxotetrahydrodibenzocyclooctenyl, bound directly or over a methylene group, furyl, thienyl, pyrrolyl, oxazolyl, isoxazolyl, thiazolyl, isothiazolyl, pyrazolyl, imidazoly,l, oxadiazolyl, thiadiazolyl, triazolyl, pyridyl, pyrazinyl, pyridazinyl, pyrimidinyl, triazinyl, imidazothiazolyl, benzofuryl, dihydrobenzofuryl, benzothienyl, dihydrobenzothienyl, indolyl, indolinyl, oxoindolinyl, dioxoindolinyl, benzoxazolyl, oxobenzoxazolinyl, benzisoxazolyl, oxobenzisoxazolinyl, benzothiazolyl, oxobenzthiazolinyl, benzoisothiazolyl, oxobenzoisothiazolinyl, benzimidazolyl, oxobenzimidazolinyl, indazolyl, oxoindazolinyl, benzofurazanyl, benzothiadiazolyl, benzotriazolyl, oxazolopyridyl, oxodihydrooxazolopyridyl, thiazolopyridyl, oxodihydrothiazolopyridyl, isothiazolopyridyl, imidazopyridyl, oxodihydroimidazopyridyl, pyrazolopyridyl, oxodihydropyrazolopyridyl, thienopyrimidinyl, chromanyl, chromanonyl, benzopyranyl, chromanyl, quinolyl, isoquinolyl, dihydroquinolyl, oxodihydroquinolinyl, tetrahydroquinolyl, oxotetrahydroquinolinyl, benzodioxanyl, quinoxalinyl, quinazolinyl, naphthyridinyl, carbazolyl, tetrahydrocarbazolyl, oxotetrahydrocarbazolyl, pyridoindolyl, acridinyl, oxodihydroacridinyl, phenothiazinyl, dihydrodibenzoxepinyl, oxodihydrodibenzoxepinyl, benzocycloheptathienyl, oxobenzocycloheptathienyl, dihydrothienobenzothiepinyl, oxodihydrothienobenzothiepinyl dihydrodibenzothiepinyl, oxodihydrodibenzothiepinyl, octahydrodibenzothiepinyl, dihydrodibenzazepinyl, oxodihydrodibenzazepinyl, octahydrodibenzazepinyl, benzocycloheptapyridyl, oxobenzocycloheptapyridyl, dihydropyridobenzodiazepinyl, dihydrodibenzoxazepinyl, dihydropyridobenzoxepinyl, dihydropyridobenzoxazepinyl, oxodihydropyrdobenzoxazepinyl, dihydrodibenzothiazepinyl, oxodihydrodibenzothiazepinyl, dihydropyridobenzothiazepinyl, oxodihydropyridobenzothiazepinyl, bound directly or over a methylene group, $R^{14}$ has the same meaning as $R^{13}$, but is selected independently therefrom, $R^{15}$ is selected from hydrogen, hydroxy, methyl, benzyl or phenyl, indanyl, indenyl, naphthyl, dihydronaphthyl, tetrahydronaphthyl, furyl, thienyl, pyrrolyl, oxazolyl, isoxazolyl, thiazolyl, isothiazolyl, pyrazolyl, imidazolyl, oxadiazolyl, thiadiazolyl, triazolyl, pyridyl, pyrazinyl, pyridazinyl, pyrimidinyl, triazinyl, benzofuryl, benzothienyl, indolyl, indolinyl, benzoxazolyl, benzothiazolyl, benzimidazolyl, chromanyl, quinolyl or tetrahydroquinolyl bound directly or over a methylene group, G2 is selected from the residues

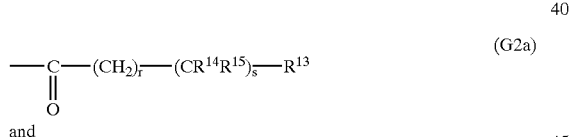

(G2a)

and

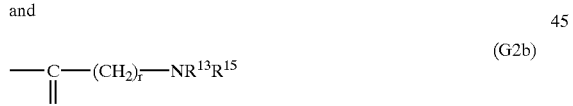

(G2b)

wherein the substituents $R^{13}$ and $R^{15}$ can have the above meanings, or represents the grouping

each over the nitrogen-bound ring atom of azetidine, pyrrolidine, piperidine, (1H)tetrahydropyridine, hexahydroazepine, (1H)tetrahydroazepine, octahydroazocine, pyrazolidine, piperazine, hexyhydrodiazepine, morpholine, hexahydrooxazepine, thiomorpholine, thiomorpholine-1,1-dioxide, 5-aza-bi-cyclo[2.1.1]hexane, 2-aza-bicyclo[2.2.1]heptane, 7-aza-bicyclo[2.2.1]heptane, 2,5-diaza-bicyclo[2.2.1]heptane, 2-aza-bicyclo[2.2.2]octane, 8-aza-bicyclo[3.2.1]octane, 2,5-diazabicyclo[2.2.2]octane, 9-azabicyclo[3.3.1]nonane, indoline, isoindoline, (1H)-dihydroquinoline, (1H)-tetrahydroquinoline, (2H)-tetrahydroisoquinoline, (1H)-tetrahydroquinoxaline, (4H)-dihydrobenzoxazine, (4H)-dihydrobenzothiazine, (1H)-tetrahydrobenzo[b]azepine, (1H)-tetrahydrobenzo[c]azepine, (1H)-tetrahydrobenzo[d]azepine, (5H)-tetrahydrobenzo[b]oxazepine, (5H)-tetrahydrobenzo[b]thiazepine, 1,2,3,4-tetrahydro-9H-pyrido[3,4-b]indole, (10H)-dihydroacridine, 1,2,3,4-tetrahydroacridanone, (10H)-phenoxazine, (10H)-phenothiazine, (5H)-dibenzazepine, (5H)-dihydrodibenzazepine, (5H)-Octahydrodibenzazepine, (5H)-dihydrodibenzodiazepine, (11H)-dihydrodibenzo[b,e]oxazepine, (11H)-dihydrodibenzo[b,e]thiazepine, (10H)-dihydrodibenzo[b,f]oxazepine, (10H)-dihydrodibenzo[b,f]thiazepine or (5H)-tetrahydrodibenzazocine, G3 is the residue

(G3),

G4 is the residue

(G4)

wherein $Ar^1$ and $Ar^2$ are selected independently of each other from phenyl, pyridyl or naphthyl, G5 is the residue

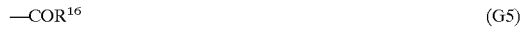

(G5)

wherein $R^{16}$ is trifluoromethyl, $C_1$–$C_6$-alkoxy, $C_3$–$C_6$-alkenyloxy or benzyloxy and aromatic ring systems in which the substituents can be substituted independently of each other by one to three of the same or different substituents from the series halogen, cyano, $C_1$–$C_6$-alkyl, trifluoromethyl, $C_3$–$C_8$-Cycloalkyl phenyl, benzyl, hydroxy, $C_1$–$C_6$-alkoxy, $C_1$–$C_6$-alkoxy, which can be entirely or partially substituted by fluorine, can carry benzyloxy, phenoxy, mercapto, $C_1$–$C_6$-alkylthio, carboxy, $C_1$–$C_6$-alkoxycarbonyl, benzyloxycarbonyl, nitro, amino, mono-$C_1$–$C_6$-alkylamino, di-($C_1$–$C_6$-alkyl)-amino, wherein two adjacent groups in the ring or ring system can form an additional ring over a methylenedioxy bridge.

A further preferred embodiment of the invention is in the use of compounds which are distinguished in that the labelled substituents in formula (I)

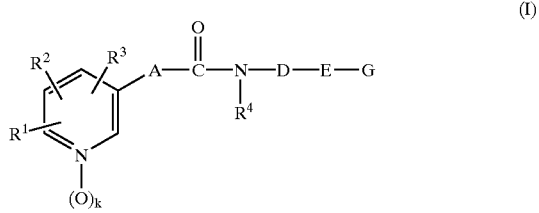

(I)

have the following meaning:

$R^1$ is hydrogen, halogen, cyano, methyl, trifluoromethyl, hydroxy, methoxy or methoxycarbonyl, $R^2$ is hydrogen or halogen, $R^3$ is hydrogen, $R^4$ is selected from hydrogen, $C_1$–$C_3$-alkyl or hydroxy, k is 0 or 1, A is selected from $C_2$–$C_6$-alkylene, which is optionally substituted once or twice by hydroxy or fluorine, or $C_2$–$C_6$-alkenylene, which is optionally substituted once or twice by hydroxy or fluorine, $C_4$–$C_6$-alkadienylene, which is optionally substituted by one or two fluorine atoms, 1,3,5-hexatrienylene or $C_2$–$C_6$-alkylene, wherein a methylene unit can be isosterically replaced by O, S or CO, and the isosteric substitute, with the exception of =CO, cannot be adjacent to the amide group and, D is $C_2$–$C_8$-alkylene, which is optionally substituted by methyl or hydroxy, $C_2$–$C_8$-alkenylene, which is optionally substituted by methyl or hydroxy, wherein the double bond can also be to ring E, or $C_2$–$C_8$-alkylene, $C_2$–$C_8$-alkenylene, wherein one to three methylene units can be isosterically replaced by O, NH, $N(CH_3)$, $N(COCH_3)$, $N(SO_2CH_3)$ or CO, E is selected from the residues

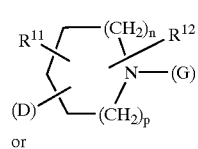

(E1)

or

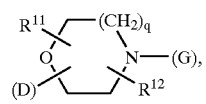

(E2)

wherein the heterocyclic ring can optionally have a double bond and n and p can be, independent of each other, 0, 1, 2 or 3, with the proviso that n+p≦3 and q is 2

$R^{11}$ is hydrogen, methyl or hydroxyl and $R^{12}$ is hydrogen or an oxo group adjacent to the nitrogen atom, G is selected from hydrogen, $C_3$–$C_8$-cycloalkyl, methoxycarbonyl, tert-butoxycarbonyl, benzyloxycarbonyl, trifluoroacetyl, diphenylphosphinoyl or the residues

(G1)

and

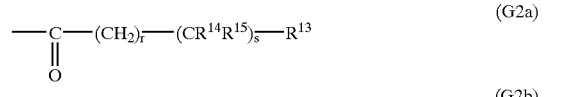

(G2a)

and

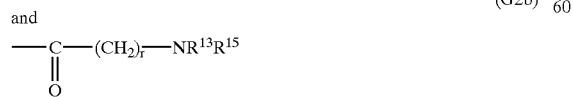

(G2b)

and

(G3)

wherein r is 0, 1 or 2 and s is 0 or 1, $R^{13}$ is hydrogen, methyl, benzyl or phenyl, indanyl, indenyl, oxoindanyl, naphthyl, dihydronaphthyl, tetrahydronaphthyl, oxotetrahydronaphthyl, fluorenyl, oxofluorenyl, anthryl, dihydroanthryl, oxodihydroanthryl, dioxodihydroanthryl, dibenzocycloheptenyl, oxodibenzocycloheptenyl, dihydrodibenzocycloheptenyl, oxodihydrodibenzocycloheptenyl bound directly or over a methylene group, furyl, thienyl, pyrrolyl, oxazolyl, isoxazolyl, thiazolyl, isothiazolyl, pyrazolyl, imidazolyl, oxadiazolyl, thiadiazolyl, triazolyl, pyridyl, pyrazinyl, pyridazinyl, pyrimidinyl, imidazothiazolyl, benzofuryl, dihydrobenzofuryl, benzothienyl, dihydrobenzothienyl, indolyl, indolinyl, oxoindolinyl, dioxoindolinyl, benzoxazolyl, oxobenzoxazolinyl, benzisoxazolyl, oxobenzisoxazolinyl, benzothiazolyl, oxobenzthiazolinyl, benzoisothiazolyl, oxobenzoisothiazolinyl, benzimidazolyl, oxobenzimidazolinyl, benzofurazanyl, benzothiadiazolyl, benzotriazolyl, oxazolopyridyl, oxodihydrooxazolopyridyl, thiazolopyridyl, oxodihydrothiazolopyridyl, isothiazolopyridyl, imidazopyridyl, oxodihydroimidazopyridyl, pyrazolopyridyl, thienopyrimidinyl, chromanyl, chromanonyl, benzopyranyl, chromanyl, quinolyl, isoquinolyl, dihydroquinolyl, oxodihydroquinolinyl, tetrahydroquinolyl, oxotetrahydroquinolinyl, benzodioxanyl, quinoxalinyl, quinazolinyl, naphthyridinyl, carbazolyl, tetrahydrocarbazolyl, oxotetrahydrocarbazolyl, pyridoindolyl, acridinyl, oxodihydroacridinyl, phenothiazinyl, dihydrodibenzoxepinyl, benzocycloheptathienyl, oxobenzocycloheptathienyl, dihydrothienobenzothiepinyl, oxodihydrothienobenzothiepinyl dihydrodibenzothiepinyl, oxodihydrodibenzothiepinyl, dihydrodibenzazepinyl, oxodihydrodibenzazepinyl, octahydrodibenzazepinyl, benzocycloheptapyridyl, oxobenzocycloheptapyridyl, dihydropyridobenzoxepinyl, dihydrodibenzothiazepinyl, oxodihydrodibenzothiazepinyl bound directly or over a methylene group, $R^{14}$ is hydrogen, methyl, benzyl or phenyl, $R^{15}$ is selected from hydrogen, hydroxy, methyl, benzyl, phenyl, naphthyl, furyl, thienyl, oxazolyl, thiazolyl, pyrazolyl, imidazolyl, oxadiazolyl, thiadiazolyl, pyridyl, benzofuryl, benzothienyl, indolyl, indolinyl, benzoxazolyl, benzothiazolyl, benzimidazolyl, chromanyl, quinolyl or tetrahydroquinolyl, bound directly or over a methylene group, wherein in formula (I)

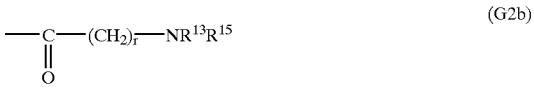

(G2b)

the group $NR^{13}R^{15}$ can be selected from pyrrolidine, piperidine, (1H)tetrahydropyridine, hexahydroazepine, Octahydroazocine, piperazine, hexahydrodiazepine, morpholine, hexahydrooxazepine, 2-azabicyclo[2.2.1]heptane, 7-azabicyclo[2.2.1]heptane, 2,5-diazabicyclo[2.2.1]heptane, 8-azabicyclo[3.2.1]octane, 2,5-diazabicyclo[2.2.2]octane, indoline, isoindoline, (1H)-dihydroquinoline, (1H)-tetrahydroquinoline, (2H)-tetrahydroisoquinoline, (1H)-tetrahydroquinoxaline, (4H)-dihydrobenzoxazine, (4H)-dihydrobenzothiazine, (1H)-tetrahydrobenzo[b]azepine, (1H)-tetrahydrobenzo[d]azepine, (5H)-tetrahydrobenzo[b]oxazepine, (5H)-tetrahydrobenzo[b]thiazepine, 1,2,3,4-tetrahydro-9H-pyrido[3,4-b]indol, (10H)-dihydroacridine, 1,2,3,4-tetrahydroacridanone, (5H)-dihydrodibenzazepine, (5H)-dihydrodibenzodiazepine, (11H)-dihydrodibenzo[b,e]oxazepine, (11H)-dihydrodibenzo[b,e]thiazepine, (10H)-dihydrodibenzo[b,f]oxaze-pine or (5H)-tetrahydrodibenzazocine.

The use of compounds in which the labelled substituents in the formula (I)

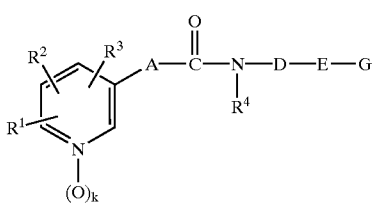
(I)

have the following meanings are very particularly preferred:

$R^1$ is hydrogen. fluorine, chlorine, bromine, methyl, trifluoromethyl or hydroxy, $R^2$ and $R^3$ are hydrogen, $R^4$ is hydrogen or hydroxy, k is 0 or 1, A is selected from $C_2$–$C_6$-alkylene, which is optionally substituted once or twice by hydroxy or fluorine or, $C_2$–$C_4$-alkylene, which is optionally substituted by fluorine, $C_4$-alkadienylene, which is optionally substituted by fluorine, D is selected from $C_2$–$C_6$-alkylene, $C_2$–$C_6$-alkenylene, wherein the double bond can also be to ring E, and $C_2$–$C_6$-alkylene and $C_2$–$C_6$-alkenylene, wherein a methylene unit can be isosterically replaced by O, NH, N(CH$_3$) or CO or an ethylene group can be isosterically replaced by NH—CO and/or CO—NH or a propylene group can be isosterically replaced by NH—CO—O and/or O—CO—NH, E is selected from pyrrolidine, piperidine, 1,2,5,6-tetrahydropyridine, hexahydroazepine, morpholine and hexahydro-1,4-oxazepine, wherein the heterocyclic ring optionally adjacent to the nitrogen atom, can be substituted by an oxo group, G is selected from hydrogen, tert-butoxycarbonyl, diphenylphosphinoyl, or one of the residues —(CH$_2$)$_r$—(CR$^{14}$R$^{15}$)$_s$—R$^{13}$ (G1)

and

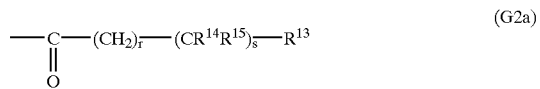
(G2a)

and

(G2b)

and

(G3)

wherein r is 0 or 1 and s is 0 or 1, $R^{13}$ is hydrogen, methyl, benzyl or phenyl, indenyl, oxoindanyl, naphthyl, tetrahydronaphthyl, fluorenyl, oxofluorenyl, anthryl, dihydroanthryl, oxodihydroanthryl, dioxodihydroanthryl, dibenzocycloheptenyl, dihydrodibenzocycloheptenyl bound directly or over a methylene group, furyl, thienyl, oxazolyl, thiazolyl, imidazolyl, oxadiazolyl, thiadiazolyl, pyridyl, pyrazinyl, pyrimidinyl, imidazothiazolyl, benzofuryl, benzothienyl, indolyl, oxoindolinyl, dioxoindolinyl, benzoxazolyl, oxobenzoxazolinyl, benzothiazolyl, oxobenzthiazolinyl, benzimidazolyl, oxobenzimidazolinyl, benzofurazanyl, benzotriazolyl, oxazolopyridyl, oxodihydrooxazolopyridyl, thiazolopyridyl, oxodihydrothiazolopyridyl, chromanyl, chromanonyl, benzopyranyl, chromanyl, quinolyl, isoquinolyl, oxodihydroquinolinyl, tetrahydroquinolyl, oxotetrahydroquinolinyl, benzodioxanyl, quinazolinyl, acridinyl, oxodihydroacridinyl, phenothiazinyl, dihydrodibenzoxepinyl, benzocycloheptathienyl, dihydrothienobenzothiepinyl, dihydrodibenzothiepinyl, oxodihydrodibenzothiepinyl, dihydrodibenzazepinyl, oxodihydrodibenzazepinyl, octahydrodibenzazepinyl, benzocycloheptapyridyl, oxobenzocycloheptapyridyl, dihydrodibenzothiazepinyl bound directly or over a methylene group, $R^{14}$ is hydrogen, methyl, benzyl or phenyl, $R^{15}$ is hydrogen, hydroxy, methyl, benzyl or phenyl, naphthyl, furyl, thienyl, pyridyl, benzofuryl, benzothienyl, indolyl, benzoxazolyl, benzothiazolyl, benzimidazolyl, chromanyl, quinolyl or tetrahydroquinolyl bound directly or over a methylene group, wherein in the formula

(G2b)

the group NR$^{13}$R$^{15}$ can be selected from pyrrolidine, piperidine, hexahydroazepine, morpholine, 2,5-diazabicyclo[2.2.1]heptane, indoline, isoindoline, (1H)-dihydroquinoline, (1H)-tetrahydroquinoline, (2H)-tetrahydroisoquinoline, (1H)-tetrahydrobenzo[b]azepine, (1H)-tetrahydrobenzo[d]azepine, (5H)-tetrahydrobenzo[b]oxazepine, (5H)-tetrahydrobenzo

[b]thiazepine, 1,2,3,4-tetrahydroacridanone, (5H)-dihydrodibenzazepine, (11H)-dihydrodibenzo[b,e]-oxazepine or (11H)-dihydrodibenzo[b,e]thiazepine and wherein aromatic ring systems in the substituents can be substituted, independently of each other, by one to three of the same or different substituents from the series halogen, cyano, $C_1$–$C_6$-alkyl, trifluoromethyl, $C_3$–$C_8$-cycloalkyl, phenyl, benzyl, hydroxy, $C_1$–$C_6$-alkoxy, $C_1$–$C_6$-alkoxy, which can be entirely or partially substituted by fluorine, can carry benzyloxy, phenoxy, mercapto, $C_1$–$C_6$-alkylthio, carboxy, $C_1$–$C_6$-alkoxycarbonyl, benzyloxycarbonyl, nitro, amino, mono-$C_1$–$C_6$-alkylamino or di-($C_1$–$C_6$-alkyl)-amino, whereby two adjacent groups on the aromatic ring or ring system for an additional ring over a methylenedioxy bridge.

The use of compounds is especially preferred which distinguish themselves in that the labelled substituents in the formula (I)

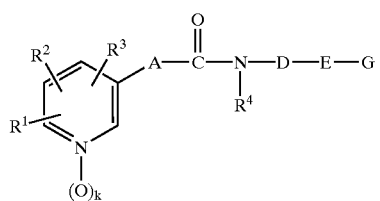

(I)

have the following meanings:
$R^1$ is hydrogen, fluorine, methyl, trifluoromethyl or hydroxy,
$R^2$ and
$R^3$ are hydrogen,
$R^4$ is hydrogen or hydroxy,
k is 0,
A is ethylene, propylene or butylene which can each be optionally substituted by hydroxy or once or twice by fluorine, or
ethenylene and/or vinylene or
1,3-butadienylene
D is selected from $C_2$–$C_6$-alkylene or $C_2$–$C_6$-alkenylene, wherein the double bond can also be to ring E, E is selected from pyrrolidine, piperidine, hexahydroazepine or morpholine,
G is selected from benzyl, phenethyl, fluorenylmethyl, anthrylmethyl, diphenylmethyl, fluorenyl or dihydrodibenzocycloheptenyl,
furylmethyl, thienylmethyl, thiazolylmethyl, pyridylmethyl, benzothienylmethyl, quinolylmethyl, phenyl-thienylmethyl, phenyl-pyridylmethyl, dihydrodibenzoxepinyl, dihydrodibenzothiepinyl,
acetyl, pivaloyl, phenylacetyl, diphenylacetyl, diphenylpropionyl, naphthylacetyl, benzoyl, naphthoyl, anthrylcarbonyl, oxofluorenylcarbonyl, oxodihydroanthrylcarbonyl or dioxodihydroanthrylcarbonyl,
furoyl, pyridylcarbonyl, chromonylcarbonyl, quinolylcarbonyl,
naphthylaminocarbonyl, dibenzylaminocarbonyl, benzylphenylaminocarbonyl, diphenylaminocarbonyl, indolinyl-1-carbonyl, dihydrodibenzazepin-N-carbonyl, tetrahydroquinolinyl-N-carbonyl, tetrahydrobenzo[b]azepinyl-N-carbonyl,
methanesulfonyl, phenylsulfonyl, p-toluolsulfonyl, naphthylsulfonyl, quinolinsulfonyl and
diphenylphosphinoyl,
wherein aromatic ring systems can be substituted independently of each other by one to three of the same or different substituents from the series halogen, cyano, $C_1$–$C_6$-alkyl, trifluoromethyl, $C_3$–$C_8$-cycloalkyl, phenyl, benzyl, hydroxy, $C_1$–$C_6$-alkoxy, $C_1$–$C_6$-alkoxy, which can be entirely or partially substituted by fluorine, benzyloxy, phenoxy, mercapto, $C_1$–$C_6$-alkylthio, carboxy, $C_1$–$C_6$-alkoxycarbonyl, benzyloxycarbonyl, nitro, amino, mono-$C_1$–$C_6$-alkylamino or di-($C_1$–$C_6$-alkyl)-amino, wherein two adjacent groups in the ring or ring system can form an additional ring over a methylendioxy bridge.

A series of compounds with the respective substituent definitions are listed as follows in Table 1 for illustration of the use according to the invention without any intended restriction.

TABLE 1

Exemplifying compounds of formula (I) according to the invention

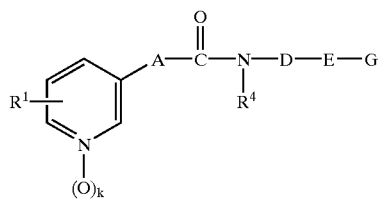

| Nr | $R^1$ | k | A | $R^4$ | D-E-G |
|---|---|---|---|---|---|
| 1 | H | 0 | CH=CH | H | $CH_2$-[azetidine]-N-$CH_2$-phenyl |

TABLE 1-continued
Exemplifying compounds of formula (I) according to the invention
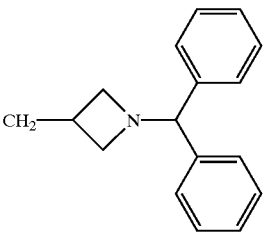
| Nr | R¹ | k | A | R⁴ | D-E-G |
|---|---|---|---|---|---|
| 2 | H | 0 | CH=CH | H | 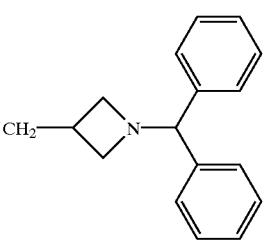 |
| 3 | H | 0 | CH₂CH₂CH₂CH₂ | H | |
| 4 | H | 0 | CH=CH | H | 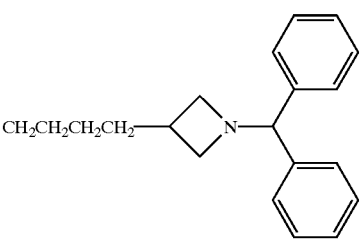 |
| 5 | H | 0 | CH=CH | H | 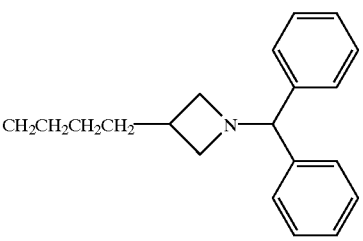 |
| 6 | H | 0 | CH₂CH₂ | H | 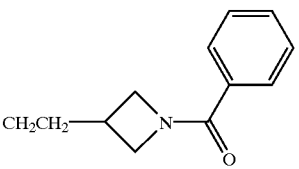 |

TABLE 1-continued

Exemplifying compounds of formula (I) according to the invention

| Nr | R¹ | k | A | R⁴ | D-E-G |
|----|----|----|----|----|----|
| 7 | H | 0 | CH=CH—CH=CH | H | CH₂CH₂CH₂CH₂-azetidine-N-C(O)-fluorenone |
| 8 | H | 0 | CH=CH | H | CH₂CH₂CH₂CH₂-azetidine-N-SO₂-naphthyl |
| 9 | H | 0 | CH₂CH₂ | H | CH₂CH₂-pyrrolidine-N-CH₂-phenyl |
| 10 | H | 0 | CH=CH | H | CH₂CH₂CH₂CH₂-pyrrolidine-N-CH₂-phenyl |
| 11 | H | 0 | CH₂CH₂ | H | CH₂CH₂NH-C(O)-O-pyrrolidine-N-CH₂-phenyl |
| 12 | H | 0 | CH=CH | H | CH₂CH₂NH-C(O)-O-pyrrolidine-N-CH₂-phenyl |
| 13 | H | 0 | CH=CH | H | CH₂CH₂-pyrrolidine-N-CH(phenyl)₂ |

TABLE 1-continued
Exemplifying compounds of formula (I) according to the invention
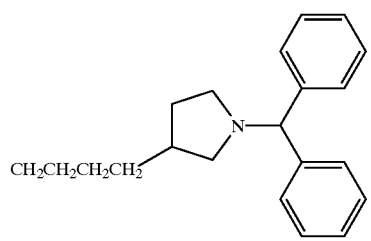
| Nr | R¹ | k | A | R⁴ | D-E-G |
|---|---|---|---|---|---|
| 14 | H | 0 | CH₂CH₂CH₂CH₂ | H | 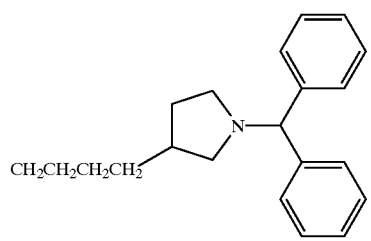 |
| 15 | H | 0 | CH=CH—CH=CH | H | 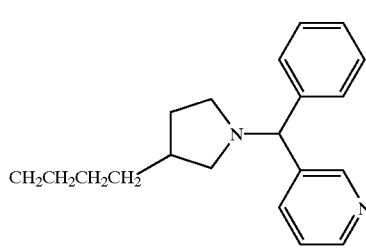 |
| 16 | H | 0 | CH₂CH₂ | H | 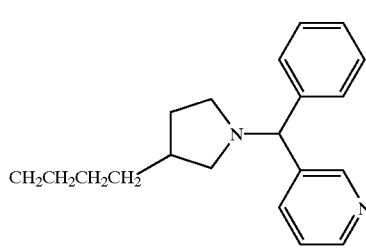 |
| 17 | H | 0 | CH=CH | H | 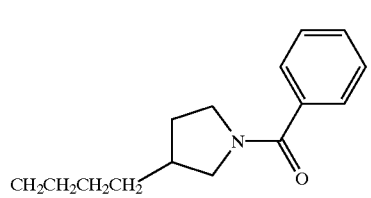 |
| 18 | H | 0 | CH₂CH₂ | H | 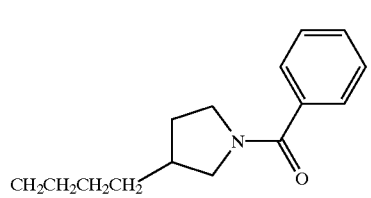 |
| 19 | H | 0 | CH=CH | H | 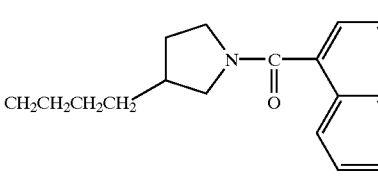 |

TABLE 1-continued
Exemplifying compounds of formula (I) according to the invention
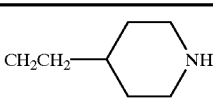
| Nr | R¹ | k | A | R⁴ | D-E-G |
|----|-----|---|------------------|----|-------|
| 20 | H   | 0 | CH₂CH₂           | H  | 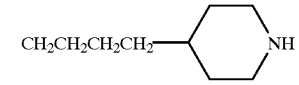 |
| 21 | H   | 0 | CH₂CH₂           | H  | 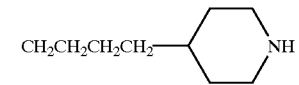 |
| 22 | H   | 0 | CH=CH            | H  | 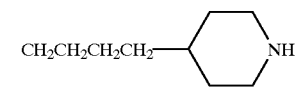 |
| 23 | H   | 0 | CH₂CH₂CH₂CH₂     | H  | 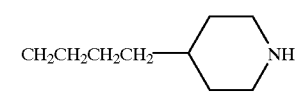 |
| 24 | H   | 0 | CH=CH—CH=CH      | H  | 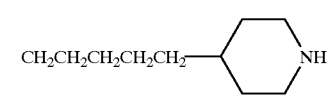 |
| 25 | H   | 0 | CH₂CH₂           | H  | 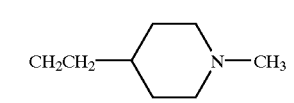 |
| 26 | H   | 0 | CH₂CH₂           | H  | 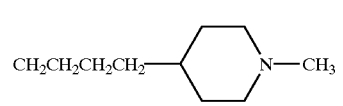 |
| 27 | 6-Cl | 0 | CH=CH           | H  | 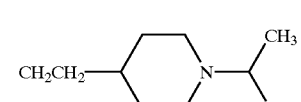 |
| 28 | 2-CH₂ | 0 | CH₂CH₂         | H  | 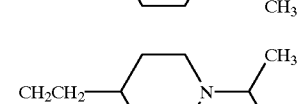 |
| 29 | H   | 0 | CH=CH            | H  | 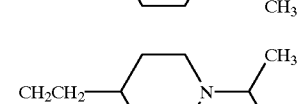 |
| 30 | H   | 0 | CH=CH            | H  | 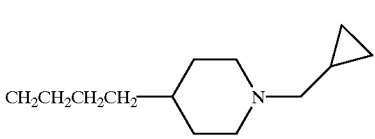 |
| 31 | H   | 0 | CH=CH            | H  | 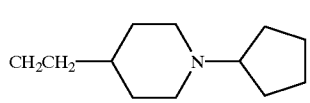 |

TABLE 1-continued

Exemplifying compounds of formula (I) according to the invention

| Nr | R¹ | k | A | R⁴ | D-E-G |
|----|----|----|----|----|-------|
| 32 | H | 0 | CH₂CH₂CH₂ | H | CH₂CH₂-piperidine-N-cyclopentyl |
| 33 | H | 0 | CH₂CH₂ | H | CH₂CH₂-piperidine-N-cyclohexyl |
| 34 | H | 0 | CH=CH | H | (CH₂)₆-piperidine-N-cycloheptyl |
| 35 | H | 0 | CH₂ | H | CH₂-piperidine-N-CH₂-4-piperidine-NH |
| 36 | H | 0 | CH₂CH₂CH₂ | H | CH₂-piperidine-N-CH₂-4-piperidine-NH |
| 37 | H | 0 | CH₂CH₂ | H | CH₂CH₂-piperidine-N-CH₂-4-piperidine-NH |
| 38 | H | 0 | CH₂CH₂ | H | CH₂CH₂-piperidine-N-CH₂-3-piperidine-NH |
| 39 | H | 0 | CH₂CH₂ | H | CH₂CH₂-piperidine-N-CH₂-2-piperidine-NH |
| 40 | H | 0 | CH₂CH₂ | H | CH₂-piperidine-N-CH₂-C₆H₅ |
| 41 | H | 0 | CH₂CH₂ | H | CH₂CH₂-piperidine-N-CH₂-C₆H₅ |
| 42 | H | 0 | CH=CH | H | CH₂CH₂-piperidine-N-CH₂-C₆H₅ |
| 43 | H | 0 | CH₂CH₂CH₂ | H | CH₂CH₂-piperidine-N-CH₂-C₆H₅ |

TABLE 1-continued

Exemplifying compounds of formula (I) according to the invention

| Nr | R¹ | k | A | R⁴ | D-E-G |
|---|---|---|---|---|---|
| 44 | H | 0 | CH₂CH₂ | H | CH₂CH₂CH₂CH₂-[piperidine]-N-CH₂-C₆H₅ |
| 45 | H | 1 | CH₂CH₂ | H | CH₂CH₂CH₂CH₂-[piperidine]-N-CH₂-C₆H₅ |
| 46 | H | 0 | CH=CH | H | CH₂CH₂CH₂CH₂-[piperidine]-N-CH₂-C₆H₅ |
| 47 | H | 1 | CH=CH | H | CH₂CH₂CH₂CH₂-[piperidine]-N-CH₂-C₆H₅ |
| 48 | 2-Cl | 0 | CH=CH | H | CH₂CH₂CH₂CH₂-[piperidine]-N-CH₂-C₆H₅ |
| 49 | 2-F | 0 | CH=CH | H | CH₂CH₂CH₂CH₂-[piperidine]-N-CH₂-C₆H₅ |
| 50 | 5-F | 0 | CH=CH | H | CH₂CH₂CH₂CH₂-[piperidine]-N-CH₂-C₆H₅ |
| 51 | 6-CH₃O | 0 | CH=CH | H | CH₂CH₂CH₂CH₂-[piperidine]-N-CH₂-C₆H₅ |
| 52 | H | 0 | CH=C(CH₃) | H | CH₂CH₂CH₂CH₂-[piperidine]-N-CH₂-C₆H₅ |
| 53 | H | 0 | CH=CH | CH₃ | CH₂CH₂CH₂CH₂-[piperidine]-N-CH₂-C₆H₅ |
| 54 | H | 0 | CH₂CH₂ | H | CH₂CH₂CH₂O-[piperidine]-N-CH₂-C₆H₅ |
| 55 | H | 0 | CH=CH | H | CH₂CH₂CH₂O-[piperidine]-N-CH₂-C₆H₅ |

TABLE 1-continued

Exemplifying compounds of formula (I) according to the invention

| Nr | R¹ | k | A | R⁴ | D-E-G |
|---|---|---|---|---|---|
| 56 | H | 0 | CH=CH | H | -CH₂CH₂CH₂CH₂-(piperidin-3-yl, N-CH₂-C₆H₅) |
| 57 | H | 0 | CH=CH | H | -CH₂CH₂CH₂CH₂CH₂-(piperidin-4-yl, N-CH₂-C₆H₅) |
| 58 | H | 0 | CH=CH | H | -(CH₂)₆-(piperidin-4-yl, N-CH₂-C₆H₅) |
| 59 | H | 0 | CH₂CH₂ | H | -CH₂CH₂-(2-oxopiperidin-4-yl, N-CH₂-C₆H₅) |
| 60 | H | 0 | CH=CH | H | -CH₂CH₂-(2-oxopiperidin-4-yl, N-CH₂-C₆H₅) |
| 61 | H | 0 | CH=CH | H | -CH₂CH₂CH₂CH₂-(2-oxopiperidin-4-yl, N-CH₂-C₆H₅) |
| 62 | H | 0 | CH₂CH₂ | H | -CH₂CH₂-(piperidin-4-yl, N-CH₂CH₂-C₆H₅) |
| 63 | H | 0 | CH=CH | H | -CH₂CH₂-(piperidin-4-yl, N-CH₂CH₂-C₆H₅) |
| 64 | H | 0 | CH=CH | H | -CH₂CH₂CH₂CH₂-(piperidin-4-yl, N-CH₂CH₂-C₆H₅) |

TABLE 1-continued

Exemplifying compounds of formula (I) according to the invention

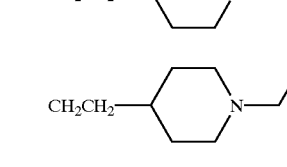

| Nr | R¹ | k | A | R⁴ | D-E-G |
|----|----|----|----|----|-------|
| 65 | H | 0 | CH₂CH₂CH₂CH₂ | H | CH₂CH₂CH₂CH₂—[piperidine]—N—CH₂CH₂—phenyl |
| 66 | H | 0 | CH₂CH₂ | H | CH₂CH₂—[piperidine]—N—CH₂CH₂CH₂—phenyl |
| 67 | H | 0 | CH=C(CH₃) | H | CH₂CH₂—[piperidine]—N—CH₂CH₂CH₂—phenyl |
| 68 | H | 0 | CH₂CH₂ | H | CH₂CH₂—[piperidine]—N—CH₂CH₂CH(OH)—phenyl |
| 69 | H | 0 | CH₂CH₂CH₂ | H | CH₂CH₂—[piperidine]—N—CH₂CH₂CH(OH)—phenyl |
| 70 | H | 0 | CH₂CH₂ | H | CH₂CH₂—[piperidine]—N—CH₂—C₆H₄—OH |
| 71 | H | 0 | CH=CH | H | CH₂CH₂CH₂CH₂—[piperidine]—N—CH₂—C₆H₄—CH |
| 72 | H | 0 | CH₂CH₂ | H | CH₂CH₂—[piperidine]—N—CH₂—C₆H₄—OCH₃ |
| 73 | H | 0 | CH=CH | H | CH₂CH₂CH₂CH₂—[piperidine]—N—CH₂—C₆H₄—OCH₃ |
| 74 | H | 0 | CH₂CH₂ | H | CH₂CH₂CH₂CH₂—[piperidine]—N—CH₂—C₆H₄—C₆H₅ |
| 75 | H | 0 | CH=CH | H | CH₂CH₂CH₂CH₂—[piperidine]—N—CH₂—C₆H₄—C₆H₅ |

TABLE 1-continued

Exemplifying compounds of formula (I) according to the invention

| Nr | R¹ | k | A | R⁴ | D-E-G |
|----|----|----|------|-----|-------|
| 76 | H | 0 | CH₂CH₂ | H | CH₂CH₂—[4-piperidinyl]—N—CH₂—(2-phenylphenyl) |
| 77 | H | 0 | CH=CH | H | CH₂CH₂—[4-piperidinyl]—N—CH₂—(2-phenylphenyl) |
| 78 | H | 0 | CH=CH | H | CH₂CH₂—[4-piperidinyl]—N—CH₂—(1-naphthyl) |
| 79 | H | 0 | CH=CH | H | CH₂CH₂CH₂CH₂—[4-piperidinyl]—N—CH₂—(1-naphthyl) |
| 80 | H | 0 | CH₂CH₂ | H | CH₂CH₂CH₂CH₂—[4-piperidinyl]—N—CH₂—(9-anthracenyl) |
| 81 | H | 0 | CH=CH | H | CH₂CH₂CH₂CH₂—[4-piperidinyl]—N—CH₂—(1-anthracenyl) |

TABLE 1-continued

Exemplifying compounds of formula (I) according to the invention

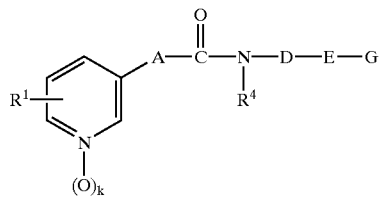

| Nr | R¹ | k | A | R⁴ | D-E-G |
|---|---|---|---|---|---|
| 82 | H | 0 | CH₂CH₂ | H | CH₂CH₂–[4-piperidinyl]–N–CH(CH₃)(C₆H₅) |
| 83 | H | 0 | CH₂CH₂ | H | CH₂CH₂CH₂CH₂–[4-piperidinyl]–N–CH(C₆H₅)(cyclohexyl) |
| 84 | H | 0 | CH=CH | H | CH₂CH₂CH₂CH₂–[4-piperidinyl]–N–CH(C₆H₅)(cyclohexyl) |
| 85 | H | 0 | CH₂CH₂ | H | CH₂CH₂–[4-piperidinyl]–N–CH₂–(3-pyridyl) |
| 86 | H | 0 | CH=CH | H | CH₂CH₂–[4-piperidinyl]–N–CH₂–(3-pyridyl) |
| 87 | H | 0 | CH=CH—CH=CH | H | CH₂CH₂CH₂CH₂–[4-piperidinyl]–N–CH₂–(benzo[2,1,3]oxadiazol-5-yl) |
| 88 | H | 0 | CH₂CH₂ | H | CH₂–[4-piperidinyl]–N–CH(C₆H₅)₂ |

TABLE 1-continued

Exemplifying compounds of formula (I) according to the invention

| Nr | R$^1$ | k | A | R$^4$ | D-E-G |
|---|---|---|---|---|---|
| 89 | H | 0 | CH=CH | H | CH$_2$—[piperidine]—CH(C$_6$H$_5$)$_2$ |
| 90 | H | 0 | CH$_2$ | H | CH$_2$CH$_2$—[piperidine]—CH(C$_6$H$_5$)$_2$ |
| 91 | H | 0 | CH$_2$CH$_2$ | H | CH$_2$CH$_2$—[piperidine]—CH(C$_6$H$_5$)$_2$ |
| 92 | H | 1 | CH$_2$CH$_2$ | H | CH$_2$CH$_2$—[piperidine]—CH(C$_6$H$_5$)$_2$ |
| 93 | 2-F | 0 | CH$_2$CH$_2$ | H | CH$_2$CH$_2$—[piperidine]—CH(C$_6$H$_5$)$_2$ |
| 94 | 6-CH$_3$ | 0 | CH$_2$CH$_2$ | H | CH$_2$CH$_2$—[piperidine]—CH(C$_6$H$_5$)$_2$ |
| 95 | H | 0 | CH=CH | H | CH$_2$CH$_2$—[piperidine]—CH(C$_6$H$_5$)$_2$ |
| 96 | H | 0 | CH$_2$CH$_2$ | H | CH$_2$CH$_2$CH$_2$—[piperidine]—CH(C$_6$H$_5$)$_2$ |
| 97 | H | 0 | CH=CH | H | CH$_2$CH$_2$CH$_2$—[piperidine]—CH(C$_6$H$_5$)$_2$ |
| 98 | H | 0 | CH$_2$CH$_2$ | H | CH$_2$CH$_2$NH—[piperidine]—CH(C$_6$H$_5$)$_2$ |
| 99 | H | 0 | CH=CH | H | CH$_2$CH$_2$NH—[piperidine]—CH(C$_6$H$_5$)$_2$ |
| 100 | H | 0 | CH$_2$CH$_2$ | H | CH$_2$CH$_2$CH$_2$CH$_2$—[piperidine]—CH(C$_6$H$_5$)$_2$ |

TABLE 1-continued

Exemplifying compounds of formula (I) according to the invention

| Nr | R¹ | k | A | R⁴ | D-E-G |
|---|---|---|---|---|---|
| 101 | H | 1 | CH$_2$CH$_2$ | H | CH$_2$CH$_2$CH$_2$CH$_2$—[piperidine]—N—CH(C$_6$H$_5$)$_2$ |
| 102 | 2-OH | 0 | CH$_2$CH$_2$ | H | CH$_2$CH$_2$CH$_2$CH$_2$—[piperidine]—N—CH(C$_6$H$_5$)$_2$ |
| 103 | 6-CH$_3$O | 0 | CH$_2$CH$_2$ | H | CH$_2$CH$_2$CH$_2$CH$_2$—[piperidine]—N—CH(C$_6$H$_5$)$_2$ |
| 104 |  | 0 | CH=CH | H | CH$_2$CH$_2$CH$_2$CH$_2$—[piperidine]—N—CH(C$_6$H$_5$)$_2$ |
| 105 |  | 1 | CH=CH | H | CH$_2$CH$_2$CH$_2$CH$_2$—[piperidine]—N—CH(C$_6$H$_5$)$_2$ |
| 106 | 2-OH | 0 | CH=CH | H | CH$_2$CH$_2$CH$_2$CH$_2$—[piperidine]—N—CH(C$_6$H$_5$)$_2$ |
| 107 | 2-F | 0 | CH=CH | H | CH$_2$CH$_2$CH$_2$CH$_2$—[piperidine]—N—CH(C$_6$H$_5$)$_2$ |
| 108 | 5-F | 0 | CH=CH | H | CH$_2$CH$_2$CH$_2$CH$_2$—[piperidine]—N—CH(C$_6$H$_5$)$_2$ |
| 109 | 6-F | 0 | CH=CH | H | CH$_2$CH$_2$CH$_2$CH$_2$—[piperidine]—N—CH(C$_6$H$_5$)$_2$ |
| 110 | 2-Cl | 0 | CH=CH | H | CH$_2$CH$_2$CH$_2$CH$_2$—[piperidine]—N—CH(C$_6$H$_5$)$_2$ |
| 111 | 6-C$_2$H$_6$S | 0 | CH=CH | H | CH$_2$CH$_2$CH$_2$CH$_2$—[piperidine]—N—CH(C$_6$H$_5$)$_2$ |
| 112 | 6-C$_6$H$_6$O | 0 | CH=CH | H | CH$_2$CH$_2$CH$_2$CH$_2$—[piperidine]—N—CH(C$_6$H$_5$)$_2$ |

TABLE 1-continued

Exemplifying compounds of formula (I) according to the invention

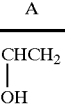

| Nr | R¹ | k | A | R⁴ | D-E-G |
|---|---|---|---|---|---|
| 113 | H | 0 | CHCH₂ \| OH | H | CH₂CH₂CH₂CH₂-piperidine-N-CH(C₆H₅)₂ |
| 114 | H | 0 | CH₂CH \| OH | H | CH₂CH₂CH₂CH₂-piperidine-N-CH(C₆H₅)₂ |
| 115 | H | 0 | CH=C \| CH₃ | H | CH₂CH₂CH₂CH₂-piperidine-N-CH(C₆H₅)₂ |
| 116 | H | 0 | CH₂CH \| C₆H₅ | H | CH₂CH₂CH₂CH₂-piperidine-N-CH(C₆H₅)₂ |
| 117 | H | 0 | CH=C \| C₆H₅ | H | CH₂CH₂CH₂CH₂-piperidine-N-CH(C₆H₅)₂ |
| 118 | H | 0 | CCH₂ ‖ O | H | CH₂CH₂CH₂CH₂-piperidine-N-CH(C₆H₅)₂ |
| 119 | H | 0 | CH₂C ‖ O | H | CH₂CH₂CH₂CH₂-piperidine-N-CH(C₆H₅)₂ |
| 120 | H | 0 | CH₂CF₂ | H | CH₂CH₂CH₂CH₂-piperidine-N-CH(C₆H₅)₂ |
| 121 | H | 0 | CH=CH | CH₃ | CH₂CH₂CH₂CH₂-piperidine-N-CH(C₆H₅)₂ |
| 122 | H | 0 | CH₂CH₂ | C₂H₅ | CH₂CH₂CH₂CH₂-piperidine-N-CH(C₆H₅)₂ |
| 123 | H | 0 | CH=CH | C₂H₅ | CH₂CH₂CH₂CH₂-piperidine-N-CH(C₆H₅)₂ |
| 124 | H | 0 | CH=CH | CH₂ \| CH=CH₂ | CH₂CH₂CH₂CH₂-piperidine-N-CH(C₆H₅)₂ |

TABLE 1-continued

Exemplifying compounds of formula (I) according to the invention

| Nr | R¹ | k | A | R⁴ | D-E-G |
|---|---|---|---|---|---|
| 125 | H | 0 | CH₂CH₂ | OH | CH₂CH₂CH₂CH₂—[piperidine]—N—CH(C₆H₅)₂ |
| 126 | H | 0 | CH=CH | OH | CH₂CH₂CH₂CH₂—[piperidine]—N—CH(C₆H₅)₂ |
| 127 | H | 0 | △ (cyclopropyl) | H | CH₂CH₂CH₂CH₂—[piperidine]—N—CH(C₆H₅)₂ |
| 128 | H | 0 | C≡C | H | CH₂CH₂CH₂CH₂—[piperidine]—N—CH(C₆H₅)₂ |
| 129 | H | 0 | OCH₂ | H | CH₂CH₂CH₂CH₂—[piperidine]—N—CH(C₆H₅)₂ |
| 130 | H | 0 | SCH₂CH₂ | H | CH₂CH₂CH₂CH₂—[piperidine]—N—CH(C₆H₅)₂ |
| 131 | H | 0 | CH₂CH₂CH₂CH₂ | H | CH₂CH₂CH₂CH₂—[piperidine]—N—CH(C₆H₅)₂ |
| 132 | H | 0 | CH=CH.CH=CH | H | CH₂CH₂CH₂CH₂—[piperidine]—N—CH(C₆H₅)₂ |
| 133 | H | 0 | CH₂NHCH₂CH₂ | H | CH₂CH₂CH₂CH₂—[piperidine]—N—CH(C₆H₅)₂ |
| 134 | H | 0 | CH₂NCH₂CH₂ (N-CHO) | H | CH₂CH₂CH₂CH₂—[piperidine]—N—CH(C₆H₅)₂ |
| 135 | H | 0 | CH₂NCH₂CH₂ (N-SO₂CH₃) | H | CH₂CH₂CH₂CH₂—[piperidine]—N—CH(C₆H₅)₂ |
| 136 | H | 0 | CH=CH | H | CH₂CH₂CH₂CH₂—[3-piperidine]—N—CH(C₆H₅)₂ |

TABLE 1-continued

Exemplifying compounds of formula (I) according to the invention

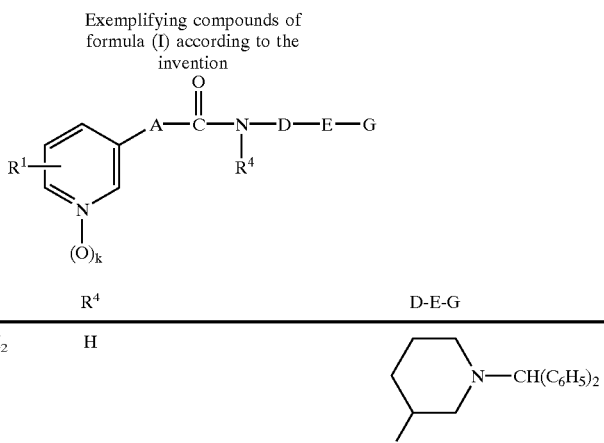

| Nr | R¹ | k | A | R⁴ | D-E-G |
|---|---|---|---|---|---|
| 137 | H | 0 | CH₂CH₂CH₂CH₂ | H | CH₂CH₂CH₂CH₂—[piperidine-3-yl]—N—CH(C₆H₅)₂ |
| 138 | H | 0 | CH₂CH₂ | H | CH₂CH₂CH₂O—[piperidin-4-yl]—N—CH(C₆H₅)₂ |
| 139 | H | 0 | CH₂CH₂CH₂CH₂ | H | CH₂CH₂CH₂O—[piperidin-4-yl]—N—CH(C₆H₅)₂ |
| 140 | H | 0 | CH₂CH₂CH₂ | H | CH₂CH₂CH₂CH=[piperidin-4-ylidene]—N—CH(C₆H₅)₂ |
| 141 | H | 0 | CH₂CH₂CH₂CH₂ | H | CH₂CH=CHCH₂—[piperidin-4-yl]—N—CH(C₆H₅)₂ |
| 142 | H | 0 | CH₂CH₂ | H | CH₂CH₂CH₂CH₂CH₂—[piperidin-4-yl]—N—CH(C₆H₅)₂ |
| 143 | H | 0 | CH=CH | H | CH₂CH₂CH₂CH₂CH₂—[piperidin-4-yl]—N—CH(C₆H₅)₂ |
| 144 | H | 0 | CH₂CH₂CH₂CH₂ | H | CH₂CH₂CH₂CH₂CH₂—[piperidin-4-yl]—N—CH(C₆H₅)₂ |
| 145 | H | 0 | CH₂CH₂CH₂CH₂ | H | CH₂CH₂CH₂OCH₂—[piperidin-4-yl]—N—CH(C₆H₅)₂ |
| 146 | H | 0 | CH=CH | H | OCH₂CH₂CH₂—[piperidin-4-yl]—N—CH(C₆H₅)₂ |
| 147 | H | 0 | CH=CH | H | CH₂CH₂NH—C(=O)—O—[piperidin-4-yl]—N—CH(C₆H₅)₂ |
| 148 | H | 0 | CH=CH | H | CH₂CH₂CH₂CH₂CH₂CH₂—[piperidin-4-yl]—N—CH(C₆H₅)₂ |

TABLE 1-continued

Exemplifying compounds of formula (I) according to the invention

| Nr | R¹ | k | A | R⁴ | D-E-G |
|---|---|---|---|---|---|
| 149 | H | 0 | OCH$_2$ | H | CH$_2$CH$_2$CH$_2$CH$_2$CH$_2$-piperidine-N-CH(C$_6$H$_5$)$_2$ |
| 150 | H | 0 | CH$_2$CH$_2$ | H | CH$_2$CH$_2$CH$_2$CH$_2$NH-C(=O)-[3-piperidinyl]-N-CH(C$_6$H$_5$)$_2$ |
| 151 | H | 0 | CH$_2$ | H | (CH$_2$)$_6$-piperidine-N-CH(C$_6$H$_5$)$_2$ |
| 152 | H | 0 | CH=CH | H | (CH$_2$)$_6$NH-C(=O)-[4-piperidinyl]-N-CH(C$_6$H$_5$)$_2$ |
| 153 | H | 0 | CH$_2$CH$_2$ | H | (CH$_2$)$_6$NH-C(=O)-[3-piperidinyl]-N-CH(C$_6$H$_5$)$_2$ |
| 154 | H | 0 | CH=CH | H | (CH$_2$)$_6$NH-C(=O)-[3-piperidinyl]-N-CH(C$_6$H$_5$)$_2$ |
| 155 | H | 0 | CH$_2$CH$_2$ | H | CH$_2$CH$_2$-[4-HO-piperidinyl]-N-CH(C$_6$H$_5$)$_2$ |
| 156 | H | 0 | CH=CH | H | CH$_2$CH$_2$-[4-HO-piperidinyl]-N-CH(C$_6$H$_5$)$_2$ |
| 157 | H | 0 | CH$_2$CH$_2$ | H | CH$_2$CH$_2$-[4-(2-oxo)piperidinyl]-N-CH(C$_6$H$_5$)$_2$ |

TABLE 1-continued

Exemplifying compounds of formula (I) according to the invention

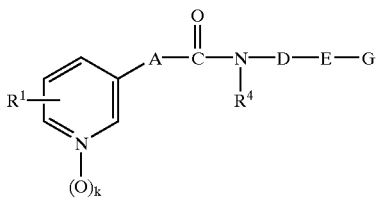

| Nr | R¹ | k | A | R⁴ | D-E-G |
|----|----|----|------|-----|-------|
| 158 | H | 0 | CH=CH | H | CH₂CH₂-[4-piperidinyl-2-one]-N-CH(C₆H₅)₂ |
| 159 | H | 0 | CH=CH | H | CH₂CH₂CH₂CH₂-[3-CH₃-4-piperidinyl]-N-CH(C₆H₅)₂ |
| 160 | H | 0 | CH=CH | H | CH₂CH₂CH₂CH₂-[3-CH₂OH-4-piperidinyl]-N-CH(C₆H₅)₂ |
| 161 | H | 0 | CH₂CH₂ | H | CH₂CH₂CH₂CH₂-[3-COOCH₃-4-piperidinyl]-N-CH(C₆H₅)₂ |
| 162 | H | 0 | CH₂CH₂ | H | CH₂CH₂CH₂CH₂-[4-piperidinyl-2-one]-N-CH(C₆H₅)₂ |
| 163 | H | 0 | CH=CH | H | CH₂CH₂CH₂CH₂-[3,5-di-CH₃-4-piperidinyl]-N-CH(C₆H₅)₂ |
| 164 | H | 0 | CH₂CH₂ | H | CH₂CH₂-[tropane]-N-CH(C₆H₅)₂ |

TABLE 1-continued

Exemplifying compounds of formula (I) according to the invention

| Nr | R¹ | k | A | R⁴ | D-E-G |
|---|---|---|---|---|---|
| 165 | H | 0 | CH=CH | H | CH₂CH₂-quinuclidine-N-CH(phenyl)₂ |
| 166 | H | 0 | CH₂CH₂CH₂CH₂ | H | CH₂CH₂CH₂CH₂-quinuclidine-N-CH(phenyl)₂ |
| 167 | H | 0 | CH₂CH₂ | H | CH₂-piperidine-N-CH(4-F-phenyl)₂ |
| 168 | H | 0 | CH₂CH₂ | H | CH₂CH₂-piperidine-N-CH(4-F-phenyl)₂ |

TABLE 1-continued

Exemplifying compounds of formula (I) according to the invention

| Nr | R¹ | k | A | R⁴ | D-E-G |
|---|---|---|---|---|---|
| 169 | H | 0 | CH=CH | H | CH₂CH₂-[4-piperidinyl-N-CH(4-F-C₆H₄)₂] |
| 170 | H | 0 | CH₂CHF | H | CH₂CH₂CH₂CH₂-[4-piperidinyl-N-CH(4-F-C₆H₄)₂] |
| 171 | H | 0 | CH=CH | H | CH₂CH₂CH₂CH₂-[4-piperidinyl-N-CH(4-F-C₆H₄)₂] |
| 172 | H | 1 | CH=CH | H | CH₂CH₂CH₂CH₂-[4-piperidinyl-N-CH(4-F-C₆H₄)₂] |

TABLE 1-continued
Exemplifying compounds of formula (I) according to the invention
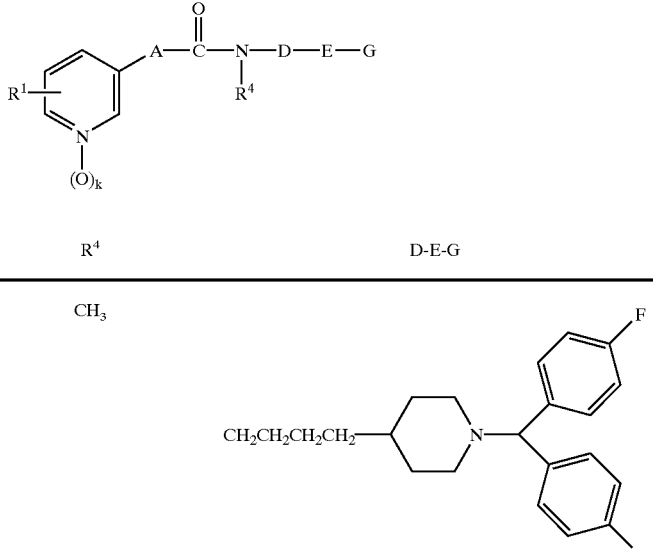
| Nr | R¹ | k | A | R⁴ | D-E-G |
|---|---|---|---|---|---|
| 173 | H | 0 | CH=CH | CH₃ | CH₂CH₂CH₂CH₂–[4-piperidinyl]–N–CH(4-F-C₆H₄)(4-F-C₆H₄) |
| 174 | H | 0 | CH=CH | H | CH₂CH₂CH₂CH₂CH₂–[4-piperidinyl]–N–CH(4-F-C₆H₄)(4-F-C₆H₄) |
| 175 | H | 0 | CH₂CH₂ | H | (CH₂)₅–[4-piperidinyl]–N–CH(4-F-C₆H₄)(4-F-C₆H₄) |
| 176 | H | 0 | CH₂CH₂ | H | CH₂CH₂–[4-piperidinyl]–N–CH(4-Cl-C₆H₄)(C₆H₅) |

TABLE 1-continued
Exemplifying compounds of formula (I) according to the invention
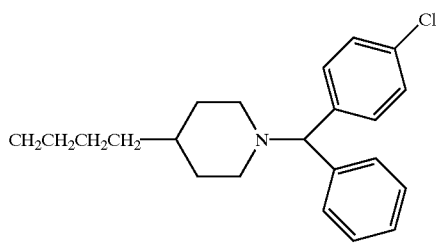
| Nr | R¹ | k | A | R⁴ | D-E-G |
|----|----|----|----|----|-------|
| 177 | H | 0 | CH=CH | H | 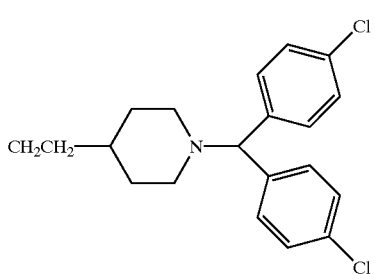 |
| 178 | H | 0 | CH=CH | H | |
| 179 | H | 0 | CH=CH | H | 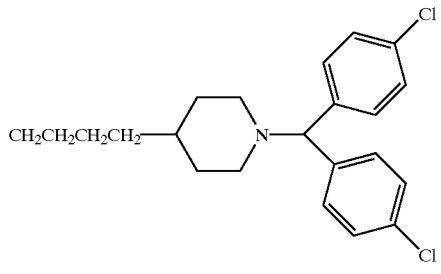 |
| 180 | H | 0 | CH=C(C₆H₅) | H | 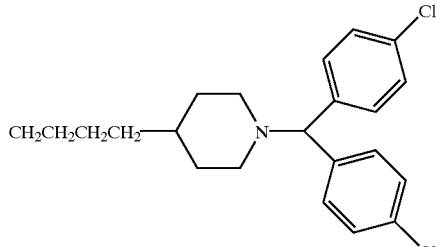 |

TABLE 1-continued

Exemplifying compounds of formula (I) according to the invention

| Nr | R¹ | k | A | R⁴ | D-E-G |
|---|---|---|---|---|---|
| 181 | H | 0 | CH$_2$CH$_2$ | H | CH$_2$CH$_2$-[4-piperidinyl]-N-CH(4-Cl-C$_6$H$_4$)(4-Cl-C$_6$H$_4$) |
| 182 | H | 0 | CH$_2$CH$_2$ | H | CH$_2$-[4-piperidinyl]-N-CH(2-Cl-C$_6$H$_4$)(2-Cl-C$_6$H$_4$) |
| 183 | H | 0 | CH=CH | H | CH$_2$CH$_2$-[4-piperidinyl]-N-CH(2-Cl-C$_6$H$_4$)(2-Cl-C$_6$H$_4$) |
| 184 | H | 0 | CH$_2$CH$_2$CH$_2$ | H | CH$_2$CH$_2$-[4-piperidinyl]-N-CH(2-Cl-C$_6$H$_4$)(2-Cl-C$_6$H$_4$) |
| 185 | H | 0 | CH$_2$CH$_2$ | H | CH$_2$CH$_2$CH$_2$CH$_2$-[4-piperidinyl]-N-CH(2-Cl-C$_6$H$_4$)(2-Cl-C$_6$H$_4$) |

TABLE 1-continued
Exemplifying compounds of formula (I) according to the invention
| Nr | R¹ | k | A | R⁴ | D-E-G |
|---|---|---|---|---|---|
| 186 | H | 0 | CH=CH | H | 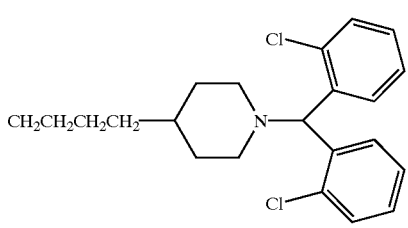 |
| 187 | H | 0 | CH₂CH₂CH₂CH₂ | H | 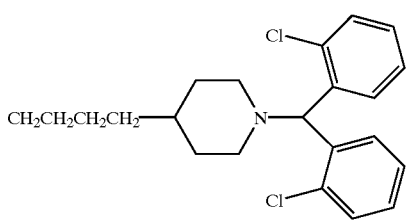 |
| 188 | H | 0 | CH=CH | H | 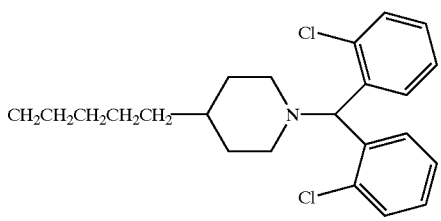 |
| 189 | H | 0 | CH₂CH₂ | H | 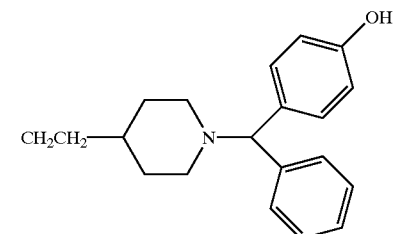 |
| 190 | H | 0 | CH=CH | H | 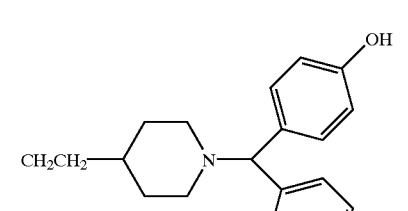 |

TABLE 1-continued
Exemplifying compounds of formula (I) according to the invention
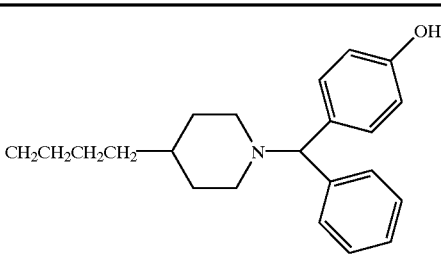
| Nr | R¹ | k | A | R⁴ | D-E-G |
|---|---|---|---|---|---|
| 191 | H | 0 | CH₂CH₂ | H | 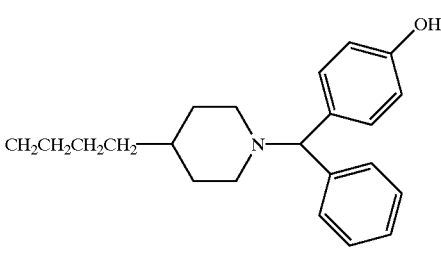 |
| 192 | H | 0 | CH=CH | H | |
| 193 | H | 0 | CH₂CH₂ | H | 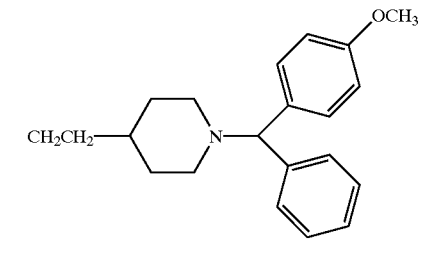 |
| 194 | H | 0 | CH=CH | H | 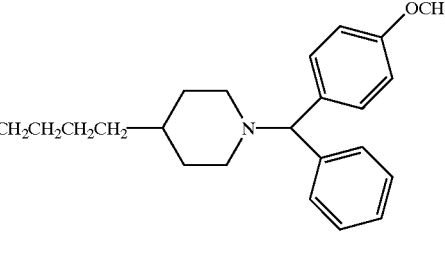 |
| 195 | H | 0 | CH₂CH₂ | H | 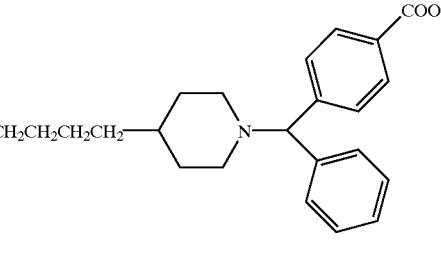 |

TABLE 1-continued

Exemplifying compounds of formula (I) according to the invention

| Nr | R¹ | k | A | R⁴ | D-E-G |
|---|---|---|---|---|---|
| 196 | H | 0 | CH$_2$CH$_2$ | H | CH$_2$CH$_2$-(4-piperidinyl)-N-C(phenyl)$_3$ |
| 197 | H | 0 | CH=CH | H | CH$_2$CH$_2$-(4-piperidinyl)-N-C(phenyl)$_3$ |
| 198 | H | 0 | CH=CH | H | CH$_2$CH$_2$CH$_2$CH$_2$-(4-piperidinyl)-N-C(phenyl)$_3$ |
| 199 | H | 0 | SCH$_2$CH$_2$ | H | CH$_2$CH$_2$CH$_2$CH$_2$-(4-piperidinyl)-N-C(phenyl)$_3$ |
| 200 | H | 0 | CH=CH | H | CH$_2$CH$_2$-(4-piperidinyl)-N-CH(phenyl)(3-pyridyl) |

TABLE 1-continued
Exemplifying compounds of formula (I) according to the invention
| Nr | R¹ | k | A | R⁴ | D-E-G |
|---|---|---|---|---|---|
| 201 | H | 0 | CH₂CH₂ | H | 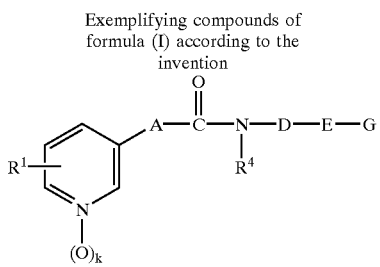 |
| 202 | H | 0 | CH₂CH₂ | H | 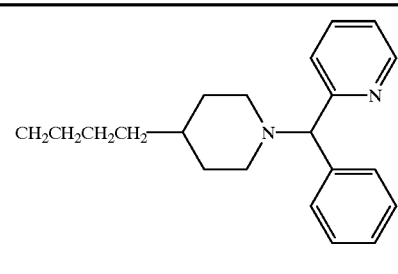 |
| 203 | H | 0 | CH₂CH₂CH₂CH₂ | H | 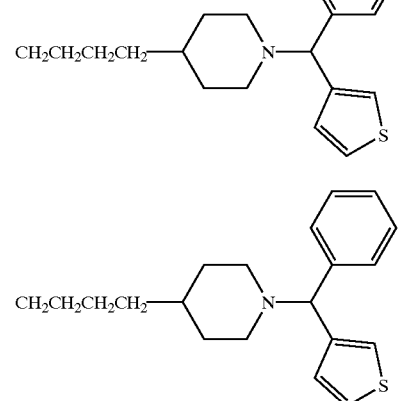 |
| 204 | H | 0 | CH₂CH₂ | H | 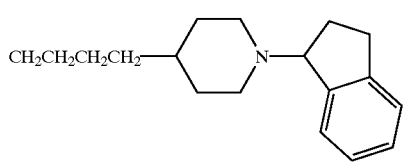 |
| 205 | H | 0 | CH=CH | H | 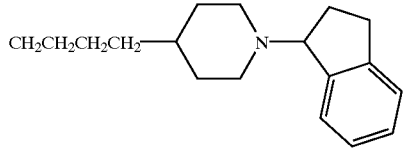 |
| 206 | H | 0 | CH₂CH₂ | H | 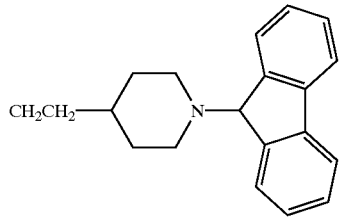 |

TABLE 1-continued

Exemplifying compounds of formula (I) according to the invention

| Nr | R¹ | k | A | R⁴ | D-E-G |
|---|---|---|---|---|---|
| 207 | H | 0 | CH=CH | H | CH₂CH₂-piperidine-N-(9H-fluoren-9-yl) |
| 208 | H | 0 | CH₂CH₂CH₂ | H | CH₂CH₂-piperidine-N-(9H-fluoren-9-yl) |
| 209 | H | 0 | CH₂CH₂ | H | CH₂CH₂CH₂CH₂-piperidine-N-(9H-fluoren-9-yl) |
| 210 | H | 0 | CH=CH | H | CH₂CH₂CH₂CH₂-piperidine-N-(9H-fluoren-9-yl) |
| 211 | H | 0 | CH₂CH₂ | H | CH₂CH₂CH₂CH₂CH₂-piperidine-N-(9H-fluoren-9-yl) |

TABLE 1-continued

Exemplifying compounds of formula (I) according to the invention

| Nr | R¹ | k | A | R⁴ | D-E-G |
|---|---|---|---|---|---|
| 212 | H | 0 | CH=CH | H | (CH₂)₆-[4-piperidinyl]-N-fluoren-9-yl |
| 213 | H | 0 | CH=CH | H | CH₂CH₂-[4-piperidinyl]-N-(9,10-dihydroanthracen-9-yl) |
| 214 | H | 0 | CH=CH | H | CH₂CH₂-[4-piperidinyl]-N-(10-oxo-9,10-dihydroanthracen-9-yl) |
| 215 | H | 0 | CH₂ | H | CH₂CH₂-[4-piperidinyl]-N-(10,11-dihydro-5H-dibenzo[a,d]cyclohepten-5-yl) |
| 216 | H | 0 | CH=CH | H | CH₂CH₂-[4-piperidinyl]-N-(10,11-dihydro-5H-dibenzo[a,d]cyclohepten-5-yl) |

TABLE 1-continued

Exemplifying compounds of formula (I) according to the invention

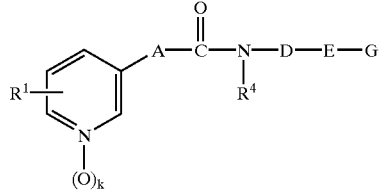

| Nr | R¹ | k | A | R⁴ | D-E-G |
|---|---|---|---|---|---|
| 217 | H | 0 | CH₂CH₂ | H | CH₂CH₂CH₂-piperidine-N-(10,11-dihydro-5H-dibenzo[a,d]cyclohepten-5-yl) |
| 218 | H | 0 | CH₂CH₂ | H | CH₂CH₂CH₂CH₂-piperidine-N-(10,11-dihydro-5H-dibenzo[a,d]cyclohepten-5-yl) |
| 219 | H | 0 | CH=CH | H | CH₂CH₂CH₂CH₂-piperidine-N-(10,11-dihydro-5H-dibenzo[a,d]cyclohepten-5-yl) |
| 220 | 6-F | 0 | CH=CH | H | CH₂CH₂CH₂CH₂-piperidine-N-(10,11-dihydro-5H-dibenzo[a,d]cyclohepten-5-yl) |
| 221 | H | 0 | CH₂CH₂ | H | (CH₂)₆-piperidine-N-(10,11-dihydro-5H-dibenzo[a,d]cyclohepten-5-yl) |

TABLE 1-continued
Exemplifying compounds of formula (I) according to the invention
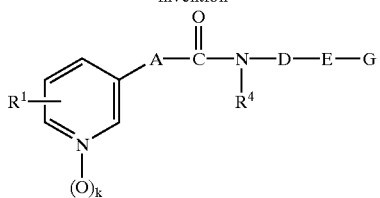
| Nr | R¹ | k | A | R⁴ | D-E-G |
|---|---|---|---|---|---|
| 222 | H | 0 | CH=CH | H | |
| 223 | H | 0 | CH₂CH₂ | H | |
| 224 | H | 0 | CH=CH | H | |
| 225 | H | 0 | CH=CH | H | |
| 226 | H | 0 | CH₂CH₂ | H | |

TABLE 1-continued

Exemplifying compounds of formula (I) according to the invention

| Nr | R¹ | k | A | R⁴ | D-E-G |
|----|----|----|------|----|-------|
| 227 | H | 0 | CH=CH | H | CH₂CH₂CH₂CH₂-[4-piperidinyl]-N-(7-methylthieno[3,2-d]pyrimidin-4-yl) |
| 228 | H | 0 | CH=CH | H | CH₂CH₂-[4-piperidinyl]-N-(5H-chromeno[2,3-b]pyridin-5-yl) |
| 229 | H | 0 | CH=CH | H | CH₂CH₂-[4-piperidinyl]-N-(4H,6H-thieno[2,3-c][2]benzothiepin-4-yl) |
| 230 | H | 0 | CH₂CH₂ | H | CH₂CH₂CH₂CH₂-[4-piperidinyl]-N-(6,11-dihydrodibenz[b,e]oxepin-11-yl) |
| 231 | H | 0 | CH=CH | H | CH₂CH₂CH₂CH₂-[4-piperidinyl]-N-(6,11-dihydrodibenz[b,e]oxepin-11-yl) |

TABLE 1-continued
Exemplifying compounds of formula (I) according to the invention
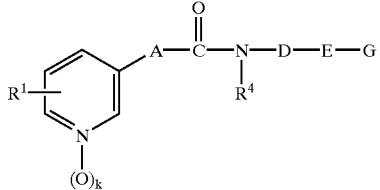
| Nr | R¹ | k | A | R⁴ | D-E-G |
|---|---|---|---|---|---|
| 232 | H | 0 | CH₂CH₂ | H | |
| 233 | H | 0 | CH=CH | H | |
| 234 | H | 0 | CH=CH | H | |
| 235 | H | 0 | CH₂CH₂ | H | |
| 236 | H | 0 | CH₂CH₂ | H | |

TABLE 1-continued
Exemplifying compounds of formula (I) according to the invention
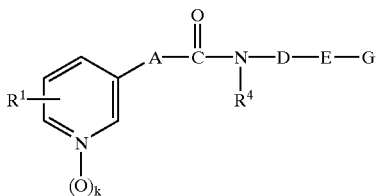
| Nr | R¹ | k | A | R⁴ | D-E-G |
|----|----|----|------|----|-------|
| 237 | H | 0 | CH=CH | H | |
| 238 | H | 0 | CH₂CH₂ | H | |
| 239 | H | 0 | CH=CH | H | |
| 240 | H | 0 | CH₂CH₂ | H | |
| 241 | H | 0 | CH=CH | H | |
| 242 | H | 0 | CH=CH | H | |
| 243 | H | 0 | CH=CH.CH=CH | H | |
| 244 | H | 0 | CH₂CH₂ | H | |

TABLE 1-continued

Exemplifying compounds of formula (I) according to the invention

| Nr | R¹ | k | A | R⁴ | D-E-G |
|---|---|---|---|---|---|
| 245 | H | 0 | CH=CH | H | CH₂CH₂CH₂CH₂-(4-piperidinyl)-C(=O)-cyclobutyl |
| 246 | H | 0 | CH=CH.CH=CH | H | CH₂CH₂CH₂CH₂-(4-piperidinyl)-C(=O)-cyclopentyl |
| 247 | H | 0 | CH₂CH₂ | H | CH₂CH₂-(4-piperidinyl)-C(=O)-CH₂CH₂-phenyl |
| 248 | H | 0 | CH=CH | H | CH₂CH₂-(4-piperidinyl)-C(=O)-CH₂CH₂-phenyl |
| 249 | H | 0 | CH₂CH₂CH₂ | H | CH₂CH₂-(4-piperidinyl)-C(=O)-CH₂-(1-naphthyl) |
| 250 | H | 0 | CH=CH | H | CH₂CH₂CH₂CH₂-(4-piperidinyl)-C(=O)-CH₂-(2-naphthyl) |
| 251 | H | 0 | CH₂CH₂ | H | CH₂CH₂-(4-piperidinyl)-C(=O)-CH(phenyl)₂ |
| 252 | H | 0 | CH=CH | H | CH₂CH₂CH₂CH₂-(4-piperidinyl)-C(=O)-CH(phenyl)₂ |

TABLE 1-continued
Exemplifying compounds of formula (I) according to the invention
| Nr | R¹ | k | A | R⁴ | D-E-G |
|---|---|---|---|---|---|
| 253 | H | 0 | CH=CH.CH=CH | H | 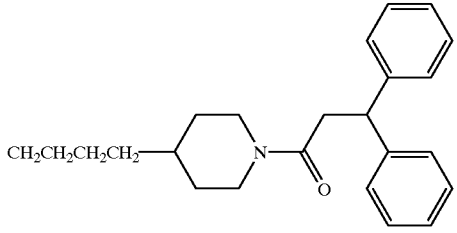 |
| 254 | H | 0 | CH=CH | H | 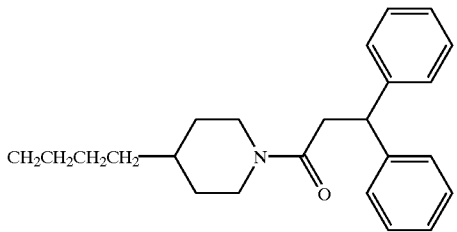 |
| 255 | H | 0 | CH₂CH₂CH₂ | H | 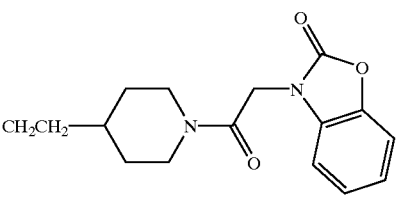 |
| 256 | H | 0 | CH₂CH₂ | H | 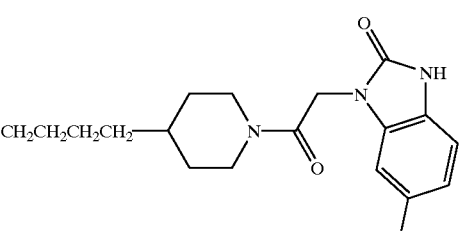 |
| 257 | H | 0 | CH=CH | H | 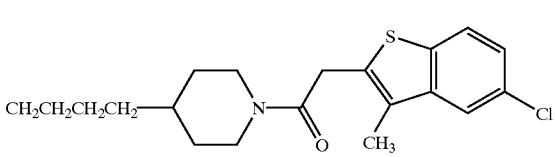 |
| 258 | H | 0 | CH₂CH₂ | H | 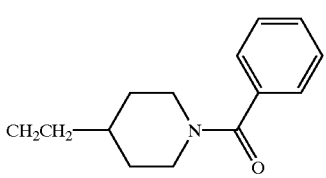 |

TABLE 1-continued

Exemplifying compounds of formula (I) according to the invention

| Nr | R¹ | k | A | R⁴ | D-E-G |
|---|---|---|---|---|---|
| 259 | H | 0 | CH=CH | H | CH₂CH₂CH₂CH₂-piperidine-N-C(=O)-phenyl |
| 260 | H | 0 | CH=CH.CH=CH | H | CH₂CH₂CH₂CH₂-piperidine-N-C(=O)-phenyl |
| 261 | H | 0 | CH₂CH₂ | H | CH₂CH₂CH₂CH₂-piperidine-N-C(=O)-(4-F-phenyl) |
| 262 | H | 0 | CH=CH | H | CH₂CH₂CH₂CH₂-piperidine-N-C(=O)-(4-F-phenyl) |
| 263 | H | 0 | CH₂CH₂ | H | CH₂CH₂CH₂CH₂-piperidine-N-C(=O)-(2,6-diCl-phenyl) |
| 264 | H | 0 | CH₂CH₂ | H | CH₂CH₂CH₂CH₂-piperidine-N-C(=O)-phenyl-C(=O)-phenyl |
| 265 | H | 0 | CH=CH | H | CH₂CH₂CH₂CH₂-piperidine-N-C(=O)-phenyl-C(=O)-phenyl |
| 266 | H | 0 | CH₂CH₂ | H | CH₂CH₂CH₂CH₂-piperidine-N-C(=O)-phenyl-C(=O)-phenyl |

TABLE 1-continued
Exemplifying compounds of formula (I) according to the invention
| Nr | R¹ | k | A | R⁴ | D-E-G |
|---|---|---|---|---|---|
| 267 | H | 0 | CH₂CH₂ | H |  |
| 268 | H | 0 | CH=CH | H | 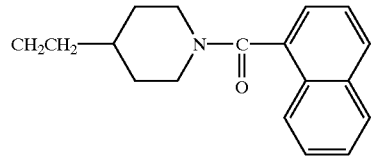 |
| 269 | H | 0 | CH₂CH₂ | H | 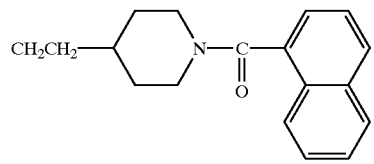 |
| 270 | H | 0 | CH₂CH₂ | H | 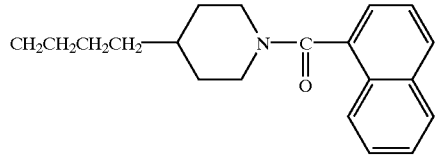 |
| 271 | H | 0 | CH=CH | H | 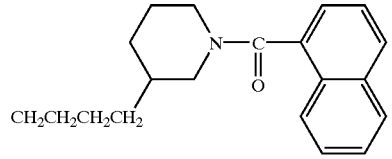 |
| 272 | H | 0 | CH₂CH₂ | H | 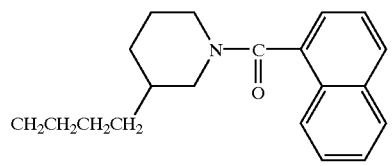 |
| 273 | H | 0 | CH=CH.CH=CH | H | 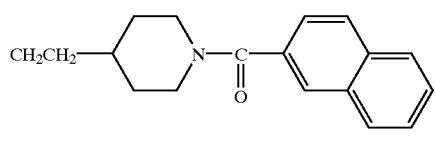 |
| 274 | H | 0 | CH₂CH₂ | H | 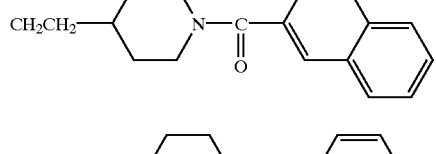 |

TABLE 1-continued
Exemplifying compounds of formula (I) according to the invention
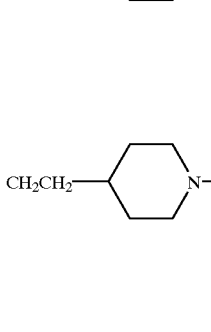
| Nr | R¹ | k | A | R⁴ | D-E-G |
|----|----|----|---|----|-------|
| 275 | H | 0 | CH$_2$CH$_2$ | H | |
| 276 | H | 0 | CH$_2$CH$_2$CH$_2$CH$_2$ | H | |
| 277 | H | 0 | CH=CH | H | |
| 278 | H | 0 | CH$_2$CH$_2$ | H | |
| 279 | H | 0 | CH=CH | H | |
| 280 | H | 0 | CH$_2$CH$_2$ | H | |
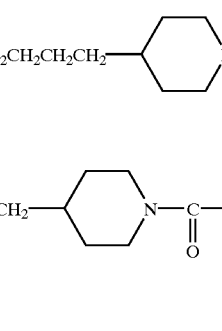
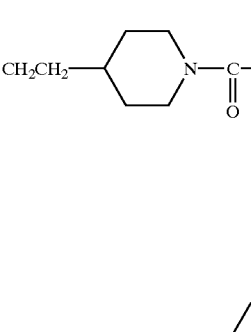

TABLE 1-continued
Exemplifying compounds of formula (I) according to the invention
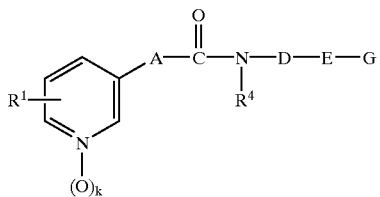
| Nr | R¹ | k | A | R⁴ | D-E-G |
|---|---|---|---|---|---|
| 281 | H | 0 | CH₂CH₂ | H | 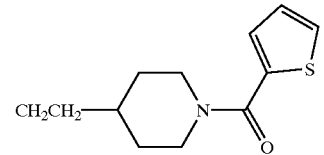 |
| 282 | H | 0 | CH=CH | H | 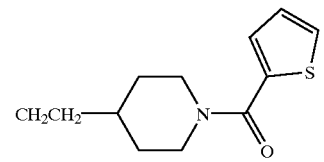 |
| 283 | H | 0 | CH=CH | H | 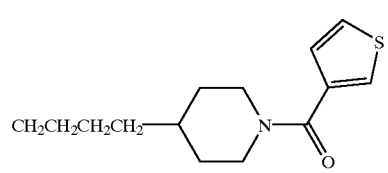 |
| 284 | H | 0 | CH₂CH₂CH₂CH₂ | H | 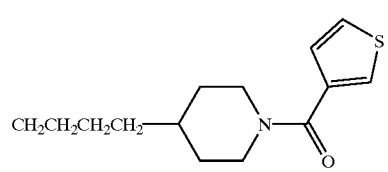 |
| 285 | H | 0 | CH₂CH₂ | H | 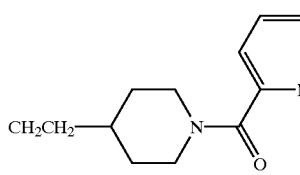 |
| 286 | H | 0 | CH=CH | H | 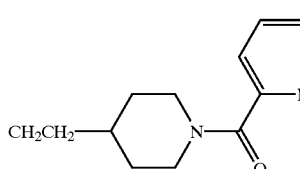 |
| 287 | H | 0 | CH₂CH₂ | H | 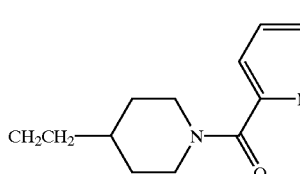 |

TABLE 1-continued
Exemplifying compounds of formula (I) according to the invention
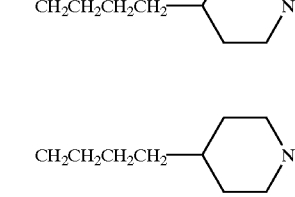
| Nr | R¹ | k | A | R⁴ | D-E-G |
|---|---|---|---|---|---|
| 288 | H | 0 | CH=CH | H | 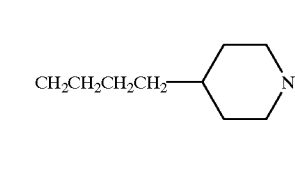 |
| 289 | H | 0 | CH₂CH₂ | H |  |
| 290 | H | 0 | CH=CH | H |  |
| 291 | H | 0 | CH=CH.CH=CH | H |  |
| 292 | H | 0 | CH=CH | H | 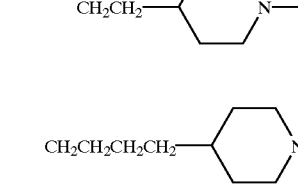 |
| 293 | H | 0 | CH=CH | H | 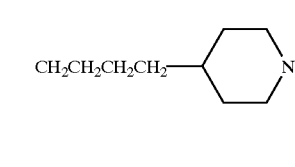 |
| 294 | H | 0 | CH₂CH₂ | H | 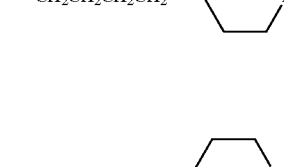 |
| 295 | H | 0 | 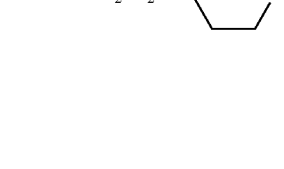 | H |  |
| 296 | H | 0 | CH₂CH₂ | H |  |

TABLE 1-continued

Exemplifying compounds of formula (I) according to the invention

| Nr | R¹ | k | A | R⁴ | D-E-G |
|---|---|---|---|---|---|
| 297 | H | 0 | CH₂CH₂ | H | CH₂CH₂CH₂CH₂-piperidine-C(O)-NH-CH₂-phenyl |
| 298 | H | 0 | CH=CH | H | CH₂CH₂CH₂CH₂-piperidine-C(O)-NH-CH₂-phenyl |
| 299 | H | 0 | CH=CH | H | CH₂CH₂CH₂CH₂-piperidine-C(O)-NH-CH₂-(naphth-2-yl) |
| 300 | H | 0 | CH₂CH₂ | H | CH₂CH₂CH₂CH₂-piperidine-C(O)-NH-CH₂-(anthracen-9-yl) |
| 301 | H | 0 | CH=CH | H | CH₂CH₂CH₂CH₂-piperidine-C(O)-NH-CH₂-(pyridin-3-yl) |
| 302 | H | 0 | CH₂CH₂ | H | CH₂CH₂CH₂CH₂-piperidine-C(O)-NH-(indan-1-yl) |
| 303 | H | 0 | CH=CH.CH=CH | H | CH₂CH₂CH₂CH₂-piperidine-C(O)-NH-(1,2,3,4-tetrahydronaphth-1-yl) |
| 304 | H | 0 | CH₂CH₂ | H | CH₂CH₂CH₂CH₂-piperidine-C(O)-NH-(indan-5-yl) |

TABLE 1-continued

Exemplifying compounds of formula (I) according to the invention

| Nr | R¹ | k | A | R⁴ | D-E-G |
|---|---|---|---|---|---|
| 305 | H | 0 | $CH_2CH_2$ | H | CH₂CH₂CH₂CH₂-piperidine-C(O)NH-naphthalen-1-yl |
| 306 | H | 0 | CH=CH | H | CH₂CH₂CH₂CH₂-piperidine-C(O)NH-(1,2,3,4-tetrahydronaphthalen-1-yl) |
| 307 | H | 0 | CH=CH | H | CH₂CH₂-piperidine-C(O)NH-anthracen-1-yl |
| 308 | H | 0 | $CH_2CH_2$ | H | CH₂CH₂CH₂CH₂-piperidine-C(O)NH-(9,10-dioxo-9,10-dihydroanthracen-2-yl) |
| 309 | H | 0 | CH=CH | H | CH₂CH₂CH₂CH₂-piperidine-C(O)N(CH₃)₂ |
| 310 | H | 0 | CH=CH | H | CH₂CH₂CH₂CH₂-piperidine-C(O)N(cyclohexyl)₂ |

TABLE 1-continued
Exemplifying compounds of formula (I) according to the invention
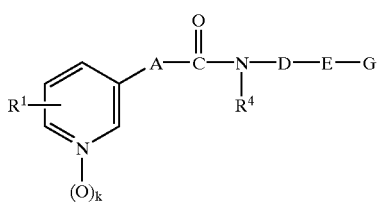
| Nr | R¹ | k | A | R⁴ | D-E-G |
|----|----|----|----|----|-------|
| 311 | H | 0 | CH₂CH₂ | H | CH₂CH₂CH₂CH₂–piperidine–C(O)–N(CH₂Ph)(CH₂Ph) |
| 312 | H | 0 | CH₂CH₂CH₂CH₂ | H | CH₂CH₂CH₂CH₂–piperidine–C(O)–N(CH₃)(Ph) |
| 313 | H | 0 | CH₂CH₂ | H | CH₂CH₂–piperidine–C(O)–N(Ph)(CH₂Ph) |
| 314 | H | 0 | CH=CH | H | CH₂CH₂–piperidine–C(O)–N(Ph)(CH₂Ph) |
| 315 | H | 0 | CH=CH | H | CH₂CH₂CH₂CH₂–piperidine–C(O)–N(Ph)(Ph) |

TABLE 1-continued

Exemplifying compounds of formula (I) according to the invention

| Nr | R¹ | k | A | R⁴ | D-E-G |
|---|---|---|---|---|---|
| 316 | H | 0 | CH=CH.CH=CH | H | CH₂CH₂CH₂CH₂-piperidine-C(O)-N(phenyl)₂ |
| 317 | H | 0 | CH₂CH₂ | H | CH₂CH₂CH₂CH₂-piperidine-C(O)-azepane |
| 318 | H | 0 | C≡C | H | CH₂CH₂CH₂CH₂-piperidine-C(O)-indoline |
| 319 | H | 0 | CH₂CH₂CH₂ | H | CH₂CH₂CH₂CH₂-piperidine-C(O)-indoline |
| 320 | H | 0 | CH₂CH₂ | H | CH₂CH₂CH₂CH₂-piperidine-C(O)-tetrahydroquinoline |
| 321 | H | 0 | CH=CH | H | CH₂CH₂CH₂CH₂-piperidine-C(O)-tetrahydroquinoline |
| 322 | H | 0 | CH=CH | H | CH₂CH₂-piperidine-C(O)-tetrahydrobenzazepine |

TABLE 1-continued

Exemplifying compounds of formula (I) according to the invention

| Nr | R¹ | k | A | R⁴ | D-E-G |
|---|---|---|---|---|---|
| 323 | H | 0 | CH=CH | H | CH₂CH₂CH₂CH₂-piperidine-N-C(O)-carbazole |
| 324 | H | 0 | CH₂CH₂ | H | CH₂CH₂CH₂CH₂-piperidine-N-C(O)-(10,11-dihydrodibenzazepine) |
| 325 | H | 0 | CH₂CH₂CH₂CH₂ | H | CH₂CH₂CH₂CH₂-piperidine-N-C(O)-(10,11-dihydrodibenzazepine) |
| 326 | H | 0 | CH₂NCH₂CH₂ (N-SO₂CH₃) | H | CH₂CH₂-piperidine-N-SO₂-CH₃ |
| 327 | H | 0 | CH₂CH₂ | H | CH₂CH₂CH₂CH₂-piperidine-N-SO₂-CH₂CH₃ |
| 328 | H | 0 | CH₂CH₂ | H | CH₂CH₂-piperidine-N-SO₂-phenyl |
| 329 | H | 0 | CH₂CH₂CH₂ | H | CH₂CH₂CH₂CH₂-piperidine-N-SO₂-phenyl |
| 330 | H | 0 | CH=CH | H | CH₂CH₂CH₂CH₂-piperidine-N-SO₂-(4-Br-phenyl) |
| 331 | H | 0 | CH=CH | H | (CH₂)₆-piperidine-N-SO₂-(4-CH₃-phenyl) |

TABLE 1-continued

Exemplifying compounds of formula (I) according to the invention

| Nr | R¹ | k | A | R⁴ | D-E-G |
|---|---|---|---|---|---|
| 332 | H | 0 | CH₂CH₂ | H | CH₂CH₂-piperidine-N-SO₂-(1-naphthyl) |
| 333 | H | 0 | CH₂CH₂ | H | CH₂CH₂CH₂CH₂-piperidine-N-SO₂-(1-naphthyl) |
| 334 | H | 0 | OCH₂ | H | CH₂CH₂CH₂CH₂-piperidine-N-SO₂-(1-naphthyl) |
| 335 | H | 0 | CH₂CH₂CH₂ | H | CH₂-piperidine-N-SO₂-(2-naphthyl) |
| 336 | H | 0 | CH₂CH₂ | H | CH₂CH₂-piperidine-N-SO₂-(2-naphthyl) |
| 337 | H | 0 | CH₂CH₂ | H | CH₂CH₂CH₂CH₂-piperidine-N-SO₂-(2-naphthyl) |
| 338 | H | 0 | CH=CH | H | CH₂CH₂CH₂CH₂-piperidine-N-SO₂-(2-naphthyl) |
| 339 | H | 0 | CH₂CH₂CH₂CH₂ | H | CH₂CH₂CH₂CH₂-piperidine-N-SO₂-(2-naphthyl) |

TABLE 1-continued

Exemplifying compounds of formula (I) according to the invention

| Nr | R¹ | k | A | R⁴ | D-E-G |
|----|----|----|----|----|-------|
| 340 | H | 0 | CH₂CH₂ | H | CH₂CH₂CH₂CH₂–[piperidine]–N–SO₂–[2-thienyl] |
| 341 | H | 0 | CH₂CH₂ | H | CH₂CH₂CH₂CH₂–[piperidine]–N–SO₂–[3,5-dimethylisoxazol-4-yl] |
| 342 | H | 0 | CH=CH | H | CH₂CH₂CH₂CH₂–[piperidine]–N–SO₂–[3,5-dimethylisoxazol-4-yl] |
| 343 | H | 0 | CH₂CH₂ | H | CH₂CH₂CH₂CH₂–[piperidine]–N–SO₂–[2,1,3-benzothiadiazol-4-yl] |
| 344 | H | 0 | CH=CH | H | CH₂CH₂CH₂CH₂–[piperidine]–N–SO₂–[2,1,3-benzothiadiazol-4-yl] |
| 345 | H | 0 | CH₂CH₂ | H | CH₂CH₂CH₂CH₂–[piperidine]–N–SO₂–[5-chloro-3-methylbenzothiophen-2-yl] |
| 346 | H | 0 | △ | H | (CH₂)₆–[piperidine]–N–SO₂–[5-chloro-3-methylbenzothiophen-2-yl] |
| 347 | H | 0 | CH=CH | H | (CH₂)₆–[piperidine]–N–SO₂–[5-chloro-3-methylbenzothiophen-2-yl] |

TABLE 1-continued
Exemplifying compounds of formula (I) according to the invention
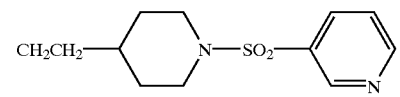
| Nr | R¹ | k | A | R⁴ | D-E-G |
|---|---|---|---|---|---|
| 348 | H | 0 | CH₂CH₂ | H | 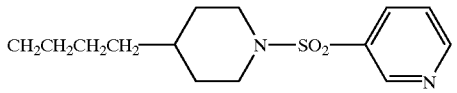 |
| 349 | H | 0 | CH₂CH₂CH₂CH₂ | H | 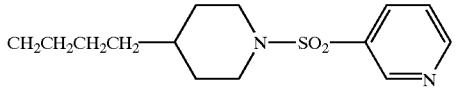 |
| 350 | H | 0 | CH═CH | H | 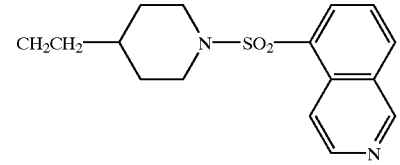 |
| 351 | H | 0 | CH═CH | H | 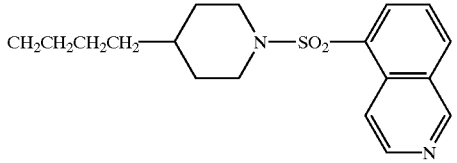 |
| 352 | H | 0 | CH₂CH₂ | H | 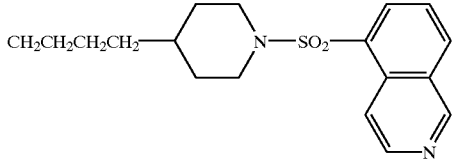 |
| 353 | H | 0 | CH═CH | H | 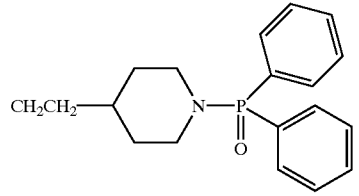 |
| 354 | H | 0 | CH₂CH₂ | H | 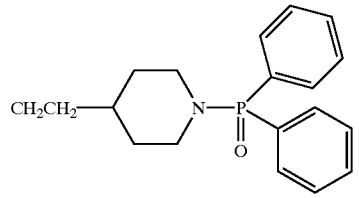 |
| 355 | H | 0 | CH═CH—CH═CH | H | |

TABLE 1-continued

Exemplifying compounds of formula (I) according to the invention

| Nr | R¹ | k | A | R⁴ | D-E-G |
|---|---|---|---|---|---|
| 356 | H | 0 | CH₂CH₂ | H | CH₂CH₂CH₂CH₂-piperidine-N-P(=O)(phenyl)₂ |
| 357 | H | 0 | CH=CH | H | CH₂CH₂CH₂CH₂-piperidine-N-P(=O)(phenyl)₂ |
| 358 | H | 0 | CH₂CH₂ | H | CH₂CH₂-piperidine-N-C(=O)CF₃ |
| 359 | H | 0 | CH=CH | H | CH₂CH₂-piperidine-N-C(=O)CF₃ |
| 360 | H | 0 | CH=CH | H | CH₂CH₂CH₂CH₂-piperidine-N-C(=O)OCH₂CH₃ |
| 361 | H | 0 | CH=CH.CH=CH | H | CH₂CH₂CH₂CH₂-piperidine-N-C(=O)OCH₂CH₃ |
| 362 | H | 0 | CH=CH.CH=CH | H | CH₂CH₂CH₂CH₂-piperidine-N-C(=O)O-CH₂CH=CH₂ |
| 363 | H | 0 | CH=CH | H | CH₂-piperidine-N-C(=O)O-C(CH₃)₃ |
| 364 | H | 0 | cyclopropyl | H | CH₂CH₂-piperidine-N-C(=O)O-C(CH₃)₃ |

TABLE 1-continued

Exemplifying compounds of formula (I) according to the invention

| Nr | R¹ | k | A | R⁴ | D-E-G |
|---|---|---|---|---|---|
| 365 | H | 0 | C≡C | H | CH₂CH₂-piperidine-N-C(O)-O-C(CH₃)₃ |
| 366 | H | 0 | (CH₂)₂CH=CH | H | CH₂CH₂-piperidine-N-C(O)-O-C(CH₃)₃ |
| 367 | H | 0 | CH=CH | H | CH₂CH₂CH₂CH₂-piperidine-N-C(O)-O-C(CH₃)₃ |
| 368 | H | 0 | CH=CH.CH=CH | H | CH₂CH₂CH₂CH₂-piperidine-N-C(O)-O-C(CH₃)₃ |
| 369 | H | 0 | CH=CH | H | CH₂CH₂CH₂CH₂CH₂-piperidine-N-C(O)-O-C(CH₃)₃ |
| 370 | H | 0 | CH=CH | H | (CH₂)₆-piperidine-N-C(O)-O-C(CH₃)₃ |
| 371 | H | 0 | CH=CH | H | CH₂CH₂CH₂CH=piperidine-N-C(O)-O-C(CH₃)₃ |
| 372 | H | 0 | CH=CH.CH=CH | H | CH₂CH=CHCH₂-piperidine-N-C(O)-O-C(CH₃)₃ |

TABLE 1-continued
Exemplifying compounds of formula (I) according to the invention
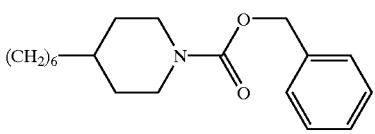
| Nr | R¹ | k | A | R⁴ | D-E-G |
|---|---|---|---|---|---|
| 373 | H | 0 | $CH_2CH_2$ | H | 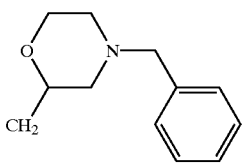 |
| 374 | H | 0 | $CH_2CH_2$ | H | 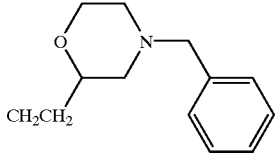 |
| 375 | H | 0 | CH=CH | H | 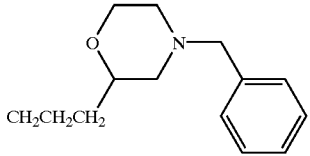 |
| 376 | H | 0 | CH=CH | H | 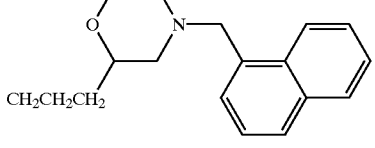 |
| 377 | H | 0 | $CH_2CH_2$ | H | 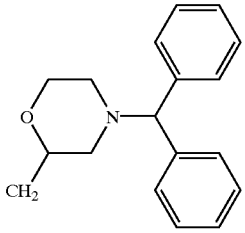 |
| 378 | H | 0 | CH=CH | H | |

TABLE 1-continued

Exemplifying compounds of formula (I) according to the invention

| Nr | R¹ | k | A | R⁴ | D-E-G |
|---|---|---|---|---|---|
| 379 | H | 0 | CH=CH | H | (2-(CH₂CH₂)-morpholin-4-yl)-CH(phenyl)(pyridin-3-yl) |
| 380 | H | 0 | CH=CH.CH=CH | H | (2-(CH₂CH₂)-morpholin-4-yl)-C(=O)-naphth-2-yl |
| 381 | H | 0 | CH=CH | H | (2-(CH₂CH₂)-morpholin-4-yl)-C(=O)-N(phenyl)₂ |
| 382 | H | 0 | CH=CH | H | (2-(CH₂CH₂CH₂)-morpholin-4-yl)-SO₂-naphth-2-yl |
| 383 | H | 0 | CH₂CH₂ | H | (4-(CH₂CH₂CH₂)-azepan-1-yl)-CH₂-phenyl |
| 384 | H | 0 | CH=CH | H | (4-(CH₂CH₂CH₂)-azepan-1-yl)-CH₂-phenyl |

TABLE 1-continued
Exemplifying compounds of formula (I) according to the invention
| Nr | R¹ | k | A | R⁴ | D-E-G |
|---|---|---|---|---|---|
| 385 | H | 0 | CH₂CH₂ | H | 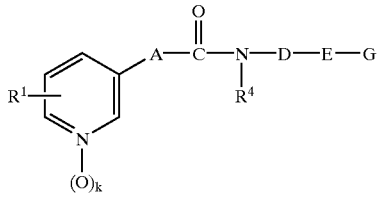 |
| 386 | H | 0 | CH=CH | H | 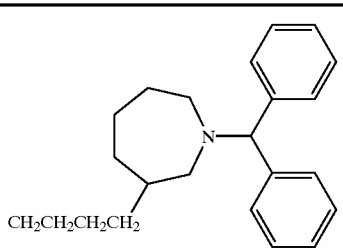 |
| 387 | H | 0 | CH₂CH₂ | H | 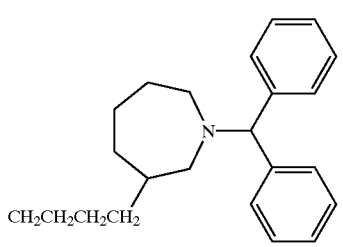 |
| 388 | H | 0 | CH₂CH₂ | H | 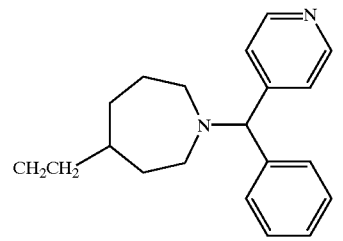 |
| 389 | H | 0 | CH=CH | H | 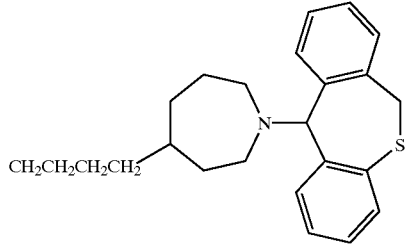 |

TABLE 1-continued

Exemplifying compounds of formula (I) according to the invention

| Nr | R¹ | k | A | R⁴ | D-E-G |
|---|---|---|---|---|---|
| 390 | H | 0 | CH=CH | H | (azepane with CH₂CH₂CH₂CH₂ linker, N–C(=O)–CH(phenyl)(phenyl)) |
| 391 | H | 0 | CH₂CH₂ | H | (azepane with CH₂CH₂ linker, N–C(=O)–phenyl) |
| 392 | H | 0 | CH=CH | H | (azepane with CH₂CH₂CH₂CH₂ linker, N–C(=O)–NH–2-naphthyl) |
| 393 | H | 0 | CH₂CH₂ | H | (azepane with CH₂CH₂CH₂CH₂ linker, N–SO₂–2-naphthyl) |
| 394 | H | 0 | CH₂CH₂ | H | (1,4-oxazepane with CH₂ substituent, N–CH₂–2-naphthyl) |
| 395 | H | 0 | CH=CH | H | (1,4-oxazepane with CH₂CH₂ substituent, N–CH₂CH₂–phenyl) |
| 396 | H | 0 | CH₂CH₂ | H | (1,4-oxazepane with CH₂CH₂ substituent, N–CH(2-thienyl)(phenyl)) |

TABLE 1-continued

Exemplifying compounds of formula (I) according to the invention

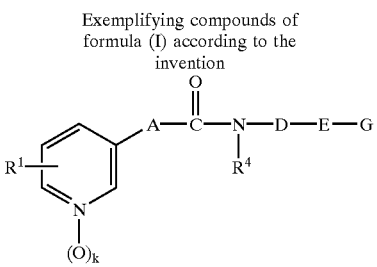

| Nr | R¹ | k | A | R⁴ | D-E-G |
|---|---|---|---|---|---|
| 397 | H | 0 | CH=CH | H | 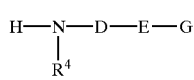 |

Various modes for synthesis of compounds used according to the invention are described in the following for reasons of simplifying reproducability.

Aside from a few exceptions, the optionally combined compounds presently described and used according to the invention are not previously described in the literature. A smaller portion of these compounds overlaps various previously known generic formulae that are very generally defined with respect to structure and which were named at the beginning as prior art. The synthesis methods for the production of the presently used compounds are entirely known to the person skilled in the art either generally from the relevant literature and/or from the prior art publications named at the beginning, also see the literature information referred to below. Consequently, the presently used compounds of the synthesis encompassed by the defined generic formula are easily accessible by analogous methods, as they are described, for example, in the following.

Method (A):

Compounds of formula (I) are obtained by reacting carboxylic acids of formula (II)

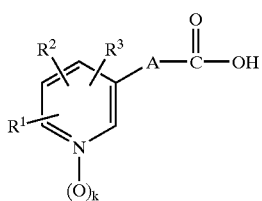

(II)

in which R¹, R², R³, A and k have the meaning given above or their reactive derivatives are reacted with compounds of formula (III)

H—N—D—E—G
    |
    R⁴

(III)

wherein D, E, G and R⁴ have the above meanings.

Reactive derivatives of compound (II) can be present, for example, as activated esters, anhydrides, acid halides, especially acid chlorides, or simple low alkyl esters. Suitable activated esters are, for example, p-nitrophenyl ester, 2,4,6-trichlorphenyl ester, pentachlorophenyl ester, cyanomethyl ester, esters of N-hydroxysuccinimide, of N-hydroxyphthalimides, of 1-hydroxybenzotriazol, of N-hydroxypiperidine, of 2-hydroxypyridine or of 2-mercaptopyridine, etc. Anhydrides can be symmetric anhydrides or mixed, as they are obtained, for example, with pivaloyl chloride or with chloroformates. Aromatic (for example chloroformic phenyl ester), araliphatic (for example chloroformic benzyl ester) or aliphatic chloroformates (for example chloroformic methyl ester and/or corresponding -ethyl or -isobutyl ester) can be used for this.

Reaction of compounds (II) with compounds (III) can also be carried out in the presence of condensation agents such as dicyclohexylcarbodiimide, 1-ethyl-3-(3-dimethylaminopropyl)carbodiimide hydrochloride, N,N'-carbonyldiimidazol, 1-ethoxycarbonyl-2-ethoxy-1,2-dihydroquinoline, etc. If carbodiimides are used as the condensation agent, reagents such as N-hydroxysuccinimide, N-hydroxyphthalimide, 1-hydroxybenzotriazol, N-hydroxypiperidine, etc. can be advantageously added.

Compounds of formula (III) can be used for reaction as free bases as well as in the form of their acid addition salts. For this, the salts of inorganic acids are to be preferred, i.e. hydrochlorides, hydrobromides or sulfates.

Reaction of compounds (II) or their reactive derivatives with compounds (III) are normally carried out in a suitable, preferably inert solvent. As examples, aromatic hydrocarbons such as benzene, toluol, xylene, halogenated hydrocarbons (for example dichloromethane, chloroform, 1,2-dichloroethane, trichloroethylene), ethers (for example diethyl ether, tetrahydrofuran, dioxane, glycol dimethyl ether), ethyl acetate, acetonitrile or polar aprotic solvents such as, for example, dimethylsulfoxide, dimethylformamide or N-methylpyrrolidone are to be named. Pure solvents, as well as mixtures of two or more can be used.

The reaction is optionally carried out in the presence of an auxiliary base. Suitable examples for this are alkali metal carbonates (sodium carbonate, potassium carbonate), alkali metal hydrogen carbonates (sodium hydrogen carbonate, potassium hydrogen carbonate), or organic bases such as, for example, triethylamine, ethyl diisopropylamine, tributylamine, N-methylmorpholine or pyridine. A suitable excess of compound (III) can also be used as a base. If compounds (III) are used in form of their acid addition salts, then it is appropriate to consider the amount of auxiliary base used as equivalent.

The reaction temperatures can—depending on reactivity of the educts—vary in a wide range. Generally the reaction is carried out at temperatures between −40° C. and 180° C. preferable between −10° C. and 130° C., especially at the boiling point of the solvent used.

The starting compounds (II) and (III) are known and/or can be produced according to known methods in an analogous manner. Moreover, the production of representative examples is further described below.

Method (B)

Compounds of formula (I) can be produced by reaction of compounds of formula (I), wherein G is hydrogen and which themselves possess the above-named pharmacological activities such as a cytostatic and/or immunomodulatory activity, as intermediate products as well as end products, with a compound of formula (IV).

$$L\text{—}G \qquad (IV)$$

in which G has the meaning given above, with the exception of hydrogen, and L is a suitable nucleofuge or reactive group. The type of nucleofuge or reactive group L and the conditions of the reaction are dependent of the nature of group G.

Method (B1)

Compounds of formula (I), in which G, with the exception of hydrogen, has the meaning of (G1) according to the above definition can, aside from method (a), also be produced by reacting compounds of formula (I), wherein G is hydrogen, with a suitable alkylation agent and/or arylation agent of formula (IV), wherein G is an alkyl-, alkenyl-, alkinyl-, cycloalkyl-, aryl-, aralkyl-, heteroaryl- or heteroaralkyl residue according to definition and the leaving group L can be a reactive derivative of an alkohol, for example, a halogen atom such as chlorine, bromine or iodine or a sulfonic acid ester, i.e. for example a methanesulfonyloxy-, trifluoromethanesulfonyloxy-, ethanesulfonyloxy-, benzenesulfonyloxy-, p-toluolsulfonyloxy-, p-bromobenzenesulfonyloxy- or m-nitrobenzenesulfonyloxy residue, etc. A reactive group L can be a terminal epoxide group for example.

The reaction of compounds (I), in which G is a hydrogen, and (IV) is usually conducted in a suitably inert solvent. Such solvents can be, for example, aromatic hydrocarbons (benzene, toluol, xylene), ethers (for example tetrahydrofuran, dioxane, glycol dimethyl ether), ethyl acetate, acetonitrile, ketones (acetone, ethyl methyl ketone), polar protic solvents such as alcohols (ethanol, isopropanol, butanol, glycol monomethyl ether) or polar aprotic solvents such as, for example, dimethylsulfoxide, dimethylformamide or N-methylpyrrolidone. Pure solvents as well as mixtures of two or more can also be used. Preferably, the reactions are carried out in the presence of bases, whereby said bases can be used as in method (a) above If chlorides or bromides are used as compound (IV), the reaction can be accelerated by the addition of alkali metal iodides (sodium iodide, potassium iodide). The reaction temperatures can vary between 0° C. and 180° C. depending on the reactivity of the educts, but preferable lie between 20° C. and 130° C.

Method (B2)

Compounds of formula (I), in which G represents an acyl residue, a carbamoyl residue, a sulfonyl residue or a phosphinoyl residue according to the above definition, can also be produced, aside from the above method (a), by reacting compounds of formula (I), in which G is hydrogen, with a carboxylic acid, carbamic acid. sulfonic acid and/or phosphinic acid of formula (V), in which G is an acyl residue, carbamoyl residue, sulfonyl residue or phosphinoyl residue according to definition, $$HO\text{—}G \qquad (V)$$

or their derivatives capable of reaction. Preferred derivatives of carboylic acids and/or sulfonic acids (V) which are capable of reaction are symmetric or unsymmetric carboxylic acid anhydrides and/or sulfonic acid anhydrides or acyl- and/or sulfonyl halides, especially acyl- and/or sulfonyl chlorides. Preferably, derivatives of carbamates and/or phosphinic acids which are capable of reaction are the carbamoyl halides and/or phosphinyl halides, especially carbamyl- and/or phosphinyl chlorides. The reaction of the acids (V) and/or their reactive derivatives with compounds (I), in which G is hydrogen, preferably occurs in the presence of auxiliary bases in solvents and under conditions as they are described in method (A).

Method (B3)

Compounds of formula (I), in which G represents a carbamoyl residue according to the definition G2 with r=0. i.e. the group

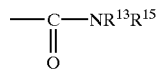

can also be produced, aside from the methods (A) and (B2), by reacting compounds of formula (I), in which G is hydrogen with a carbonyl group transmitter to an intermediate product and subsequently reacting this directly with a primary or secondary amine with the formula (VI)

$$H\text{—}NR^{13}R^{15} \qquad (VI)$$

in which $R^{13}$ and $R^{15}$ and/or the group —$NR^{13}R^{15}$ have the meanings according to the above definitions without having to purify or isolate the intermediate product. Trichloromethylcarbonate (triphosgene) and carbonyldiimidazol have been proven as particularly reactive carbonyl group transmitters. The reaction of compounds of formula (I), wherein G is hydrogen, with triphosgere and/or carbonyldiimidazol are typically conducted in an absolute, inert solvent in the presence of a tertiary, organic amine as an auxiliary base in such a manner that the solution of compounds (I) and the auxiliary base are slowly poured into a solution of an equivalent amount of carbonyl group transmitter. Thereby, the reaction requires molar ratios of 1:1 for the reaction of compound (I) and carbonyldiimidazol, and, in contrast, a ratio of 1:0.35 for the use of triphosgene. After complete reaction of the components to the intermediate product, compound (VI) is added in stochiometric amounts or in excess as a solution or a solid and the reaction is tropically completed at elevated temperature. Suitable inert solvents are, for example hydrocarbons such as hexane, heptane, benzene, toluol, xylene, chlorinated hydrocarbons (for example dichloromethane, chloroform, 1,2-dichloroethane, trichloroethylene), ethers (for example diethyl ether, tetrahydrofuran, dioxane), esters such as ethyl acetate, butyl acetate, acetonitrile or polar aprodic solvents such as formamide or dimethylformamide. Pure solvents as well as mixtures can be used diversely. Sometimes it is of advantage to carry out the first partial reaction at low temperature in a low-viscosity, highly-volatile solvent and to remove the solvent after formation of the intermediate and replace it by a higher boiling solvent. Amines such as for example triethylamine, ethyl diisopropylamine, tributylamine, N-methylmorpholine or pyridine are suitable as auxiliary bases. If compounds (I) or (VI) are used as salts, the amount of the auxiliary base is increased accordingly. The reaction temperatures can lie in between −40° C. and 50° C. for the first partial reaction, preferably at 0° C. bis 30° C., and between 0° C. and 150° C. for the second partial reaction, preferably at 20° C. bis 120° C.

Method (B4)

Compounds of formula (I), in which G represents a carbamoyl residue according to the definition G2 with r=0 and $R^{15}$=hydrogen, i.e. a group

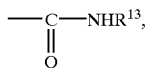

can also be produced. aside from methods A, B2 and B3, by reacting the compounds of formula (I) in which G is hydrogen, with an isocyanate of formula (VII) in which $R^{13}$ has the meaning according to the above definition $$O=C=N-R^{13} \qquad (VII)$$

Reaction of the compounds of formula (I), in which G is hydrogen, with the isocyanates of formula (VII) are conducted thereby in an absolute, inert solvent which can be a hydrocarbon such as pentane, hexane, heptane, benzene, toluol, or xylene, chlorinated hydrocarbons (such as dichloromethane, chloroform, 1,2-dichloroethane, trichloroethylene), ethers (for example, diethyl ether, tetrahydrofuran, dioxane), esters such as ethyl acetate, butyl acetate, or polar aprotic solvents such as formamide or dimethylformamide. Mixtures of various solvents can also be used. Thereby, the reaction temperatures can vary, in the region from −20° C. to 150° C., but preferably lie at 20° C. to 100° C.

The above-named intermediate products in the form of compounds according to formula (I), wherein G is hydrogen, which have the above-mentioned activities, such as for example a cytostatic activity in an analogous way to the end products themselves, are suitable for the production of a multitude of end products through the synthesis methods B1–B4.

They themselves can, in principle, be produced according to method A by reacting a carboxylic acid of formula (II) with amines of formula (III) in which G is hydrogen as described above. However, since the compounds of formula (III) with hydrogen as G represent α,ω-diamines, the formation of product mixtures is always to be expected in their reaction with carboxylic acids (II) or their reactive derivatives making a subsequent separation necessary.

In contrast, compounds of formula (I), in which G is hydrogen, are essentially more advantageously produced from other compounds of formula (I), in which G is a selectively cleavable group under mild conditions, i.e. corresponds to a nitrogen protective group.

Among the compounds according to formula (I) with tumor growth inhibiting properties, compounds are particularly suitable for this in which G represents a benzyl group, a 4-methoxybenzyl group, a diphenylmethyl croup, a triphenylmethyl group, a benzloxycarbonyl group, a methoxy- and/or ethoxycarbonyl group, a tert-butoxycarbonyl group, an allyloxycarbonyl group or a trifluoroacetyl group. For example, compounds according to formula (I) with benzyl, diphenylmethyl, triphenylmethyl or benzyloxycarbonyl groups can already be catalytically transformed into the compounds of formula (I) with hydrogen as G at room temperature under mild conditions with elementary hydrogen or by transfer hydration. Compounds of formula (I) with a 4-methoxylbenzyl group are transformed into compounds of formula (I) with hydrogen as G by selective oxidation with ammonium-cer(IV)-nitrate. The cleavage of simple alkoxycarbonyl groups such as the methoxy- or ethoxycarbonyl group as well as the trifluoroacetyl group as G in compounds of formula (I) succeed by alkali hydrolysis under mild conditions without cleaning the A and D linked amide function. This is suitably valid for the cleavage of the triphenylmethyl group and the tert-butoxycarbonyl group as G in compounds of formula (I), which occurs in acidic medium under mild conditions. Finally compounds of formula (I) with an allyloxycarbonyl group as G can be converted into such with hydrogen as G in neutral medium with palladium catalyst. All these methods are fully familiar to the person skilled in the art, and are furthermore also documented in monographs (see for example Greene, Wuts, Protective Groups in Organic Synthesis, New York, 1991).

Method C

Compounds of formula (I), in which $R^4$ is an alkyl, alkenyl, alkinyl or cycloalkyl residue according to the above definition can also be produced, aside from the methods A and B, by reacting compounds of formula (I), in which $R^4$ is hydrogen, with a suitable alkylation agent of formula (VIII)

$$L-R^4 \qquad (VIII)$$

in which $R^4$ is an alkyl, alkenyl, alkinyl or cycloalkyl residue according to the above definition and L is a suitable nucleofuge, i.e. for example a halogen atom such as chlorine, bromine or iodine or a sulfonic acid ester of an alcohol. Preferred sulfonic acid esters (VIII) contain a methylsulfonyloxy residue, trifluoromethanesulfonyloxy-, p-toluolsulfonyloxy-, p-bromobenzenesulfonyloxy- or m-nitrobenzenesulfonyloxy residue as L. As an amide alkylation in the presence of tertiary amino groups, this reaction requires the use of strong auxiliary bases such as potassium-tert-butylate, sodium hydride, potassium hydride or butyl lithium in aprotic, inert solvents. Such solvents can be for example aliphatic or aromatic hydrocarbons (pentane, hexane, heptane, benzene, toluol), ethers (for example, tetrahydrofuran, dioxane) or polar solvents such as dimethylsulfoxide, dimethylformamide or N-methylpyrrolidone. Depending on the reactivity of the educts, the reaction temperatures can lie between −40° C. and 140° C. preferably between −20° C. and 80° C.

Method D

Compounds of formula (I) in which A is a saturated alkylene group can also be produced, aside from methods A, B and C, by hydrating compounds of formula (I) in which A is an unsaturated group according to the above definition, i.e. an alkenylene group or alkadienyl group with elementary hydrogen in the presence of a suitable catalyst. This method is also applicable when the compounds of formula (I) with an unsaturated group A in the molecule simultaneously contain a principally hydrogenolytically cleavable group B, i.e.—as already mentioned above—a benzyl croup, a diphenylmethyl or triphenylmethyl group. In the selection of the conditions, especially the solvent, the temperature and the acid additive in the reaction mixture, the reaction can be controlably driven either to a selective saturation of the C—C multiple bond(s) in the structural element A or to a simultaneous cleavage of the benzyl, diphenylmethyl or triphenylmethyl residue G under formation of the compounds of formula (I) with hydrogen as G.

The hydration is preferably carried out in barely polar, aprotic solvents for selective hydration of one or more C—C multiple bonds of group A in the compounds of formula (I) according to the invention while attaining a simultaneously present hydrogenolytically cleavable benzyl, diphenylmethyl or triphenylmethyl residue as the structural element G. Esters such as ethyl acetate, propyl acetate, butyl acetate or ethers such as tetrahyodrofuran, dioxane or ethylene glycol dimethyl ether can be used. Compounds of formula (I) to be hydrated can be present as a free base or entirely or partially in the form of a salt by addition of a sub-maximal to a maximal stochiometric amount of a strong acid, preferably a mineral acid. As a catalyst, palladium is suitable in various proportional amounts from 1, 3, 5 or 10% on solid supports such as activated carbon, activated aluminum oxide or calcium carbonate. The hydration is carried out under normal pressure and at a temperature of 10 to maximally 30° C., preferably at 20 to 25° C. and interrupted after consumption of the amount of hydrogen calculated for the saturation of the multiple bonds.

In contrasts for simultaneous cleavage of the multiple bonds in A and the cleavage of a benzyl, diphenylmethyl or triphenylmethyl group as G in the compound of formula (I), polar, aprotic solvents are used such as methanol, ethanol isopropanol, methoxyethanol or water or mixtures thereof, whereby a considerable excess of a strong acid compared to the stochiometric salt formation, preferably a mineral acid such as concentrated hydrochloric acid or sulfuric acid is simultaneously added. The molecular ratio of substrate/acid can lie in the range of 1:2 to 1:10 thereby, preferably between 1:3 and 1:5. The same catalysts which are mentioned above in connection with the selective hydration are suitable as catalysts. The hydration is carried out under normal pressure or slightly increased hydrogen pressure of 2 to 3 bar, preferably under normal pressure, until the termination of the uptake of hydrogen Depending on uptake speed, the reaction temperature can vary between 10 and 50, 70 or 80° C. as a function of the boiling point of the solvent and/or solvent mixture and employed pressure. If, for example, the reaction is carried out in ethanol or ethanol/water under normal pressure, the reaction temperature preferably lies between 40 to 60° C.

The compounds of formula (I) produced according to the method (A), (B1) to (B4), (C) or (D) can be isolated and purified in a known manner, for example by subjecting the residue after distillation of the solvent to partition, extraction, re-precipitation or re-crystallization or another purification method. For this, column chromatography on a suitable support or preparative, middle or high pressure liquid chromatography are preferred for this.

The compounds (I) are first normally obtained in form of their free bases or their hydrates or solvates, depending on the type of isolation and purification. Their addition salts with pharmaceutically suitable acids are obtained in a typical manner by converting the base with the desired acid in a suitable solvent. Depending on the number of basic centers of compound (I), one or more equivalent acids per mole of base can be bound.

Suitable solvents are, for example, chlorinated hydrocarbons such as dichloromethane or chloroform; ethers such as diethyl ether, dioxane or tetrahydrofuran; acetonitrile, ketones such as acetone or ethyl methyl ketone; esters such as methyl acetate or ethyl acetate or low molecular alcohols such as methanol, ethanol or isopropanol, and water. Pure solvents as well as mixtures of two or three solvents can also be used. The salts can be isolated by crystallization, precipitation or the evaporation of the solvent. Thereby, they optionally accumulate as hydrates or solvates.

The bases can be recovered from the salts by alkalization, for example with aqueous ammonia solution, alkali carbonate or diluted sodium hydroxide solution.

The following listed compounds and/or their pharmaceutically acceptable salts, if not already concretely labelled as such, are particularly preferred.

N-[2-(1-benzylpiperidin-4-yl)-ethyl]-3-(pyridin-3-yl)-propionamide,

N-{2-[1-(2-phenylethyl)-piperidin-4-yl]-ethyl}-3-(pyridin-3-yl)-propionamide

N-{2-[1-(4-phenylbutyl)-piperidin-4-yl]-ethyl}-3-(pyridin-3-yl)-propionamide

N-{2-[1-(4-hydroxy-4-phenylbutyl)-piperidin-4-yl]-ethyl}-3-(pyridin-3-yl)-propionamide N-[2-(1-diphenylmethylpiperidin-4-yl)-ethyl]-3-(pyridin-3-yl)-propionamide, N-[3-(1-diphenylmethylpiperidin-4-yl)-propyl]-3-(pyridin-3-yl)-propionamide, N-[4-(1-diphenylmethylpiperidin-4-yl)-butyl]-3-(pyridin-3-yl)-propionamide, N-[2-(1-benzylpiperidin-4-yl)-butyl]-3-(pyridin-3-yl)-acrylamide, N-{4-[1-(2-phenylethyl)-piperidin-4yl]-butyl}-3-(pyridin-3-yl)-acrylamide N-{4-[1-(4-biphenylmethyl)-piperidin-4-yl]-butyl}-3-(pyridin-3-yl)-acrylamide N-{4-[1-(1-naphthylmethyl)-piperidin-4-yl]-butyl}-3-(pyridin-3-yl)-acrylamide N-{4-[1-(1-anthrymethyl)-piperidin-4-yl]-butyl}-3-(pyridin-3-yl)-acrylamide N-{4-[1-(Cyclohexylphenylmethyl)-piperidin-4-yl]-butyl}-3-(pyridin-3-yl)-acrylamide N-{4-[1-(10,11-dihydro-5H-dienzo[a,d]cycloheptene-5-yl)-piperidin-4-yl]-butyl}-3-(pyridin-3-yl)-acrylamide N-[2-(1-diphenylmethylpiperidin-4-yl)-ethyl]-3-(pyridin-3-yl)-acrylamide, N-[3-(1-diphenylmethylpiperidin-4-yl)-propyl]-3-(pyridin-3-yl)-acrylamide, N-[5-(1-diphenylmethylpiperidin-4-yl)-pentyl]-3-(pyridin-3-yl)-acrylamide, N-[6-(1-diphenylmethylpiperidin-4-yl)-hexyl]-3-(pyridin-3-yl)-acrylamide, N-[4-(1-diphenylmethylpiperidin-4-yl)butyl]-5-(pyridin-3-yl)-2,4-pentadiene acid amide, N-(4-{1-[bis-(4-fluorophenyl)-methyl]-piperidin-4-yl}-butyl)-3-(pyridin-3-yl)-acrylamide, N-(4-{1-[bis-(2-chlorophenyl)-methyl]-piperidin-4-yl}-butyl)-3-(pyridin-3-yl)-acrylamide, N-[4-(1-diphenylmethylpiperidin-4-yl)-butyl]-3-(2-fluoropyridin-3-yl)-acrylamide, N-[4-(1-diphenylmethylpiperidin-4-yl)-butyl]-3-(6-fluoropyridin-3-yl)-acrylamide, N-[4-(1-diphenylmethylpiperidin-4-yl)-butyl]-3-(pryridin-3-yl)-acrylamide, N-[4-(1-diphenylmethylpiperidin-4-yl)-butyl]-3-(pyridin-3-yl)-acrylamide dihydrochloride or, N-[4-(1-diphenylmethylpiperidin-4-yl)-butyl]-3-(pyridin-3-yl)-acrylamide methanesulfonate.

For a better understanding of the use according to the invention and reproducability of the compounds used, a series of synthetic examples is described in the following.

SYNTHETIC EXAMPLES for the End Products of the Invention According to Formula (I)

In the following production examples for the end products, the abbreviations stand for the following terms:

MP=melting point,
RT=room temperature,
THF=tetrahydrofuran,
DMF=dimethylformamide,
CDI=carbonyldiimidazol,
abs=absolute,
EDC=N-(3-dimethylaminopropyl)-N'-ethyl-carbodiimide hydrochloride,
HOBT=1-hydroxybenzotriazol,
TEA=triethylamine
$^1$H-NMR-Spectrum=proton resonance spectrum, taken at 100 MHz. The chemical shifts are given in ppm against TMS as a standard ($\delta$=0.0), whereby
s=singlet,
d=doublet,
t=triplet,
dt=doublet-triplet,
m=multiplet,
ar=aromatic,
py=pyridine.

Example 1

N-[4-(1-Diphenylmethylpiperidin-4-yl)-butyl]-N-ethyl-3-(pyridin-3-yl)-acrylamide (Substance 123)

10 g (22.0 mmol) N-[4-(1-diphenylmethylpiperidin-4-yl)-butyl]-3-(pyridin-3-yl)-acrylamide (substance 104) are dissolved in 100 ml THE and added to 0.73 g (24.3 mmol) 80% NaH (heavy foaming) and stirred 20 minutes at RT. 2.1 ml (26.4 mmol) ethyl iodine are added dropwise and the mixture is stirred five hours at RT. 0.1 g tetrabutyl ammonium iodine are added and the batch is further stirred at RT overnight. Subsequently, 0.1 g (3 mmol) 80% NaH are added and this is heated at 50° C. for one hour under stirring. The batch is carefully hydrolyzed with 50 ml water after cooling to RT. The aqueous phase is extracted with 100 ml dichloromethane and the combined organic phases are washed with 50 ml water. The organic phase is concentrated in vacuum and the residue is chromatographically pre-purified twice over silica gel with $CHCl_3/CH_3OH$ (95/5 to 90/10 and 98/2 to 95/5), subsequently further purified by flash chromatography with $CHCl_3/CH_3OH$ (100/0 to 98/2) and crystallized three times from 20 ml 1-chlorobutane, 10 ml acetonitrile/diisopropyl ether (1/1) and 8 ml isopropanol/diisopropyl ether (1/1). Yellow crystals with a MP of 115–117° C. were recovered, yield. 1.1 g (10%).

$C_{32}H_{39}N_3O$ (481.7); IR-Spectrum (KBr): $\nu$(C=O) 1640 cm$^{-1}$; $\nu$(C=C) 1600 cm$^{-1}$; $^1$H-NMR-Spectrum (CDCl$_3$): 0.90–1.95 (16H, m, piperidine, piperidine-(CH$_2$)$_3$ CH$_3$); 2.70–3.00 (2H, m, piperidine); 3.20–3.70 (4H, m, CONCH$_2$, J; 4.21 (1H, s, Ar$_2$CH); 6.89 (1H, d, CH=CHCO, J=15.5 Hz) 7.00–7.50 (11H, m, ar, py); 7.69–7.60 (1H, d, CH=CHCO, J=15.5 Hz); 7.70–7.95 (1H, m, py); 8.50–8.65 (1H, m, py); 8.70–8.85 (1H, m, py).

Example 2

N-[4-(1-Diphenylmethylpiperidin-4-yl)-butyl]-3-(pyridin-3-yl)-acrylamide (Substance 104)

2.0 g (13 6 mmol) 3-(pyridin-3-yl)-acrylic acid are suspended in 60 ml abs. dichloromethane and, after addition of three drops of pyridine, cooled to ca. 0° C. in an ice bath under moisture exclusion. 1.8 ml (18.6 mmol) oxalyl chloride are added dropwise and the mixture is stirred at RT overnight. Subsequently, the solvent and excess oxalyl chloride is distilled off in a rotary evaporator. In order to completely remove the oxalyl chloride, the residue is dried further for two hours under high-vacuum. The acid chloride obtained in this manner is suspended in 50 ml abs. dichloromethane and cooled to ca. 0° C. in an ice bath under moisture exclusion. 4.0 g (12.4 mmol) 4-(1-diphenylmethylpiperidin-4-yl)-butylamine are dissolved in 30 ml abs. dichloromethane and added dropwise to this suspension. After complete addition, the ice bath is removed and the reaction mixture is stirred for a further two hours at RT. The mixture is subsequently washed with 10% sodium hydroxide solution. The aqueous phase is extracted with acetic acid ethyl ether. The combined organic phases are dried over sodium sulfate and the solvent is removed under vacuum. The residue is crystallized once from 15 ml isopropanol and then twice from acetic acid ethyl ester. Colorless crystals with a MP of 156° C. were recovered; yield: 1.6 g (28%).

$C_{30}H_{35}N_3O$ (453.6); IR-Spectrum (KBr): $\nu$(NH) 3310 cm$^{-1}$; $\nu$(C=O) 1660, 1545 cm$^{-1}$; $\nu$(C=C) 1620 cm$^{-1}$; $^1$H-NMR-Spectrum (CDCl$_3$): 0.90–2.20 (13H, m, piperidine, piperidine-(CH$_2$)$_3$); 2.65–3.05 (2H, m, piperidine); 3.20–3.60 (2H, m, CONCH$_2$, J; 4.21 (1H, s, Ar$_2$CH); 5.75–6.15 (1H, m, NH); 6.45 (1H, d, CH=CHCO, J=15.6); 6.90–8.00 (13H, m, ar, py, CH=CHCO); 8.45–8.70 (1H, m, py); 8.70–8.90 (1H, m, py).

Example 3

N-(4-{1-[bis-(4-Fluorophenyl)-methyl]-piperidin-4-yl}-butyl)-3-(pyridin-3-yl)-acrylamide (substance 171)

3.7 g (24.5 mmol) 3-(3-pyridyl)-acrylic acid are suspended in 100 ml abs dichloromethane and, after addition of three drops of pyridine. cooled to ca. 0° C. in an ice bath under moisture exclusion. 2.8 ml (22.1 mmol) oxalyl chloride are added dropwise and the mixture is stirred at RT overnight. Subsequently, the solvent and excess oxalyl chloride is distilled off in a rotary evaporator. In order to completely remove the oxalyl chloride, the residue is dried further for 2 hours under high-vacuum. The acid chloride obtained in this manner is suspended in 50 ml abs. dichloromethane and cooled to ca. 0° C. in an ice bath under moisture exclusion. 8.0 g (22.3 mmol) 4-[1-bis-(4-fluorophenyl-methyl-piperidin-4-yl]-butylamine are dissolved in 50 ml abs dichloromethane and added dropwise to this suspension. After complete addition, the ice bath is removed and the reaction mixture is stirred for a further two hours at RT The mixture is subsequently distributed between 10% sodium hydroxide solution and dichloromethane, and the aqueous phase is extracted a further three times with dichloromethane. The combined organic phases are washed with 100 ml water dried over sodium sulfate and the solvent is removed under vacuum. The residue is chromatographically purified over silica gel with $CHCl_3/CH_3OH$ (99.5/0.5 to 97/3) and crystallized from 30 ml acetic acid ethyl ester after drawing off the solvent. Colorless crystals with a MP of 108° C. were recovered; yield: 3,5 g (34%).

$C_{30}H_{33}F_2N_3O$ (489.6);
IR-Spectrum (KBr): $\nu$(NH) 3320 cm$^{-1}$; $\nu$(C=O) 1655, 1540 cm$^{-1}$; $\nu$(C=C) 1620 cm$^{-1}$; $^1$H-NMR-Spectrum (CDCl$_3$): 1.00–2.00 (13H, m, piperidine, piperidine-(CH$_2$)$_3$); 2.60–2.95 (2H, m, piperidine); 3.38 (2H, dt, CONHCH$_2$, J=6.6 Hz, J=12.7 Hz); 4.20 (1H, s, Ar$_2$CH); 5.85–6.10 (1H, m, NH); 6.47 (1H, d, CH=C$\underline{H}$CO, J=15.7 Hz); 6.80–7.50 (9H, m, ar, py); 7.65–7.90 (1H, m, py); 8.45–8.65 (1H, m, py); 8.65–8.85 (1H, m, py);

Example 4

N-{4-[1-(10,11-dihydro-5H-dibenzo[a,d]
cycloheptene-5-yl)-piperidin-4-yl]-butyl}-3-
(pyridin-3-yl)-acrylamide (Substance 219)

Production occurred analogously to Example 3.

Batch size: 2.6 g (17.6 mmol) 3-(3-pyridyl)-acrylic acid, 2.6 g (20.8 mmol) oxalyl chloride and 5.57 g (16.0 mmol) 4-[1-(10,11-dihydro-5H-dibenzo[a,d]cycloheptene-5-yl)-piperidin-4-yl]-butylamine.

In the work up, the mixture is concentrated under vacuum and subsequently distributed between 100 ml 10% NaOH and 300 ml acetic acid ethyl ester. The aqueous phase is extracted again with 50 ml acetic acid ethyl ester and the combined organic phases are washed with 50 ml water, dried over sodium sulfate and the solvent is removed under vacuum. The residue is chromatographically purified over silica gel with $CHCl_3/CH_3OH$ (97/3) and crystallized twice from 40 ml and 30 ml acetonitrile after drawing off the solvent. Colorless crystals with a MP of 125–127° C. were recovered, yield: 2.3 g (30%).

$C_{32}H_3$—$F_2N_3O$ (479.6); IR-Spectrum (KBr): ν(NH) 3300 cm$^{-1}$; ν(C=O) 1655, 1540 cm$^{-1}$; ν(C=C) 1620 cm$^{-1}$; $^1$H-NMR-Spectrum (CDCl$_3$): 0.90–2.00 (13H, m, piperidine, piperidine-(CH$_2$)$_3$); 2.55–3.00 (4H, m, piperidine, ar —CH—CH—ar); 3.36 (2H, dt, CONHC$\underline{H}_2$, J=6.6 Hz, J=12.7 Hz); 3.90 (1H, s, Ar$_2$CH); 5.60–5.85 (1H, m, NH); 6.43 (1H, d, CH=C$\underline{H}$CO, J=15.7 Hz); 6.90–7.40 (9H, m, ar, py); 7.60 (1H, d, CH=C$\underline{H}$CO, J=15.6 Hz); 7.65–7.90 (1H, m, py); 8.50–8.65 (1H, m, py); 8.70–8.80 (1H, m, py).

Example 5

N-[4-(1-Benzylpiperidin-4-yl)-butyl]-3-(pyridin-3-yl)-acrylamide (Substance 46)

6.5 g (180 mmol) N-[4-(piperidin-4-yl)-butyl]-3-(pyridin-3-yl)-acrylamide dihydrochloride (substance 22) are suspended in 80 ml acetone added to 9.9 g (72.0 mmol) potassium carbonate. A solution of 3.4 g (19.8 mmol) benzyl bromide in 10 ml acetone is added dropwise to this mixture at RT and stirred overnight. Subsequently, the suspension is filtered and the filtrate is concentrated under vacuum. The residue is taken up in 100 ml CHCl$_3$ and washed with 30 ml water. The organic phase is dried over sodium sulfate and the solvent is removed under vacuum. The residue is chromatographically purified over silica gel with $CHCl_3/CH_3OH$ (95/5 to 90/10) and crystallized from 15 ml acetonitrile after drawing off the solvent. Beige colored crystals with a MP of 88–90° C. were recovered; yield: 1.1 g (16%).

$C_{24}H_{31}N_3O$ (377.5); IR-Spectrum (KBr): ν(NH) 3320 cm$^{-1}$; ν(C=O) 1655, 1530 cm$^{-1}$; ν(C=C) 1620 cm$^{-1}$; $^1$H-NMR-Spectrum (CDCl$_3$): 100–2.10 (13H, m, piperidine, piperidine-(CH$_2$)$_3$); 2.70–3.00 (2H, m, piperidine); 3.20–3.55 (4H, m, CONHC$\underline{H}_2$, ar, CH$_2$); 5.65–6.00 (H, m, NH); 6.45 (1H, d, CH=C$\underline{H}$CO, J=15.6 Hz); 3.36 (2H, dt, CONHC$\underline{H}_2$, J=6.6 Hz, J=12.7 Hz); 7.10–7.40 (6H, m, ar, py); 7.62 (1H, d, C$\underline{H}$=CHCO, J=15.6 Hz); 5.60–5.85 (1H, m, NH); 6.43 (1H, d, CH=C$\underline{H}$CO, J=15.7 Hz); 7.65–7.90 (1H, m, py); 8.45–8.65 (1H, m, py); 8.65–8.85 (1H, m, py).

Example 6

N-[2-(1-Diphenylmethylpiperidin-4-yl)-ethyl]-3-(pyridin-3-yl)-acrylamide (Substance 95)

Production occurred analogously to Example 3.

Batch size: 2.3 g (15.5 mmol) 3-(3-pyridyl)-acrylic acid, 2.7 g (21.3 mmol) oxalyl chloride and 4.1 g (13.9 mmol) 2-(1-diphenylmethylpiperidine-4-yl)-ethylamine in 60 ml abs. dichlormethane.

In the work up, the mixture is concentrated under vacuum and subsequently dispersed between 100 ml 10% NaOH and 300 ml acetic acid ethyl ester. The aqueous phase is extracted again with 50 ml acetic acid ethyl ester and the combined organic phases are washed with 50 ml water, dried over sodium sulfate and the solvent is removed under vacuum. The residue is chromatographically pre-purified over silica gel with $CHCl_3$ $CH_3OH$ (95/5) and subsequently purified by flash-chromatography with $CHCl_3$ $CH_3OH$ (100/0 to 94/6). After drawing off the solvent, this is crystallized from 19 ml acetic acid ethyl ester/petroleum ether. Colorless crystals with a MP of 141–143° C. were recovered; yield: 0.6 g (10%).

$C_{28}H_{31}N_3O$ (425.6); IR-Spectrum (KBr): ν(NH) 3820 cm$^{-1}$; ν(C=O) 1660, 1550 cm$^{-1}$; ν(C=C) 1620 cm$^{-1}$; $^1$H-NMR-Spectrum (CDCl$_3$): 1.05–2.00 (9H, m, piperidine, piperidine-CH$_2$); 2.70–3.00 (2H, m, piperidine); 3.41 (2H, dt, CONHC$\underline{H}_2$, J=6.6 Hz, J=12.7 Hz); 4.23 (1H, s, Ar$_2$CH); 5.55–5.80 (1H, m, NH); 6.43 (1H, d, CH=C$\underline{H}$CO, J=15.6 Hz); 7.00–7.55 (11H, m, ar, py); 7.61 (1H, d, C$\underline{H}$=CHCO, J=15.6 Hz); 7.60–7.90 (1H, m, py); 8.55–8.65 (1H, m, py); 8.65–8.80 (1H, m, py).

Example 7

N-{4-[1-(9-Anthryl)-methylpiperidin-4-yl]-butyl}-3-(pyridin-3-yl)-acrylamide (Substance 81)

5.4 g (15.0 mmol) N-[4-piperidin-4-yl]-butyl]-3-(pyridin-3-yl)-acrylamide dichloride (substance 22) were suspended in 80 ml dichloromethane and added to 5.1 g (50.0 mmol) TEA. To this mixture, a solution of 3.7 g (16.5 mol) (9-anthyl)-methylchloride in dichloromethane is added at RT and stirred overnight. Subsequently, the mixture is washed twice, each with 100 ml water. The organic phase is dried over sodium sulfate and the solvent is removed under vacuum. The residue is chromatographically purified over silica gel with $CHCl_3/CH_3OH$ (95/5 to 94/6) and crystallized first from 100 ml ethanol and then from 83 ml ethanol/diisopropyl ether (75/8) after drawing off the solvent. Yellow crystals with a MP of 162–164° C. were recovered; yield: 1.8 g (25%).

$C_{32}H_{35}N_3O$ (477.6); IR-Spectrum (KBr): ν(NH) 3360 cm$^{-1}$; ν(C=O) 1680, 1560 cm$^{-1}$; ν(C=C) 1640 cm$^{-1}$; $^1$H-NMR-Spectrum (CDCl$_3$): 0.90–1.80 (11H, m, piperidine, piperidine-CH$_2$)$_3$); 2.05–2.40 (2H, m, piperidine); 2.80–3.15 (2H, m, piperidine); 3.20–3.55 (2H, m, CONHC$\underline{H}_2$); 4.45 (1H, s, Ar$_2$CH); 5.60–5.90 (1H, m, NH); 6.42 (1H, d, CH=C$\underline{H}$CO, J=15.6 Hz); 7.20–8.20 (10H, m, ar, py, C$\underline{H}$=CHCO); 8.40–8.90 (4H, m, ar, py).

Example 8

N-{4-[1-(Bromocyclohexylphenylmethyl)-piperidin-4-yl]-butyl}-3-(pyridin-3-yl)-acrylamide (Substance 84)

4.5 g (17.7 mmol) (bromocyclohexylphenyl)-methane, 5.6 g (15.5 mmol) N-[4-(piperidin-4-yl)-butyl]-3-(pyridin-3-yl)-acrylamide dihydrochloride (substance 22), 8.5 g (61.8 mmol) potassium carbonate and 2.8 g (16.9 mmol) sodium iodide are stirred in 200 ml DMF 18 hours at ca 75° C. After cooling, the mixture is filtered over a diatomaceous earth layer and the filtrate is concentrated under vacuum. The residue is taken up in 200 ml CHCl₃ and washed twice with 60 ml and 30 ml water. The organic phase is dried over a sodium sulfate and the solvent is removed under vacuum. The residue is chromatographically purified over a silica gel with CHCl₃/CH₃OH (96/4 bis 92/8) and crystallized three times, each from 40 ml acetonitrile and once at the conclusion from 50 ml acetonitrile. Colorless crystals with a MP of 143–145° C. were recovered; yield: 0.58 g (8%).

$C_{30}H_{42}N_3O$ (459.7); IR-Spectrum (KBr): ν(NH) 3330 cm⁻¹; ν(C=O) 1680, 1570 cm⁻¹; ν(C=C) 1640 cm⁻¹; ¹H-NMR-Spectrum (CDCl₃): 0.50–2.20 (24H, m, piperidine, piperidine-CH₂)₃, cyclohexane); 2.55–2.90 (2H, m, piperidine); 3.08 (1H, d, Ar—CH, J=9.2 Hz); 3.35 (2H, dt, CONHC$\underline{H}_2$, J=6.5 Hz, J=12.7 Hz); 5.70–6.05 (1H, m, NH); 6.45 (1H, d, CH=C$\underline{H}$CO, J=15.6 Hz); 7.00–7.50 (6H, m, ar, py); 7.60 (1H, d, C$\underline{H}$=CHCO, J=15.6 Hz); 7.60–7.90 (1H, m, py); 8.45–8.65 (1H, m, py); 8.65–8.85 (1H, m, py).

Example 9

N-(4-{1-[bis-(2-Chlorphenyl)-methyl]-piperidin-4-yl}-butyl)-3-(pyridin-3-yl)-acrylamid (Substance 186)

Production occurred analogously to Example 3.

Batch size: 1.6 g (10.7 mmol) 3-(3-pyridyl)-acrylic acid, 1.9 g (15.0 mmol) oxalyl chloride and 3.9 g (10.0 mmol) 4-{1-[bis-(2-chlorophenyl)-methyl]-piperidine-4-yl}-butylamine. In the purification, chromatographic purification is done twice over silica gel with CHCl₃/CH₃OH (97/3 and 97/3 to 95/5) and crystallization is from 25 ml acetic acid after drawing off the solvent. Colorless crystals with a MP of 129–131° C. were recovered; yield: 0.6g (11%).

$C_{30}H_{33}Cl_2N_3O$ (522.5); IR-Spectrum (KBr): ν(NH) 3240 cm⁻¹; ν(C=O) 1655, 1560 cm⁻¹; ν(C=C) 1620 cm⁻¹; ¹H-NMR-Spectrum (CDCl₃): 0.90–1.95(11H, m, piperidine, piperidine-CH₂)₃); 1.90–2.40 (2H, m, piperidine); 2.55–3.00 (2H, m, piperidine); 3.38 (2H, dt, CONC$\underline{H}_2$ J=6.5 Hz, J=12.4 Hz); 5.31 (1H, s, Ar₂CH); 5.55–5.90 (1H, m, NH); 6.44 (1H, d, CH=C$\underline{H}$CO, J=15.6 Hz); 6.90–8.00 (11H, m, ar, py, C$\underline{H}$=CHCO); 8.55–8.70 (1H, m, py); 8.70–8.95 (1H, m, py).

Example 10

N-[3-(1-Diphenylmethylpiperidin-4-yl)-propyl]-3-(pyridin-3-yl)-acrylamide (Substance 97)

Production occurred analogously to Example 3.

Batch size: 3.9 g (26.1 mmol) 3-(3-pyridyl)-acrylic acid, 4.1 g (47.4 mmol) oxalyl chloride and 7.3 g (23.7 mmol) 3-(1-diphenylmethylpiperidine-4-yl)-propylamine.

In the purification, crystallization is done first from 1-chlorobutane and subsequently once from acetic acid. Colorless crystals with a MP of 110–113° C. were recovered, yield: 6.2 g (60%).

$CH_{29}H_{33}N_3O$ (439.6); IR-Spectrum (KBr): ν(NH) 3240 cm⁻¹; ν(C=O) 1650, 3555 cm⁻¹; ν(C=C) 1605 cm⁻¹; ¹H-NMR-Spectrum (CDCl₃): 0.90–2.25 (11H, m, piperidine, piperidine-CH₂)₃); 2.70–3.05 (2H, m, piperidine); 3.36 (2H, dt, CONC$\underline{H}_2$ J=6.5 Hz, J=12.8 Hz); 4.21 (1H, s, Ar₂CH); 5.85–6.20 (1H, m, NH); 6.46 (1H, d, CH=C$\underline{H}$CO, J=15.7 Hz); 6.90–7.70 (11H, m, ar, py); 7.60 (1H, d, C$\underline{H}$=CHCO, J=15.7 Hz); 7.60–7.90 (1H, m, py); 8.45–8.65 (1H, m, py); 8.65–8.85 (1H, m, py).

Example 11

N-[3-(1-Diphenylmethylpiperidin-4-yl)-propyl]-3-(pyridin-3-yl)-propionamide (Substance 96)

3.0 g (6.8 mmol) N-[3-(1-diphenylmethylpiperidin-4-yl)-propyl]-3-(pyridin-3-N)-acrylamide (substance 97) are suspended in 60 ml THF and added to 5 drops concentrated hydrochloric acid and 0.35 g palladium (5%) on activated carbon. The mixture is stirred at RT under hydrogen atmosphere until consumption of the theoretical amount of hydrogen to be taken up. The suspension is filtered from the catalyst and the solvent is removed under vacuum. The residue is chromatographically purified over a silica gel with CHCl₃/CH₃OH/NH₄OH (85/15/2) and crystallized twice after drawing off the solvent. Colorless crystals with a MP of 109–110° C. were recovered; yield: 1.7 g (56%).

$C_{29}H_{35}N_3O_2$ (441.6); IR-Spectrum (KBr): ν(NH) 3230 cm⁻¹; ν(C=O) 1620, 1555 cm⁻¹; ¹H-NMR-Spectrum (CDCl₃): 1.00–2.00 (11H, m, piperidine, piperidine-CH₂)₃); 2.44 (2H, t, CO—CH₂, J=7.4 Hz); 2.75–3.15 (4H, m, piperidine, py-CH₂); 3.15 (2H, dt, CONC$\underline{H}_2$ J=6.7 Hz, J=13.0 Hz); 4.21 (1H, s, Ar₂CH); 5.30–5.60 (1H, m, NH); 7.00–7.70 (12H, m, Ar, pyridine; 6.90–7.70 (11H, m, ar, py); 8.35–8.55 (2H, m, pyridine).

Example 12

N-[4-(1-Diphenylmethylpiperidin-4-yl)-butyl]-2-(pyridin-3-yloxy)-acetamide (Substance 129)

5.0 g (32.6 mmol) 3-pyridyloxyacetic acid and 3.95 g (39.1 mmol) TEA are suspended in 200 ml abs. dichloromethane and cooled to ca. 0° C. under moisture exclusion. 6.34 g (41.3 mmol) 88% HOBT and 7.49 g (39.1 mmol) EDC are added and the mixture is stirred 30 min under ice cooling. 11.56 g (35.9 mmol) N-4-(1-diphenylmethylpiperidine-4-yl)-butylamine are dissolved in 50 ml abs. dichloromethane and added dropwise under ice cooling. The mixture is stirred without further cooling at RT overnight. Subsequently, the batch is washed once with 50 ml 1M NaOH and twice each with 70 ml water. The organic phase is dried over sodium sulfate and the solvent is removed under vacuum. The resinous residue is chromatographically purified over silica gel with CHCl₃/CH₃OH (95/5 to 90/10) and crystallized from 30 ml acetic acid ethyl ester after drawing off the solvent. Colorless crystals with a MP of 103–105° C. were recovered; yield: 3.45 g (23%).

$C_{29}H_{35}N_3O_2$ (457.6); IR-Spectrum (KBr): ν(NH) 3360 cm⁻¹; ν(C=O) 1660, 1545 cm⁻¹; ¹H-NMR-Spectrum (CDCl₃): 0.95–2.05 (13H, m, piperidine, piperidine-CH₂)₃); 2.70–3.00 (2H, m, piperidine); 3.34 (2H, dt, CONHC$\underline{H}_2$, J=6.5 Hz, J=12.9 Hz); 4.21 (1H, s, Ar₂CH); 4.51 (2H, s, COCH₂O); 6.40–6.70 (1H, m, NH); 7.00–7.60 (12H, m, Ar, py); 8.20–8.45 (2H, m, py).

Example 13

N-[5-(1-Diphenylmethylpiperidin-4-yl)-pentyl]-3-(pyridin-3-yl)-propionamide (Substance 142)

2.47 g (16.3 mmol) 3-(3-pyridyl)-priopionic acid are suspended in 40 ml abs dichloromethane and, after addition of three drops of pyridine, cooled to ca. 0° C. in an ice bath under moisture exclusion. 1.90 ml (22.3 mmol) oxalyl chloride are added slowly and the mixture is first stirred under ice cooling for 30 minutes and then at RT overnight. Subsequently, the solvent and excess oxalyl chloride is distilled off in a rotary evaporator. In order to completely remove the oxalyl chloride. the colorless residue is further dried for two hours under high-vacuum. The acid chloride obtained in this manner is suspended in 50 ml abs. dichloromethane and cooled to ca. 0° C. in an ice bath under moisture exclusion without further purification. 5.0 g (14.8 mmol) 5-(1-diphenylmethylpiperidin-4-yl)-pentylamine are dissolved in 40 ml abs. dichloromethane and added dropwise to this suspension. After complete addition, the ice bath is removed and the reaction mixture is stirred for a further two hours at RT. The mixture is subsequently concentrated, taken up in 10% sodium hydroxide solution and extracted three times with acetic acid ethyl ester. The combined organic phases are washed with a saturated NaCl solution, dried over sodium sulfate and the solvent is removed in a vacuum. The residue is chromatographically purified over silica gel with $CHCl_3/CH_3OH$ (96/4) and crystallized from 40 ml acetonitrile after drawing off the solvent. Colorless crystals with a MP of 112–114° C. were recovered; yield: 3.5 g (50%).

$C_{31}H_{39}N_3O$ (469.7); IR-Spectrum (KBr): ν(NH) 3260 $cm^{-1}$; ν(C=O) 1635, 1550 $cm^{-1}$; $^1$H-NMR-Spectrum ($CDCl_3$): 0.90–2.00 (15H, m, piperidine, piperidine-$CH_2$)$_4$); 2.40 (2H, t, CH—$CH_2$, J=7.5); 2.70–3.10 (4H, m, piperidine, py, $CH_2$); 3.19 (2H, dt, CONH$CH_2$, J=6.6 Hz, J=12.6 Hz); 4.21 (1H, s, $Ar_2$CH); 5.30–5.60 (1H, m, NH); 7.00–7.75 (12H, m, Ar, py); 8.35–8.65 (2H, m, py).

Example 14

N-[4-(1-Diphenylmethylpiperidin-4-yl)-butyl]-3-(pyridin-3-yl)-propionamide (Substance 100)

21.6 g (131 mmol) 3-(3-pyridyl)-propionic acid methyl ester, 35.1 g ml (109 mmol) 4-(1-diphenylmethylpiperidine-4-yl)-butylamine and 9.8 g (54.5 mmol) 30% sodium methylate solution in methanol are heated to boiling in 480 ml toluene for five hours. Subsequently, 30 ml of solvent are distilled; thereby, sodium methylate precipitates and the temperature of the suspension increases to 102° C. under heavy foaming. The mixture is cooled to 70–80° C. and extracted twice with 45 ml and 30 ml of water. The organic phase is azeotropically dried on a moisture separator and cooled to ca. 0° C. The resulting precipitate is filtered off and crystallized from 190 ml toluol. Colorless crystals with a MP of 139° C. were recovered; yield: 46.3 g (93%).

$C_{30}H_{37}N_3O$ (445.6); IR-Spectrum (KBr): ν(NH) 3250 $cm^{-1}$; ν(C=O) 1630, 1570 $cm^{-1}$; $^1$H-NMR-Spectrum ($CDCl_3$): 1.00–2.10 (13H, m, piperidine, piperidine-$CH_2$)$_3$); 2.43 (2H, t, CO—$CH_2$, J=7.4 Hz); 2.70–3.10 (4H, m, py-$CH_2$); 3.12 (2H, dt, CONH$CH_2$, J=6.5 Hz, J=12.5 Hz); 4.21 (1H, s, $Ar_2$CH); 5.45–5.75 (1H, m, NH); 7.05–7.60 (12H, m, Ar, py); 8.30–8.60 (2H, m, py).

Example 15

N-{4-[1-(6,11-Dihydrodibenzo[b,e]-oxepin-11-yl)-piperidine-4-yl]-butyl}-3-(pyridin-3-yl)-propionamide (Substance 230)

3.46 g (15 mmol) 11-chloro-6,11-dihydrodibenzo[b,e]oxepine are dissolved in 90 ml abs dichloromethane and 5.43 g (15 mmol) N-(4-piperidin-4-yl-butyl)-3-(pyridin-3-yl)-propionamide dihydrochloride are added. 5.0 g (49.5 mmol) TEA are dissolved in 20 ml abs. dichloromethane and added dropwise under ice cooling. The mixture is stirred without further cooling for two days at RT. Subsequently, the batch is washed twice each with 50 ml water. The organic phase is dried over silica gel with $CHCl_3/CH_2OH$ (95/5) and crystallized twice at first, each from 10 ml 1-chlorobutane, and subsequently crystallized once from 10 ml acetic acid. Colorless crystals with a MP of 110–112° C. were isolated; yield: 0.2 g (3%).

$C_{31}H_{37}Cl_2N_3O_2$ (483.6); IR-Spectrum (KBr): ν(NH) 3240 $cm^{-1}$; ν(C=O) 1630, 3570 $cm^{-1}$; $^1$H-NMR-Spectrum ($CDCl_3$): 0.80–2.00 (13H, m, piperidine, piperidine-$CH_2$)$_3$); 2.43 (2H, t, CO—$CH_2$, J=7.5 Hz); 2.55–3.30 (6H, m, piperidine, py-$CH_2$, CONH$CH_2$); 3.83 (1H, s, $Ar_2$CH); 4.68 (1H, d, O—CH, J=11.3 Hz); 5.25–5.55 (1H, M, NH); 6.65–7.65 (11H, m, A, py, O—CH); 8.35–8.60 (2H, m, py).

Example 16

N-{4-[1-(9H-Fluorene)-piperidine-4-yl]-butyl}-3-(pyridin-3-yl)-propionamide (Substance 209)

8.0 g (27.7 mmol) N-(4-piperidin-4-yl-butyl)-3-(pyridin-3-yl)-propionamide and 5.6 g (55.3 mmol) TEA are present in 100 ml acetonitrile and cooled to ca. 0° C. under moisture exclusion. 6.8 g (27.7 mmol) 9-bromofluorene are added in solid form and the mixture is stirred for 2 days at ca. 65° C. and for two days at RT. Subsequently the solvent is drawn off under vacuum to a large extent and the residue is dispersed between $CHCl_3$ and 10% NaOH. The organic phase is washed twice with water and dried over sodium sulfate. After the removal of the solvent, the residue is chromatographically purified over silica gel with $CHCl_3/CH_3OH$ (98/2 to 94/6) and crystallized from 30 ml acetonitrile after drawing off the solvent. Colorless crystals with a MP of 131–132° C. were recovered; yield: 2.5 g (20%).

$C_{30}H_{35}N_3O$ (453.6); IR-Spectrum (KBr): ν(NH) 3300 $cm^{-1}$; ν(C=O) 1630, 1530 $cm^{-1}$; $^1$H-NMR-Spectrum ($CDCl_3$): 0.95–1.80 (11H, m, piperidine, piperidine-$CH_2$)$_3$); 2.25–2.80 (6H; m, piperidine, CO—$CH_2$); 2.97 (2H, t, py-$CH_2$, J=7.5 Hz); 3.19 (2H, dt, CONH$CH_2$, J=6.5 Hz, J=12.5 Hz); 4.82 (1H, s, ArCH); 5.25–5.55 (1H, m, NH); 7.10–7.80 (10H, m, Ar, py,); 8.35–8.55 (2H, m, py).

Example 17

N-{4-[1-(2-Naphthylsulfonyl)-piperidin-4-yl]-butyl}-3-(pyridin-3-yl)-propionamide (Substance 337)

3.5 g (12 mmol) N-(4-piperidin-4-yl-butyl)-3-(pyridin-3-yl)-propionamide and 6.7 g (48.1 mmol) TEA are present in 100 ml abs. dichloromethane and cooled to ca. 0° C. under moisture exclusion. 3.0 g (13.2 mmol) naphthaline-2-sulfonic acid chloride are dissolved in 40 ml abs dichloromethane and added dropwise. The mixture is stirred without further cooling at RT overnight. Subsequently, the batch is washed twice, each with 80 ml water. The organic phase is dried over sodium sulfate and the solvent is removed under vacuum. The residue is chromatographically purified over silica gel with $CHCl_3/CH_3OH$ (97/3) and crystallized from acetic acid ethyl ester after drawing off the solvent. Colorless crystals with a MP of 103–105° C. were recovered; yield: 2.87 g (50%).

$C_{27}H_{33}N_3O_3S$ (479.6): IR-Spectrum (KBr): ν(NH) 3320 $cm^{-1}$; ν(C=O) 1645, 1530 $cm^{-1}$; $^1$H-NMR-Spectrum ($CDCl_3$): 0.90–1.90 (11H, m, piperidine, piperidine-$CH_2$)$_3$); 2.05–2.40 (2H, m, piperidine); 2.42 (2H, t, CO—$CH_2$, J=7.4 Hz); 2.80–3.30 (4H, t, dt, Py-$CH_2$, J=7.4 Hz, CONH$CH_2$); 3.70–4.00 (2H, m, piperidine); 5.40–5.70 (1H, m, NH); 7.10–8.15 (8H, m, Ar, Py,); 8.25–8.55 (3H, m, Ar, Py).

Example 18

N-{4-[1-(Naphthylaminocarbonyl)-piperidin-4-yl]-butyl}-3-(pyridin-3-yl)-propionamide (Substance 305)

2.6 g (17.7 mmol) 1-naphthyl isocyanate are dissolved in 15 ml abs. THF and cooled to 0° C. under moisture exclusion. 5.1 g (17.7 mmol) N-(4-piperidine-4-yl-butyl)-3-(pyridine-3-yl)-propionamide are dissolved in 35 ml abs. THF and added dropwise under ice cooling. The mixture is stirred without further cooling at RT overnight. Subsequently, the solution is drawn off under vacuum to a large extent and the residue is chromatographically purified over silica gel with $CHCl_3/CH_3OH$ (90/10) and further purified by flash-chromatography with $CHCl_3/CH_3OH$ (95/5 to 90/10). After drawing off the solvent, crystallization occurs from isopropanol/diisopropanol. Colorless crystals with a MP of 143–144° C. were recovered; yield 0.77 g (9%).

$C_{28}H_{34}N_4O_2$ (458.6); IR-Spectrum (KBr): $\nu$(NH) 3240 $cm^{-1}$; $\nu$(C=O) 1630, 1560 $cm^{-1}$; $^1$H-NMR-Spectrum $(CDCl_3)$: 0.95–1.95 (11H, m, piperidine, piperidine-$CH_2)_3$); 2.40 (2H, t, CO—$CH_2$, J=7.4 Hz); 2.75–3.40 (6H, m, piperidine, Py-$CH_2$, CONHC$\underline{H}_2$); 4.00–4.30 (2H, m, piperidine); 5.55–5.85 (1H, m, NH); 6.77 (1H, s, NH); 7.10–8.00 (9H, m, Ar, Py,); 8.35–8.55 (2H, m, Ar, Py).

Example 19

N-{4-[1-(2-Naphthoyl)-piperidin-4-yl]-butyl}-3-(pyridin-3-yl)-propionamide (Substance 274)

6.0 g (20.7 mmol) N-(4-piperidine-4-yl-butyl)-3-(pyridine-3-yl)-propionamide and 2.1 g (20.7 mmol) TEA are dissolved in 30 ml abs. dichloromethane and cooled to ca. 0° C. under moisture extraction. 3.95 g (20.7 mmol) 2-naphthoylchloride are dissolved in 40 ml abs. dichloromethane and added dropwise under ice cooling. The mixture is stirred without further cooling at RT overnight. Subsequently, the batch is made basic by the addition of 10% sodium hydroxide solution and washed twice with a small amount of water. The organic phase is dried over sodium sulfate and the solvent is removed under vacuum. The resinous residue is chromatographically purified with $CHCl_3/CH_3OH$ (96/4). Yield of colorless resin: 5.4 g (59%).

$C_{28}H_{33}N_3O_2$ (443.6); IR-Spectrum (KBr): $\nu$(NH) 3300 $cm^{-1}$; $\nu$(C=O) 1630, 1540 $cm^{-1}$; $^1$H-NMR-Spectrum $(CDCl_3)$: 1.00–2.05 (11H, m, piperidin, piperidine-$(CH_2)_3$); 2.55 (2H, t, CH—$CH_2$, J=7.5 Hz); 2.70–3.45 (6H, m, piperidine, Py-$CH_2$, CONHC$\underline{H}_2$); 3.65–4.15 (1H, m, piperidin); 4.50–5.05 (1H, m, piperidine); 5.60–5.85 (1H, m, NH); 7.20–7.35 (1H, m, Py); 7.50–7.75 (4H, m, Ar, Py); 7.85–8.10 (4H, m, Ar); 8.40–8.65 (2H, m, Py).

Example 20/1

N-(4-Piperidin-4-yl-butyl)-3-(pyridin-3-yl)-propionamide (Substance 21)

100 g (219.5 mmol) N-[4-(1-diphenylmethylpiperidin-4-yl)-butyl]-3-(pyridine-3-yl)-propionamide (substance 100) are dissolved in 500 ml ethanol and mixed with 8.0 g palladium (5%) on activated carbon (moistened with 40 ml water) and 25 ml conc. hydrochloric acid. The mixture is heated to ca. 45° C. and stirred under hydrogen atomosphere until consumption of the theoretical amount of hydrogen to be taken up (ca. five hours). After cooling, the catalyst is filtered and the solvent is removed under vacuum. The residue is taken up in 200 ml water and washed three times with a total of 200 ml $CHCl_3$. The organic phases are discarded and the aqueous phase is made alkaline with 11 g sodium hydroxide and extracted three times, each with 100 ml $CHCl_3$. After washing the organic phase with 30 ml water, the solvent is removed under vacuum. The oily residue is filtered over silica gel with $CHCl_3/CH_3OH/NH_4OH$ (80/20/2). Yield of the gradually hardening resin 53.0 g (83%).

For spectroscopic data, see Example 20/2.

Example 20/2

N-(4-Piperidin-4-1-butyl)-3-(pyridin-3-yl)-propionamide (Substance 21)

100 g (219.5 mmol) N-[4-(1-diphenylmethylpiperidine-4-yl)-butyl]-3-(pyridine-3-yl)-acrylamide (Substance 104) are dissolved in 500 ml ethanol and mixed with 8.0 g palladium (5%) on activated carbon (moistened with 40 ml water) and 25 ml conc. hydrochloric acid. The mixture is heated to ca. 45° C. and stirred under hydrogen atomosphere until consumption of the theoretical amount of hydrogen to be taken up (ca. 1 day). After cooling the catalyst is filtered and the solvent is removed under vacuum. The residue is taken up in 400 ml water and washed twice, each with 100 ml toluol. The organic phases are discarded and the aqueous phase is made alkaline with 400 ml 4M-sodium hydroxide solution and extracted three times each with 200 ml dichloromethane. The combined organic phases are dried over sodium sulfate and the solvent is removed under vacuum. The wax-like residue is filtered over silica gel with $CHCl_3/CH_3OH/NH_4OH$ (90/9/1). Yield: 58.3 g (91%).

$C_{28}H_{33}N_3O_2$ (443.6); IR-Spectrum (KBr): $\nu$(NH) 3300 $cm^{-1}$; $\nu$(C=O) 1630, 1540 $cm^{-1}$; $^1$H-NMR-Spectrum $(CDCl_3)$: 0.90–1.80 (12H, m, piperidin, NH; piperidine-$(CH_2)_3$); 2.35–2.75 (4H, m, CO—$CH_2$, piperidine); 2.80–3.35 (6H, m, piperidine. Py-$CH_2$, CONHC$\underline{H}_2$); 6.05–6.40 (1H, m, NH); 7.10–7.35 (1H, m, Py); 7.40–7.60 (1H, m, Py); 7.20–7.35 (1H, m, Py); 8.30–8.55 (2H, m, Py).

Example 21

N-{4-[1-(6,11-Dihydrodibenzo[b,e]thiepin-11-yl)-piperidine-4-yl]-butyl}-3-(pyridin-3-yl)-acrylamide (Substance 230)

7.02 g (21.5 mmol) N-[4-piperidine-4-yl)-butyl]-3-(pyridine-3-yl)-acrylamide dihydrochloride (substance 22 as dihydrochloride) are suspended in 100 ml abs. dichloromethane and mixed with 7.08 g (70.0 mmol) TEA. The mixture is cooled to ca. 0° C. under moisture exclusion and a solution of 5.30 g (21.5 mmol) 11-chloro-6,11-dihydrodibenzo[b,e]thiepine in 10 ml abs. dichloromethane is added dropwise. The mixture is stirred without further cooling for 24 hours at RT. Subsequently, the batch is washed with 50 ml 10% sodium hydroxide solution and 30 ml water. The organic phase is dried over sodium sulfate and the solution is removed under vacuum. The red-brown residue is chromatographically purified three times over silica gel with $CHCl_3/CH_3OH$ (100/0, 97/3 and 96/4 to 94/6. Subsequently, further purification occurs by means of MPLC with $CHCl_3/CH_3OH$ (98/2). yield: 0.5 g (5%) of a brittle vitreous solid with a MP of 89–91° C.

$C_{34}H_{35}Cl_2N_3OS$ (497.7); IR-Spectrum (KBr): $\nu$(NH) 3280 $cm^{-1}$; $\nu$(C=O) 1660, 1550 $cm^{-1}$; $\nu$(C=C) 1620 $cm^{-1}$; $^1$H-NMR-Spectrum $(CDCl_3)$: 0.90–2.00 (13H, m, piperidine, piperidine-$CH_2)_3$); 2.55–2.95 (2H, m, piperidine); 3.20–3.60 (3H, m, CONHC$\underline{H}_2$, SC$H_2$); 4.03 (1H, s, $Ar_2CH$); 6.10–6.35 (1H, m, NH); 5.95–6.30 (1H, m, SC$H_2$); 6.44 (1H, d, CH=C$\underline{H}$O J=15.7 Hz); 4.68 (1H, d, O—CH, J=11.3 Hz); 6.85–7.40 (9H, m, Ar, Py); 8.50–8.65 (1H, m, Py); 8.65–8.80 (1H, m, Py).

Example 22

N-[4-(1-Diphenylmethylpiperidine-4-yl)-butyl]-5-(pyridin-3-yl)-2,4-pentadienoic Acid Amide (Substance 132)

3.85 g (22.0 mmol) 5-(3-pyridyl)-2,4-pentadieneoic acid are suspended in 90 ml abs. dichloromethane and, after addition of three drops of pyridine, cooled to ca. 0° C. in an ice bath under moisture exclusion. 3.8 g (30,0 mmol) oxalyl chloride are added dropwise and the mixture is stirred at RT overnight. Subsequently, the solvent and excess oxalyl chloride are distilled off on a rotary evaporator. In order to completely remove the oxalyl chloride, the residue is dried for a further two hours under high-vacuum. The acid chloride obtained in this manner is suspended in 50 ml abs dichloromethane and cooled to ca. 0° C. 6.44 g (20.0 mmol) 4-(1-diphenylmethylpiperidine-4-yl)-butylamine are dissolved in 40 ml abs dichloromethane and added dropwise to the suspension. After complete addition, the ice bath is removed and the reaction is stirred for a further two hours at RT. The mixture is subsequently washed with 10% sodium hydroxide solution. The organic phase is flashed twice, each with 40 ml water, dried over sodium sulfate and the solution is removed under vacuum. The residue is chromatographically purified three times over silica gel with $CHCl_3/CH_3OH$ (98/2 to 95/5) and crystallized twice from 250 ml acetonitrile after removal of the solvent. Beige-colored crystals with a MP of 164–166° C. are isolated; yield: 4.7 g (49%).

$C_{32}H_{35}N_3O$ (479.6); IR-Spectrum (KBr): ν(NH) 3280 $cm^{-1}$; ν(C=O) 1650, 1550 $cm^{-1}$; ν(C=C) 1600 $cm^{-1}$; $^1$H-NMR-Spectrum ($CDCl_3$): 1.00–2.00 (13H, m, piperidine, piperidine-$CH_2)_3$); 2.70–3.00 (2H, m, piperidine); 3.34 (2H, dt, CONHC$\underline{H}_2$, J=6.6 Hz, J=12.8 Hz); 4.21 (1H, s, $Ar_2CH$); 5.50–5.75 (1H, m, NH); 6.44 (1H, d, CH=C$\underline{H}$ J=14.7 Hz); 6.75–6.95 (2H, m, CH=CH); 7.05–7.50 (12H, m, Ar, Py, CH=CH); 7.65–7.85 (1H, m, Py); 8.45–8.55 (1H, m, Py); 8.60–8.75 (1H, m, Py).

Example 23

N-[4-(1-Benzoylpiperidine-4-yl)-butyl]-3-(pyridin-3-yl)-acrylamide (Substance 259)

5.1 g (36.2 mmol) benzoyl chloride are dissolved in 150 ml abs. dichloromethane and cooled to ca. 0° C. under moisture exclusion. 10.4 g (36.2 mmol) N-[4-piperidine-4-yl)-butyl]-3-(pyridin-3-yl)-acrylamide (Substance 22) are dissolved in 50 ml abs. dichloromethane and added dropwise under ice cooling. The mixture is stirred without further cooling at RT overnight. Subsequently, the suspension is added to 60 ml sodium hydroxide solution and extracted twice, each with 80 ml dichloromethane. The combined organic phases are washed twice, each with 60 ml water, dried over sodium sulfate and the solution is removed under vacuum. The residue is chromatographically purified three times over silica gel with $CHCl_3/CH_3OH$ (97/3 to 95/5) and crystallized from 75 ml acetonitrile. Colorless crystals with a MP of 100–102° C. were recovered, yield: 9.8 g (69%).

IR-Spectrum (KBr): ν(NH) 3280 $cm^{-1}$; ν(C=O) 1670, 1545 $cm^{-1}$; ν(C=C) 1630 $cm^{-1}$; $^1$H-NMR-Spectrum ($CDCl_3$): 0.80–2.00 (11H, m, piperidine, piperidine-$CH_2)_3$); 2.55–4.00 (5H, m, piperidine, CONHC$\underline{H}_2$); 4.40–4.90 (1H, piperidine); 6.00–6.25 (1H, m, NH); 6.48 (1H, d, CH=C$\underline{H}$CO, J=15.7 Hz); 8.50–8.65 (1H, m, Py); 8.65–8.80 (1H, m, Py).

Example 24

N-(1-Diphenylmethylazetidin-3-ylmethyl)-3-(pyridin-3-yl)-acrylamide (Substance 2)

Production occurred analogously to Example 22.

Batch size: 4.3 g (28.7 mmol) 3-(3-pyridyl)-acrylic acid, 6.7 ml (78.4 mmol) oxalyl chloride and 6.6 g (26.1 mmol) 3-(1-diphenylmethylazetidine-3-ylmethyl)-amine In the work up, the reaction mixture is washed with sodium hydroxide solution. The aqueous phase is extracted twice, each with 50 ml dichloromethane. The combined organic phases are dried over sodium sulfate and the solvent is removed under vacuum. The residue is chromatigraphically pre-purified over silica gel with $CHCl_3/CH_3OH$ (98/2 to 95/5) and subsequently purified twice by flash chromatography smith $CHCl_3/CH_3OH$ (99/1 to 95/5). A amorphous solid with a MP of 72–74° C. remains after the removal of the solvent; yield: 0.75 g (7%).

$C_{25}H_{25}N_3O$ (383.5); IR-Spectrum (KBr): ν(NH) 3320 $cm^{-1}$; ν(C=O) 1680, 1570 $cm^{-1}$; ν(C=C) 1640 $cm^{-1}$; $^1$H-NMR-Spectrum ($CDCl_3$): 2.40–2.80 (1H, m, azetidine); 2.80–3.10 (2H, m, azetidine); 3.10–3.40 (2H, m, azetidine); 3.60 (2H, dd, CONC$\underline{H}_2$ J=6.5 Hz, J=12.8 Hz); 4.36 (1H, $Ar_2CH$); 6.45–6.75 (1H, m, NH); 6.50 (1H, d, CH=C$\underline{H}$CO, J=15.7 Hz); 7.00–7.50 (11H, m, Ar, Py); 7.62 (1H, d, C$\underline{H}$=CHCO, J=15.7 Hz); 7.65–7.90 (1H, m, Py); 8.50–8.70 (1H, m, Py); 8.70–8.85 (1H, m, Py).

Example 25

N-(4-Diphenylmethylmorpholin-2-ylmethyl)-3-yl)-(pyridin-3-yl)-acrylamide (Substance 378)

Production occurred analogously to Example 22.

Batch size: 2.3 g (15.6 mmol) 3-(3-pyridyl)-acrylic acid, 5.4 g (42.5 mmol) oxalyl chloride and 3.6 (14.7 mmol) 2-aminomethyl-4-diphenylmethylmorpholine.

In the work up, 40 ml 10% sodium hydroxide solution are added to the reaction solution. The aqueous phase is extracted with 15 ml dichloromethane. The combined organic phases are washed twice, each with 15 ml water, dried over sodium sulfate and the solvent is removed under vacuum. The residue is chromatigraphically purified three times over silica gel with $CHCl_3/CH_3OH$ (95/5, 90/10 and 90/10). An amorphous solid with a MP of 71–74° C. remains after the removal of the solvent; yield: 0.8 g (13%).

$C_{26}H_{27}N_3O_2$ (413.5); IR-Spectrum (KBr): ν(NH) 3370 $cm^{-1}$; ν(C=O) 1655, 1540 $cm^{-1}$; ν(C=C) 1620 $cm^{-1}$; $^1$H-NMR-Spectrum ($CDCl_3$): 1.70–2.30 (2H, m, morpholine); 2.55–2.90 (2H, m, morpholine); 3.00–3.35 (1H, m, morpholine); 3.50–4.00 (4H, m, CONHC$\underline{H}_2$, morpholine); 4.20 (1H, $Ar_2CH$); 6.00–6.25 (1H, m, NH); 6.47 (1H, d, CH=C$\underline{H}$CO, J=15.7 Hz); 4.36 (1H, $Ar_2CH$); 7.60 (1H, d, CH=C$\underline{H}$CO, J=15.7 Hz); 7.00–7.55 (11H, m, Ar, Py); 7.60 (1H, d, C$\underline{H}$=CHCO, J=15.7 Hz); 7.65–7.90 (1H, m, Py); 8.50–8.70 (1H, m, Py); 8.70–8.80 (1H, m, Py).

Example 26

N-{4-[1-(9-oxo-9H-Fluorene-4-carbonyl)-piperidine-4-yl]-butyl}-3-(pyridin-3-yl)-acrylamide (Substance 277)

5.0 g (20.0 mmol) 95% 9-fluorene-1-acyl chloride were dissolved in 70 ml abs. dichloromethane and 6.5 g (18.2 mmol) N-[4-(piperidine-4-yl)-butyl]-3-(pyridine-3-1)-acrylamide dihydrochloride (substance 22) are added. The mixture is cooled to ca. 0° C. under moisture exclusion and 4.0 g (40.0 mmol) TEA dissolved in 10 ml abs. dichloromethane is added dropwise. The batch is stirred without cooling at RT overnight. In the work up, 150 ml 10% sodium hydroxide solution are added to the reaction solution and extracted by shaking. The organic phase is washed with 100 ml water, dried over sodium sulfate and the solution is removed under vacuum. The residue is pre-purified over silica gel with $CHCl_3/CH_3OH$ (96/4 to 95/5) and subsequently purified by flash chromatography with CHCl$_3$/CH$_3$OH (95/5). The product remains as a yellow, vitreous solid with MP of 80–82° C. after removal of the solvent, yield 2.3 g (25%)

C$_{31}$H$_{31}$N$_3$O$_3$ (493.6);

IR-Spectrum (KBr): ν(NH) 3320 cm$^{-1}$; ν(C=O) 1730, 1640 cm$^{-1}$; ν(C=C) 1620 cm$^{-1}$;

$^1$H-NMR-Spectrum (CDCl$_3$): 0.70–2.05 (11H, m, piperidine, piperidine-CH$_2$)$_3$); 2.60–3.80 (5H, m, piperidine, CONHC$\underline{H}_2$); 4.70–5.05 (1H, piperidine); 5.85–6.20 (1H, m, NH); 6.47 (1H, d, CH=C$\underline{H}$O J=15.7 Hz); 7.15 –7.90 (10H, m, Ar, PyCH=C$\underline{H}$CO, J=15.7 Hz); 8.50–8.65 (1H, m, Py); 8.65–8.85 (1H, m, Py).

Example 27

N-[3-(1-Benzylpiperidine-4-yloxy)-propyl]-3-(pyridin-3-yl)-acrylamide (Substance 55)

2.4 g (16.2 mmol) 3-(3-pyridyl)-acrylic acid and 2.3 g (16.2 mmol) TEA were suspended in 50 ml abs. tolueneand a solution of 1.5 ml (15.5 mmol) chloroformic ethyl ester in 20 ml abs. tolueneis added dropwise under moisture exclusion and gentle cooling. This yellow suspension is stirred two hours at RT and then a solution of 3.5 g (14.1 mmol) 3-(1-benzylpiperidine-4-yloxy)-propylamine in 20 ml abs. tolueneis added dropwise. The mixture is stirred at RT and subsequently extracted by shaking in the heat three times with 10 ml water, 2M sodium hydroxide solution and again with water, respectively. The organic phase is concentrated under vacuum and the orange colored, oily residue is chromatographically purified twice over silica gel with CHCl$_3$/CH$_3$OH/NH$_4$OH (90/9/1 and 95/5/0 to 90/10/0) and crystallized twice from 10 ml acetic acid ethyl ester. Colorless crystals with a MP of 100–102° C. were recovered; yield: 1.9 g (35%).

C$_{23}$H$_{29}$N$_3$O$_2$ (379.5). IR-Spectrum (KBr): ν(NH) 3290 cm$^{-1}$; ν(C=O) 1650, 1530 cm$^{-1}$; ν(C=C) 1610 cm$^{-1}$; $^1$H-NMR-Spectrum (CDCl$_3$): 1.50–2.45 (8H, m, piperidine, C—CH$_2$—C); 2.70–3.00 (2H, m, piperidine); 3.25–3.80 (7H, m, piperidine, CONHC$\underline{H}_2$, Ar—O—CH$_2$); 6.54 (1H, d, CH=C$\underline{H}$CO, J=15.7 Hz); 7.25–7.50 (6H, m, Ar, Py); 7.69 (1H, d, CH=C$\underline{H}$CO, J=15.7 Hz); 7.80–8.00 (1H, m, Py); 8.60–8.75 (1H, m, Py); 8.75–8.90 (1H, m, Py).

Example 28

N-[4-(1-Benzoylpiperidine-3-yl)-butyl]-3-(pyridin-3-yl)-acrylamide (Substance 56)

Production occurred analogously to Example 27.

Batch size: 2.6 g (17.4 mmol) 3-(3-pyridyl)-acrylic acid, 1.6 ml (19.0 mmol) oxalyl chloride and 3.9 g (15.8 mmol) 4-(1-benzlypiperidine-3-yl)-butylamine in 100 ml abs. dichloromethane.

The reaction time is increased to 6 hours at RT. In the work up, the batch is washed with 50 ml sodium hydroxide solution and the aqueous phase is extracted with 50 ml dichloromethane. The combined organic phases are concentrated under vacuum and the residue is chromatigraphically purified twice over silica gel with CHCl$_3$/CH$_3$OH (93/7 and 95/5), subsequently further purified by flash chromatography with CHCl$_3$/CH$_3$OH, 95/5 and 97/3) and crystallized from 5 ml acetic acid ethyl ester. Colorless crystals with a MP of 80–82° C. were recovered; yield 0.9 g (15%).

C$_{24}$H$_{31}$N$_3$O (377.5); IR-Spectrum (KBr): ν(NH) 3300 cm$^{-1}$; ν(C=O) 1650, 1530 cm$^{-1}$; ν(C=C) 1610 cm$^{-1}$. $^1$H-NMR-Spectrum (CDCl$_3$): 1.00–2.10 (13H, m, piperidine, piperidine-CH$_2$)$_3$); 2.65–2.95 (2H, m, piperidine); 3.37 (2H, dt, CONHC$\underline{H}_2$, J=6.5 Hz, J=12.7 Hz); 3.50 (2H, s, Ar—CH$_2$); 5.65–5.95 (1H, m, NH); 6.46 (1H, d, CH=C$\underline{H}$CO, J=15.6 Hz); 7.10–7.40 (6H, m, Ar, Py); 7.62 (1H, d, CH=C$\underline{H}$CO, J=15.6 Hz); 7.65–7.90 (1H, m, Py); 8.50–8.65(1H, m, Py); 8.70–8.80 (1H, m, Py);

Example 29

N-[4-(1-tert-Butoxycarbonylpiperidine-4-yl)-butyl]-3-(pyridin-3-yl)-acrylamide (Substance 367)

Production occurred analogously to Example 22. TEA is also added dropwise with the addition of the amine.

Batch size 16.4 g (110 mmol) 3-(3-pyridyl)-acrylic acid, 18.9 g (150 mmol) oxalyl chloride and 25.6 g (100 mmol) 4-(1-tert-butoxycarbonylpiperidine-4-yl)-butylamine and 10.1 (100 mmol) TEA in 300 ml abs. dichloromethane.

In the work up, 100 ml 10% sodium hydroxide solution are added to the reaction solution. The aqueous phase is extracted with 30 ml dichloromethane. The combined organic phases are washed twice, each with 25 ml water and the solution is removed under vacuum. The residue is dissolved in CHCl$_3$/CH$_3$OH (90/10) and filtered through a thin silica gel layer. The crude product remains as a red oil after the revomal of the solvent (44.0 g). For purification this is chromatographed with CHCl$_3$/CH$_3$OH, (95/5) on a silica gel, yield 26.5 g (68%) as a yellow viscous oil.

C$_{22}$H$_{33}$N$_3$O$_3$ (387.50);

IR-Spectrum (KBr); ν(NH) 3250 cm$^{-1}$; ν(C=O) 1670, 1540 cm$^{-1}$; ν(C=C) 1600 cm$^{-1}$;

$^1$H-NMR-Spectrum (CDCl$_3$); 0.80–1.90 (20H, m, piperidine, piperidine-CH$_2$)$_3$, tert butyl); 2.30–2.90 (2H, m, piperidine); 3.10–3.60 (2H, m, piperidine); 3.80–4.30 (2H, m, CONHC$\underline{H}_2$); 6.15–6.55 (1H, m, NH); 6.43 (1H, d, CH=C$\underline{H}$CO, J=15.6 Hz); 3.50 (2H, s, Ar—CH$_2$); 8.35–8.55 (2H, m, Py); 8.55–8.70 (1H, m, Py).

Example 30

N-[4-(Piperidine-4-yl)-butyl]-3-(pyridin-3-yl)-acrylamide Dihydrochloride (Substance 22 as Dihydrochloride)

44.0 g (<113.5 mmol) crude N-[4-(1-tert-butoxycarbonylpiperidine-4-yl)-butyl]-3-pyridin-3-yl)-acrylamide (substance 367) are dissolved in 400 ml ethanol and added to 26.0 ml concentrated hydrochloric acid. The mixture is heated to boiling for three hours and the solvent is removed under vacuum after cooling. The yellow residue is crystallized from 500 ml isopropanol. Beige colored crystals with a MP of 178–188° C. were recovered; yield: 32.6 g (90%).

C$_{17}$H$_{25}$N$_3$O$_2$ (360.3). IR-Spectrum (KBr): ν(NH) 3260 cm$^{-1}$; ν(C=O) 1670, 1545 cm$^{-1}$; ν(C=C) 1630 cm$^{-1}$. $^1$H-NMR-Spectrum (CDCl$_3$): 0.95–1.95 (11H, m, piperidine, piperidine CH$_2$)$_3$); 2.60–3.00 (2H, m, piperidine); 3.00–3.40 (4H, m, piperidine, CONHC$\underline{H}_2$); 6.73 (1H, d, CH=C$\underline{H}$CO, J=15.9 Hz); 7.41 (1H, d, CH=C$\underline{H}$CO, J=15.9 Hz); 7.80–8.00 (1H, m, Py); 8.50–8.65 (2H, m, Py); 8.65–8.90(1H, m, Py);

Further examples of the synthesized compounds are listed in the following Table 2, giving the structural features and melting points, for the further illustration of the compounds used according to the invention with the above characterized pharacological activities.

TABLE 2

Prepared compounds of formula (I)

| Nr | R¹ | A | D-E-G | MP [° C.] (solvent)[1] |
|---|---|---|---|---|
| 2 | H | CH=CH | CH₂-(azetidine)-N-CH(phenyl)(phenyl) | 72–74 (amorph; CHCl₃/MeOH) |
| 5 | H | CH=CH | CH₂CH₂CH₂CH₂-(azetidine)-N-CH(phenyl)(phenyl) | 164–165 (EE) |
| 21 | H | CH₂CH₂ | CH₂CH₂CH₂CH₂-(piperidine)-N·H | 60–62 (CHCl₃/MeOH) |
| 22 | H | CH=CH | CH₂CH₂CH₂CH₂-(piperidine)-N·H | 140–142 (amorph; CH₂Cl₂) |
| 22 | H | CH=CH | CH₂CH₂CH₂CH₂-(piperidine)-N·H | 178–166[2] (iPrOH) |
| 23 | H | CH₂CH₂CH₂CH₂ | CH₂CH₂CH₂CH₂-(piperidine)-N·H | 57–59 (CHCl₃) |
| 24 | H | CH=CH.CH=CH | CH₂CH₂CH₂CH₂-(piperidine)-N·H | 197–202[2] (iPrOH) |
| 44 | H | CH₂CH₂ | CH₂CH₂CH₂CH₂-(piperidine)-N-CH₂-phenyl | 61–63 (iPr₂O) |
| 46 | H | CH=CH | CH₂CH₂CH₂CH₂-(piperidine)-N-CH₂-phenyl | 88–90 (MeCN) |
| 54 | H | CH₂CH₂ | CH₂CH₂CH₂O-(piperidine)-N-CH₂-phenyl | 55–57 (BuCl) |

TABLE 2-continued

Prepared compounds of formula (I)

| Nr | R¹ | A | D-E-G | MP [° C.] (solvent)[1] |
|---|---|---|---|---|
| 55 | H | CH=CH | CH₂CH₂CH₂O-piperidin-4-yl, N-CH₂-phenyl | 100–102 (EE) |
| 56 | H | CH=CH | 3-(CH₂CH₂CH₂CH₂)-piperidin-1-yl, N-CH₂-phenyl | 80–82 (EE) |
| 74 | H | CH₂CH₂ | CH₂CH₂CH₂CH₂-piperidin-4-yl, N-CH₂-biphenyl | 125 (EE) |
| 75 | H | CH=CH | CH₂CH₂CH₂CH₂-piperidin-4-yl, N-CH₂-biphenyl | 147–149 (MeCN) |
| 80 | H | CH₂CH₂ | CH₂CH₂CH₂CH₂-piperidin-4-yl, N-CH₂-anthracen-9-yl | 133–135 (EtOH) |
| 81 | H | CH=CH | CH₂CH₂CH₂CH₂-piperidin-4-yl, N-CH₂-anthracen-9-yl | 162–164 (EtOH) |
| 83 | H | CH₂CH₂ | CH₂CH₂CH₂CH₂-piperidin-4-yl, N-CH(phenyl)(cyclohexyl) | 109–110 (MeCN) |

TABLE 2-continued
Prepared compounds of formula (I)
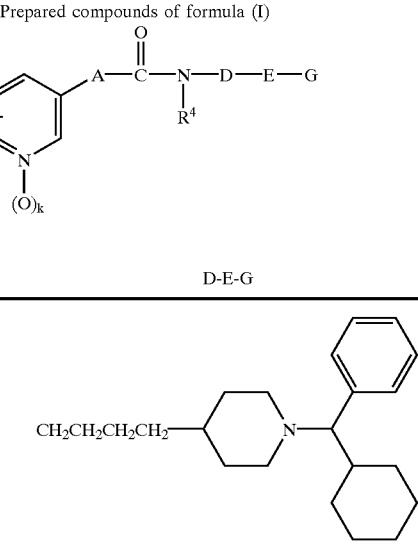
| Nr | R¹ | A | D-E-G | MP [° C.] (solvent)[1] |
|---|---|---|---|---|
| 84 | H | CH=CH | 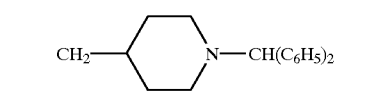 | 143–145 (MeCN) |
| 89 | H | CH=CH | 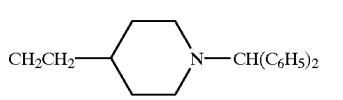 | 135–136 (EE) |
| 95 | H | CH=CH | 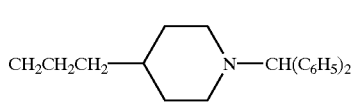 | 141–143 (EE/PE) |
| 96 | H | $CH_2CH_2$ | 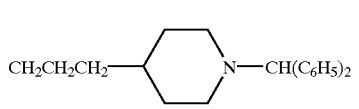 | 109–110 (BuCl) |
| 97 | H | CH=CH | 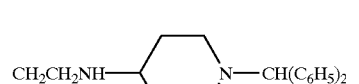 | 110–113 (EE) |
| 98 | H | $CH_2CH_2$ | 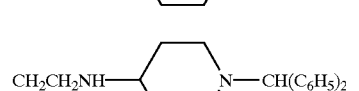 | 162–171[3] (iPrOH) |
| 99 | H | CH=CH | 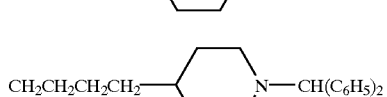 | 139–140 (EE) |
| 100 | H | $CH_2CH_2$ | 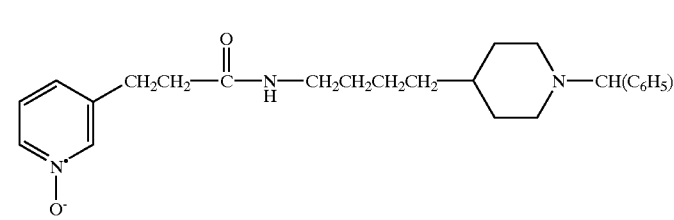 | 139 (EE) |
| 101 | | | 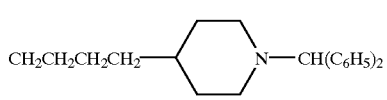 | Harz[4] |
| 102 | 2-OH | $CH_2CH_2$ | | 135–136 (MeCN) |

TABLE 2-continued

Prepared compounds of formula (I)

| Nr | R[1] | A | D-E-G | MP [° C.] (solvent)[1] |
|---|---|---|---|---|
| 103 | 6-CH$_3$O | CH$_2$CH$_2$ | CH$_2$CH$_2$CH$_2$CH$_2$—piperidine—N—CH(C$_6$H$_5$)$_2$ | 135–137 (BuCl) |
| 104 | H | CH=CH | CH$_2$CH$_2$CH$_2$CH$_2$—piperidine—N—CH(C$_6$H$_5$)$_2$ | 156 (EE) |
| 104 | H | CH=CH | CH$_2$CH$_2$CH$_2$CH$_2$—piperidine—N—CH(C$_6$H$_5$)$_2$ | 118–120[5] (Acelon) |
| 104 | H | CH=CH | CH$_2$CH$_2$CH$_2$CH$_2$—piperidine—N—CH(C$_6$H$_5$)$_2$ | 163[4] (iPrOH) |
| 105 | (pyridine N-oxide with CH=CH—C(O)NH—CH$_2$CH$_2$CH$_2$CH$_2$—piperidine—N—CH(C$_6$H$_5$)$_2$) | | | ca. 205 (Zers.) (CHCl$_2$) |
| 110 | 2-Cl | CH=CH | CH$_2$CH$_2$CH$_2$CH$_2$—piperidine—N—CH(C$_6$H$_5$)$_2$ | 136–137 (BuCl) |
| 111 | 6-C$_2$H$_5$S | CH=CH | CH$_2$CH$_2$CH$_2$CH$_2$—piperidine—N—CH(C$_6$H$_5$)$_2$ | 158–160 (EE) |
| 112 | 6-C$_6$H$_5$O | CH=CH | CH$_2$CH$_2$CH$_2$CH$_2$—piperidine—N—CH(C$_6$H$_5$)$_2$ | 134–135 (BuCl) |
| 115 | H | CH=C(CH$_3$) | CH$_2$CH$_2$CH$_2$CH$_2$—piperidine—N—CH(C$_6$H$_5$)$_2$ | 132 (MeOH) |
| 116 | H | CH$_2$CH(C$_6$H$_5$) | CH$_2$CH$_2$CH$_2$CH$_2$—piperidine—N—CH(C$_6$H$_5$)$_2$ | 58–60 (BuCl) |
| 117 | H | CH=C(C$_6$H$_5$) | CH$_2$CH$_2$CH$_2$CH$_2$—piperidine—N—CH(C$_6$H$_5$)$_2$ | 139–140 (MeCN) |

TABLE 2-continued

Prepared compounds of formula (I)

Structure: Pyridine ring with R¹ substituent and N-oxide (O)ₖ, connected via A to C(=O)−N(R⁴)−D−E−G

| Nr | R¹ | A | D-E-G | MP [° C.] (solvent)[1] |
|---|---|---|---|---|
| 122 | | 3-pyridyl-CH₂CH₂− (R⁴ = CH₂CH₃) | −N(CH₂CH₃)−CH₂CH₂CH₂CH₂−[piperidine]−N−CH(C₆H₅)₂ | 72–74 (BuCl/PE) |
| 123 | | 3-pyridyl-CH=CH− (trans) (R⁴ = CH₂CH₃) | −N(CH₂CH₃)−CH₂CH₂CH₂CH₂−[piperidine]−N−CH(C₆H₅)₂ | 115–117 (iPrOH/iPr₂O) |
| 124 | | 3-pyridyl-CH=CH− (trans) (R⁴ = CH₂CH=CH₂) | −N(CH₂CH=CH₂)−CH₂CH₂CH₂CH₂−[piperidine]−N−CH(C₆H₅)₂ | 94–95 (EE) |
| 129 | H | OCH₂ | CH₂CH₂CH₂CH₂−[piperidine]−N−CH(C₆H₅)₂ | 103–105 (EE) |
| 131 | H | CH₂CH₂CH₂CH₂ | CH₂CH₂CH₂CH₂−[piperidine]−N−CH(C₆H₅)₂ | 109 (EE) |
| 132 | H | CH=CH—CH=CH | CH₂CH₂CH₂CH₂−[piperidine]−N−CH(C₆H₅)₂ | 164–166 (MeCN) |
| 133 | H | CH₂NHCH₂CH₂ | CH₂CH₂CH₂CH₂−[piperidine]−N−CH(C₆H₅)₂ | 138–140[3] (iPrOH) |
| 134 | H | CH₂N(CHO)CH₂CH₂ | CH₂CH₂CH₂CH₂−[piperidine]−N−CH(C₆H₅)₂ | Harz[4] |
| 142 | H | CH₂CH₂ | CH₂CH₂CH₂CH₂CH₂−[piperidine]−N−CH(C₆H₅)₂ | 112–114 (MeCN) |
| 143 | H | CH=CH | CH₂CH₂CH₂CH₂CH₂−[piperidine]−N−CH(C₆H₅)₂ | 150–152 (iPrOH) |
| 147 | H | CH=CH | CH₂CH₂NH−C(=O)−O−[piperidine]−N−CH(C₆H₅)₂ | 178–180 (EE) |

TABLE 2-continued
Prepared compounds of formula (I)
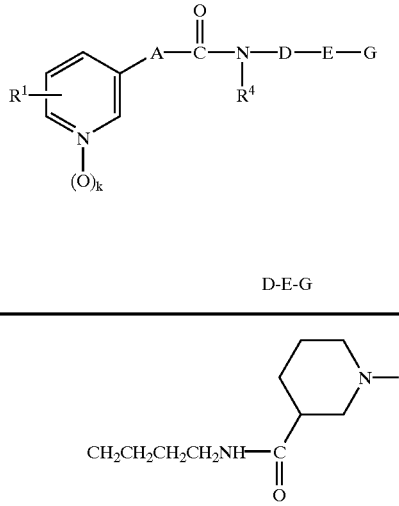
| Nr | R[1] | A | D-E-G | MP [° C.] (solvent)[1] |
|---|---|---|---|---|
| 150 | H | CH$_2$CH$_2$ | 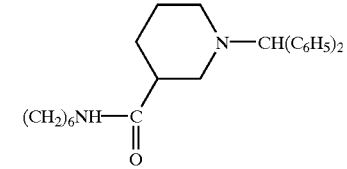 | 159–161 (MeCN) |
| 153 | H | CH$_2$CH$_2$ | 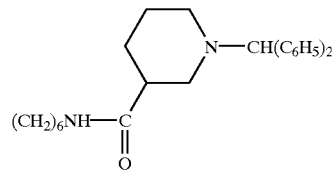 | 76–78 (MeCN) |
| 154 | H | CH=CH | 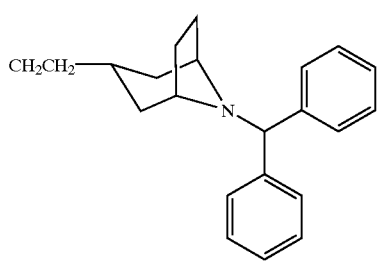 | 129–131 (MeCN) |
| 165 | H | CH=CH | 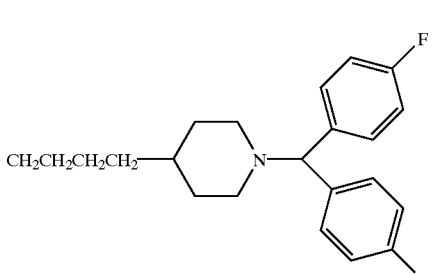 | 190–192 (MeCN) |
| 171 | H | CH=CH |  | 108 (EE) |

TABLE 2-continued

Prepared compounds of formula (I)

| Nr | R¹ | A | D-E-G | MP [° C.] (solvent)[1] |
|---|---|---|---|---|
| 174 | H | CH=CH | CH₂CH₂CH₂CH₂-piperidine-N-CH(4-F-C₆H₄)(4-F-C₆H₄) | 79–81 (PE) |
| 185 | H | CH₂CH₂ | CH₂CH₂CH₂CH₂-piperidine-N-CH(2-Cl-C₆H₄)(2-Cl-C₆H₄) | 125 (iPrOH) |
| 186 | H | CH=CH | CH₂CH₂CH₂CH₂-piperidine-N-CH(2-Cl-C₆H₄)(2-Cl-C₆H₄) | 129–131 (EE) |
| 187 | H | CH₂CH₂CH₂CH₂ | CH₂CH₂CH₂CH₂-piperidine-N-CH(2-Cl-C₆H₄)(2-Cl-C₆H₄) | viskoses Ol[4] |
| 195 | H | CH₂CH₂ | CH₂CH₂CH₂CH₂-piperidine-N-CH(4-COOH-C₆H₄)(C₆H₅) | 82–87 (amorph; CHCl₂/MeOH) |

TABLE 2-continued
Prepared compounds of formula (I)
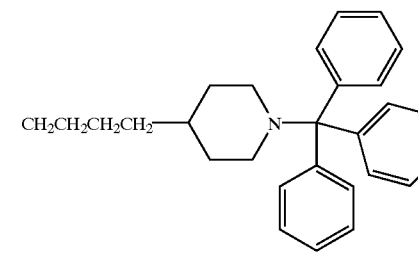
| Nr | R¹ | A | D-E-G | MP [° C.] (solvent)[1] |
|---|---|---|---|---|
| 198 | H | CH=CH | 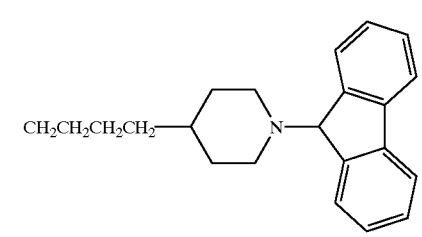 | 150–152 (MeCN) |
| 209 | H | $CH_2CH_2$ | 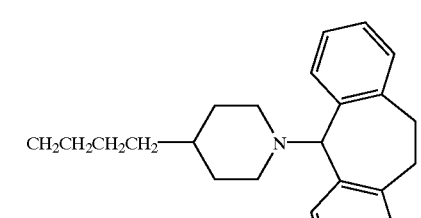 | 131–132 (MeCN) |
| 218 | H | $CH_2CH_2$ | 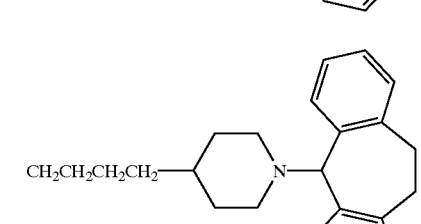 | 113–115 (EE) |
| 219 | H | CH=CH | 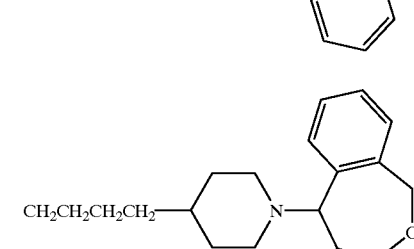 | 125–127 (MeCN) |
| 230 | H | $CH_2CH_2$ | | 110–112 (EE) |

TABLE 2-continued
Prepared compounds of formula (I)
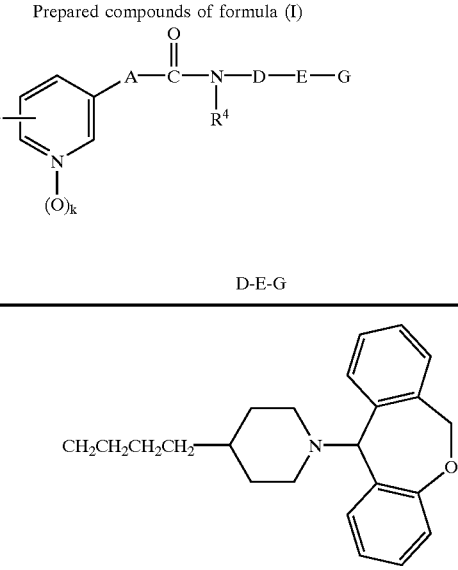
| Nr | R[1] | A | D-E-G | MP [° C.] (solvent)[1] |
|---|---|---|---|---|
| 231 | H | CH=CH | 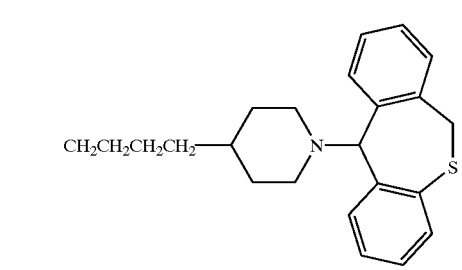 | 139–141 (EE) |
| 233 | H | CH=CH | 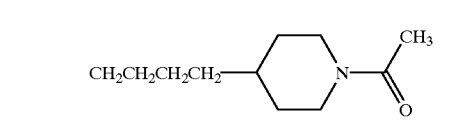 | 89–91 (amorph; CHCl$_2$/MeOH) |
| 239 | H | CH=CH | 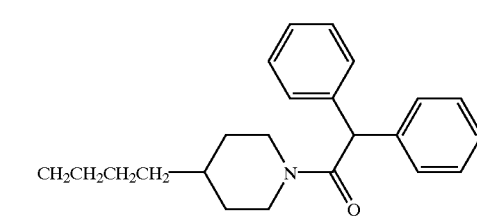 | Harz[4] |
| 252 | H | CH=CH | 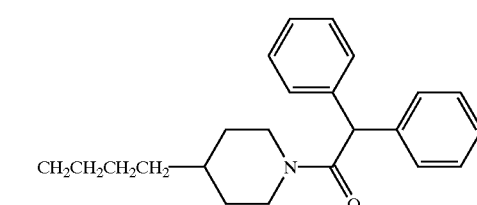 | 161 (EtOH/Et$_2$O) |
| 253 | H | CH=CH.CH=CH | 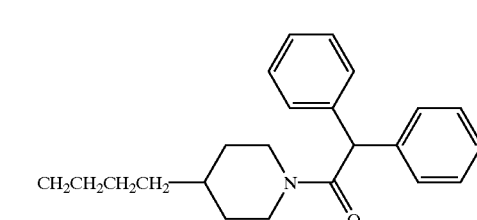 | 77–79 (EE/BuCl) |
| 254 | H | CH=CH | | 105–106 (MeCN/MTBE |

TABLE 2-continued

Prepared compounds of formula (I)

| Nr | R¹ | A | D-E-G | MP [° C.] (solvent)[1] |
|---|---|---|---|---|
| 259 | H | CH=CH | CH₂CH₂CH₂-piperidine-N-C(=O)-phenyl | 100–102 (MeCN) |
| 260 | H | CH=CH.CH=CH | CH₂CH₂CH₂-piperidine-N-C(=O)-phenyl | 133–135 (EE/BuCl) |
| 263 | H | CH₂CH₂ | CH₂CH₂CH₂-piperidine-N-C(=O)-2,6-dichlorophenyl | Harz[4] |
| 266 | H | CH₂CH₂ | CH₂CH₂CH₂CH₂-piperidine-N-C(=O)-biphenyl | 104–105 (BuCl) |
| 269 | H | CH₂CH₂ | CH₂CH₂CH₂-piperidine-N-C(=O)-1-naphthyl | Harz[4] |
| 274 | H | CH₂CH₂ | CH₂CH₂CH₂-piperidine-N-C(=O)-2-naphthyl | Harz[4] |
| 277 | H | CH=CH | CH₂CH₂CH₂CH₂-piperidine-N-C(=O)-(9-oxofluoren-4-yl) | 80–82 (amorph; CHCl₃/MeOH) |
| 280 | H | CH₂CH₂ | CH₂CH₂CH₂CH₂-piperidine-N-C(=O)-2-furyl | 98–99 (BuCl) |

TABLE 2-continued
Prepared compounds of formula (I)
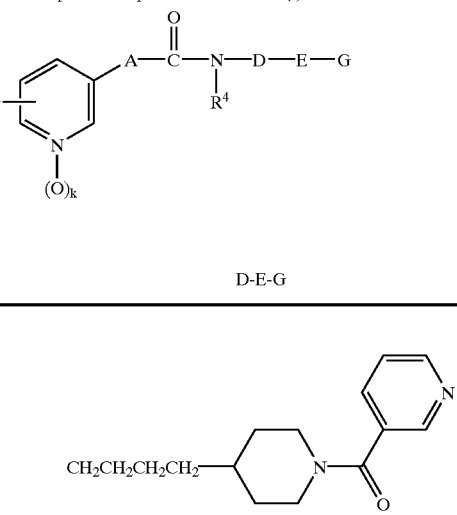
| Nr | R¹ | A | D-E-G | MP [° C.] (solvent)[1] |
|---|---|---|---|---|
| 287 | H | $CH_2CH_2$ | 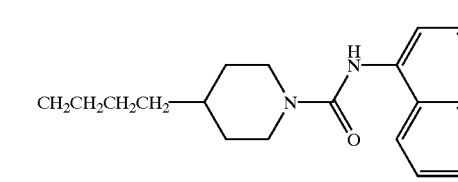 | 85–87 (EtOH) |
| 305 | H | $CH_2CH_2$ | 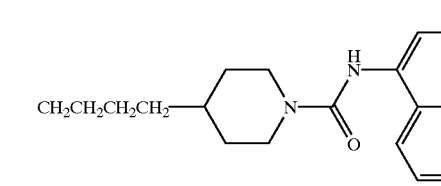 | 143–144 (iPrOH) |
| 306 | H | CH=CH | 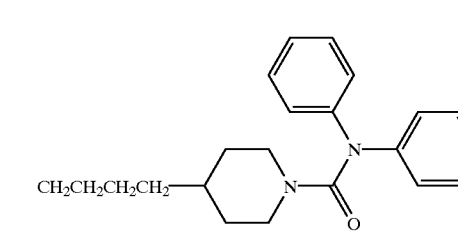 | 198–200 (iPrOH) |
| 315 | H | CH=CH | 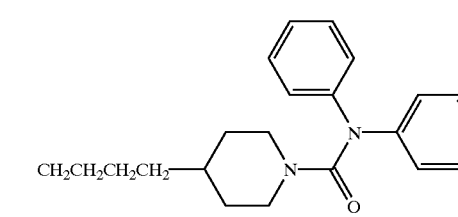 | 132–134 (EE) |
| 316 | H | CH=CH.CH=CH | 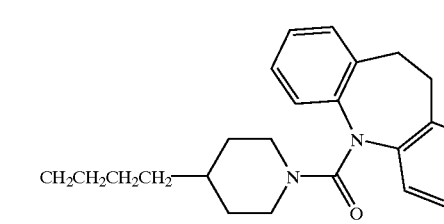 | 146–148 (iPrOH) |
| 324 | H | $CH_2CH_2$ |  | Harz[4] |

TABLE 2-continued

Prepared compounds of formula (I)

| Nr | R[1] | A | D-E-G | MP [° C.] (solvent)[1] |
|---|---|---|---|---|
| 325 | H | CH$_2$CH$_2$CH$_2$CH$_2$ | CH$_2$CH$_2$CH$_2$CH$_2$-[4-piperidinyl]-N-C(=O)-N(10,11-dihydrodibenzo[b,f]azepine) | Harz[4] |
| 333 | H | CH$_2$CH$_2$ | CH$_2$CH$_2$CH$_2$CH$_2$-[4-piperidinyl]-N-SO$_2$-(1-naphthyl) | Harz[4] |
| 337 | H | CH$_2$CH$_2$ | CH$_2$CH$_2$CH$_2$CH$_2$-[4-piperidinyl]-N-SO$_2$-(2-naphthyl) | 103–105 (EE) |
| 338 | H | CH=CH | CH$_2$CH$_2$CH$_2$CH$_2$-[4-piperidinyl]-N-SO$_2$-(2-naphthyl) | 85–87 (amorph; CHCl$_3$/MeOH) |
| 339 | H | CH$_2$CH$_2$CH$_2$CH$_2$ | CH$_2$CH$_2$CH$_2$CH$_2$-[4-piperidinyl]-N-SO$_2$-(2-naphthyl) | 97–98 (EE) |
| 345 | H | CH$_2$CH$_2$ | CH$_2$CH$_2$CH$_2$CH$_2$-[4-piperidinyl]-N-SO$_2$-(5-chloro-3-methylbenzo[b]thiophen-2-yl) | 159–160 (MeCN) |
| 356 | H | CH$_2$CH$_2$ | CH$_2$CH$_2$CH$_2$CH$_2$-[4-piperidinyl]-N-P(=O)(phenyl)$_2$ | 134–135 (iPr$_2$O) |

TABLE 2-continued

Prepared compounds of formula (I)

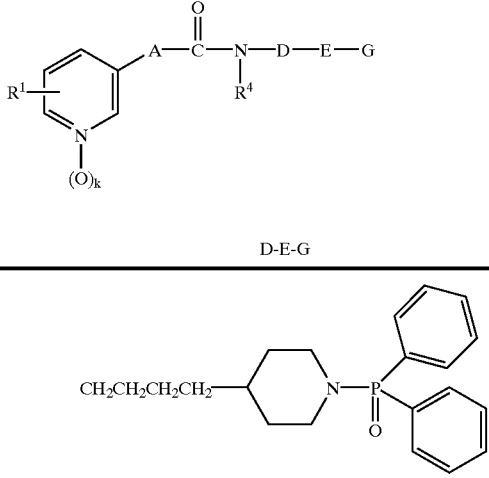

| Nr | R¹ | A | D-E-G | MP [° C.] (solvent)[1] |
|---|---|---|---|---|
| 357 | H | CH=CH | CH₂CH₂CH₂CH₂—[piperidine]—N—P(=O)(phenyl)₂ | 154–155 (EE) |
| 367 | H | CH=CH | CH₂CH₂CH₂CH₂—[piperidine]—N—C(=O)—O—C(CH₃)₃ | Oil[2] |
| 368 | H | CH=CH.CH=CH | CH₂CH₂CH₂CH₂—[piperidine]—N—C(=O)—O—C(CH₃)₃ | 135–136 (EE) |
| 378 | H | CH=CH | [2-methylmorpholine]—N—CH(phenyl)₂ | 71–74 (amorph; CHCl₃/MeOH) |

Table annotation
[1] MeOH = methanol
EE = ethyl acetate
iPrOH = isopropanol
iPr₂O = diisopropyl ether
MeCN = acetonitrile
BuCl = 1-chlorobutane
EtOH = ethanol
PE = petroleum ether
Et₂O = diethyl ether
MTBE = methyl tert-butyl ether
[2] as a dihydrochloride
[3] as a trihydrochloride
[4] purified by column chromatography
[5] as a methanesulfonate In the following, the production of the starting materials necessary for illustration of the reproducibility for providing the compounds used according to the invention is described by means of several examples.

Example 1A

4-{1-[bis(4-fluorophenyl)-methyl]-piperidin-4-yl}-butane-1-ol 20 g (103 mmol) 4-piperidin-4-yl-butan-1-ol hydrochloride are suspended in 70 ml 3,4-dihydro-2H-pyrane and added to 1.0 g pyridinium tosylate. The mixture is stirred for two days at RT. After addition of 5 g potassium carbonate, this is concentrated under vacuum to dryness. The resulting 4-[4-tetrahydropyran-2-yloxy)-butyl]-piperidine is dissolved without further purification in 100 ml acetonitrile and added to 25.1 g (105 mmol) bis-(4-fluorophenyl)-chloromethane, 30 g (217 mmol) potassium carbonate and 5.0 g (30 mmol) potassium iodide and stirred for four days at RT. The mixture is filtered and the solvent is removed under vacuum. The resulting 1-[bis-(4-fluorophenyl)- methyl]-4-[4-(tetrahydropyran-2-yloxy)-butyl]-piperldine is dissolved without further purification in 150 ml methanol, added to enough 6 M methanolic hydrochloric acid until the pH of the mixture is acidic and left to stand for two days at RT. Subsequently, the solvent is drawn off under vacuum and the residue is dispersed between sodium hydroxide solution and acetic acid ethyl ester. The aqueous solution is extracted three times with acetic acid. The combined organic phases are dried over sodium sulfate and the residue is chromatographically purified over silica gel with $CH_2Cl_2$/$CH_3OH$(99/1 to 94/4). Yield: 23.8 g (63%).

Example 2A 2-(4-{1-[bis(4-Fluorophenyl)-methyl]-piperidin-4-yl}-butyl)-isoindol-1,3-dione 23.1 g (62.5 mmol) 4-{1-[bis(4-fluorophenyl)-methyl]-piperidin-4-yl}-butan-1-ol, 16.4 g (62.5 mmol) triphenylphosphine and 9.2 g (62.5 mmol) phthalimide are suspended in THF and 10.9 g (62.5 mmol) azodicarboxylic acid diethyl ester is added dropwise under a protective atmosphere and light cooling (ca. 15–25° C.). The mixture is stirred for three hours at RT and subsequently the solvent is removed under vacuum. The residue is chromatographically purified over silica gel with $CH_2Cl_2$/$CH_3OH$ (99.5/0.5) Yield: 27.6 g (90%).

Example 3A

4-[1-bis (4-Fluorophenyl)-methylpiperidin-4-yl]-butylamine 27.6 g (56.3 mmol) 2-(4-{1-[bis(4-fluorophenyl)-methyl]-piperidin-4-yl}-butyl)-isoindol-1,3-dione are suspended in 120 ml ethanol and added to 5.6 g (112 mmol) hydrazine hydrate and heated to boiling for four hours. After cooling, the mixture is filtered and the solvent is removed under vacuum. The residue is dispersed between 10% sodium hydroxide solution and acetic acid ethyl ester. The aqueous phase is extracted three times with acetic acid ethyl ester. The combined organic phases are dried over sodium sulfate. The solvent is removed under vacuum and the residue is chromatographically purified over silica gel with $CHCl_3$/$CH_3OH$/$NH_4OH$ (95/5/0 to 90/10/1). Yield: 14.6 g (73%).

Example 4A

4-[1-(10,11-Dihydro-5H-dibenzo[a,d]cyclohepten-5-y)-piperidin-4-yl]-butane-1-ol 26.3 g (<109 mmol) 4-[4-tetrahydropyran-2-yloxy)-butyl]-piperidine (crude product) and 23.3 g (229 mmol) TEA are dissolved in 150 ml acetonitrile and added in portions to 25.0 g (109 mmol) 5-chloro-10,11-dihydro-5H-dibenzo[a,d]cycloheptene under cooling. The mixture is stirred at RT overnight. Subsequently, the solvent is removed under vacuum and the residue is dispersed betweenacetic acid ethyl ester and water. The organic phase is dried over sodium sulfate and the solvent is removed under vacuum. The resulting 1-(10,11-dihydro-5H-dibenzo[a,d]cycloheptene-5-yl)-4-[4-(tetrahydropyran-2-yloxy)-butyl]-piperidine is dissolved without further purification in 200 ml methanol, added to enough 6 M methanolic hydrochloric acid until the pH of the mixture is acidic and stirred for five hours at RT. Subsequently, the solvent is removed under vacuum and the residue is dispersed between 10% sodium hydroxide solution and dichloromethane. The organic phase is dried over sodium sulfate and the solvent is removed under vacuum. The residue is processed further without additional purification. Yield 38.2 g.

Example 5A

2-{4-[1-(10,11-Dihydro-5H-dibenzo[a,d]cyclohepten-5-yl)-piperidin-4-yl]-butyl}-isoindol-1,3-dione Production occurs analogously to Example 2a.

Batch size: 15.0 g (<43 mmol) 4-[1-(10,11-dihydro-5H-dibenzo[a,d]cyclohepten-5-yl)-piperidin-4-yl]-butan-1-ol (crude product), 11.3 g (43.1 mmol) triphenylphosphine, 6.4 g (43.5 mmol) phthalimide and 7.5 g (43.0 mmol) azodicarboxylic acid diethyl ester in 200 ml THF. For purification, this is chromatographed over silica gel first with dichloromethane and then with petroleum ether/acetic acid ethyl ester (10/1 to 5/1). Yield: 12.0 g (57%).

Example 6A

4-[1-(10,11-Dihydro-5H-dibenzo[a,d]cyclohepten-5-yl)-piperidin-4-yl]-butylamine

Production occurs analogously to Example 3a.

Batch size: 11.5 g (24.0 mmol) 2-{4-[1-(10,11-dihydro-5H-dibenzo[a,d]cyclohepten-5-yl)-piperidin-4-yl]-butyl}-isoindol-1,3-dione and 2.4 g (48.0 mmol) hydrazine hydrate in 100 ml ethanol.

For work up, the reaction solution is filtered and the filter cake is dispersed between300 ml acetic acid ethyl ester and 100 ml 10% sodium hydroxide solution. The organic phase is dried over sodium sulfate and the solvent is removed under vacuum. The residue is chromatographically purified over silica gel with $CHCl_3$/$CH_3OH$/TEA (95/5/0 to 94/5/1). Yield: 5.6 g (67%).

Example 7A (1-Diphenylmethylpiperidine-4-yliden)-acetonitrile 2.9 g (97 mmol) 80% sodium hydride are suspended in abs. THF and a solution of 21.5 g (121 mmol) diethyl-(cyanomethyl)-phosphonate in 150 ml abs. THF is added dropwise under light cooling. The mixture is subsequently stirred 30 minutes at RT and then a solution of 26.5 g (100 mmol) N-(diphenylmethyl)4-piperidone in 80 ml abs. THF is added dropwise. The suspension is left to stand overnight and subsequently added to 200 ml acetic acid ethyl ester and 100 ml water. The organic phase is separated and washed with 100 ml water, dried over sodium sulfate and the solvent is removed under vacuum. The residue is chromatographically purified over silica gel with dichloromethane. Yield: 22.7 g (78%).

Example 8A (1-diphenylmethylpiperidine-4-yl)-acetonitrile 9.8 g (33.5 mmol) (1-diphenylmethylpiperidine-4-ylidine)-acetonitrile are dissolved in a mixture of 60 ml dioxane and 70 ml ethanol and added dropwise to 1.5 g palladium (5%) on activated carbon. The mixture is stirred at RT under hydrogen atomosphere until consumption of the theoretical amount of hydrogen to be taken up (ca. 14 hours). The mixture is filtered from the catalyst and the solvent is removed under vacuum. The residue is chromatographically purified over silica gel with $CHCl_3$/$CH_3OH$ (96/4). Yield of yellow oil: 8.4 g (85%).

Example 9A

2-(1-Diphenylmethylpiperidine-4-yl)-ethylamine 2.2 g (58.2 mmol) sodium borohydroxide are suspended in 50 ml abs. THF and cooled to ca. 0° C. under moisture exclusion. 6.7 g (23.1 mmol) (1-diphenylmethylpiperidin-4-yl)-acetonitrile are added and the mixture is subsequently cooled to −5° C. to −10° C. and added dropwise to 1.5 ml (26.7 mmol) 95% sulfuric acid (vigorous foaming). The suspension is left to stand for two days at RT without further cooling. Under renewed cooling to ca. 0° C., 40 ml 2 M sodium hydroxide solution is added dropwise. The aqueous phase is extracted with 30 ml THF and thereafter the combined organic phases are washed twice, each with 30 ml saturated NaCl solution, dried over sodium sulfate and the solution is removed under vacuum. The residue is chromatographically purified over silica gel with $CHCl_3/CH_3OH/N_4OH$ (90/10/1). Yield: 3.9 g (57%).

Example 10A

4-{1-[bis(2-chlorophenyl)-methyl]-piperidin-4-yl}-butyronitrile 20 g (106 mmol) 4-(3-cyanoprop-1-yl)-piperidin hydrochloride, 40.2 g (127 mmol) bis(2-chlorophenyl)-bromomethane and 35.2 g (254 mmol) potassium carbonate are heated to boiling in 90 ml acetone for six hours. After cooling, the mixture is freed from solution under vacuum. The residue is dispersed between 90 ml tolueneand 90 ml water. The aqueous phase is extracted with 10 ml tolueneand the combined organic phases are washed with 10 ml water. The organic phase is concentrated and the residue is chromatographically purified over silica gel with $CHCL_3$. Yield: 11.2 g (27%).

Example 11A

4-{1-[bis(2-chlorophenyl)-methyl]-piperidin-4-yl}-butylamine 8.0 g (20.6 mmol) 4-{1-[bis(2-chlorophenyl)-methyl]-piperidin-4-yl}-butyronitrile are dissolved in 240 ml dioxane/ethanol (1/5) and added to 1.5 g Raney-nickel. The mixture is stirred at RT under hydrogen atmosphere until uptake of the theoretical amount of hydrogen. The reaction solution is filtered from the catalyst and the solvent is removed under vacuum. The residue is dispersed between 100 ml 10% sodium hydroxide solution and 300 ml acetic acid ethyl ester. The organic phase is dried with sodium sulfate and the solvent is removed under vacuum. The resin is processed further without additional purification.

Example 12A

3-(1-Diphenylmethylpiperidin-4-yl)-propan-1-ol 20 g (111 mmol) 3-piperidin-4-yl-propan-1-ol hydrochloride are suspended in 70 ml 3,4-dihydro-2H-pyrane and added to 0.5 g pyridinium tosylate. The mixture is stirred for two days at RT. After addition of 1 g potassium carbonate, this is concentrated under vacuum to dryness. The resulting 4-[3-tetrahydropyran-2-yloxy)-propyl]-piperidine is dissolved in 90 ml acetonitrile without further purification and added to 35 g (135 mmol) diphenyl bromomethane (95%) and 29 g (210 mmol) potassium carbonate and stirred for four days at RT. The mixture is filtered and the solvent is removed under vacuum. The resulting 1-diphenylmethyl-4-[3-(tetrahydropyran-2-yloxy)-propyl]-piperidine is dissolved without further purification in 130 ml methanol and added to 25 ml conc. hydrochloric acid, and the mixture is stirred at RT overnight. Subsequently, the solvent is removed under vacuum and the residue is taken up with 300 ml water and extracted with 300 ml acetic acid ethyl ester. The organic phase is discarded and the aqueous phase is made alkaline with 17 g sodium hydroxide and extracted with 300 g acetic acid ethyl ester. After washing the organic phase with 40 ml water, this is dried over sodium sulfate and the solvent is removed under vacuum: The oil is dried under high-vacuum and processed further without purification. Yield: 22.4 g (65%).

Example 13A

2-[3-(1-Diphenylmethylpiperidine-4-yl)-propyl]-isoindol-1,3-dione 20.3 g (65.6 mmol) 3-(1-diphenylmethylpiperidin-4-yl)-propan-1-ol, 17.2 g (65.6 mmol) triphenylphosphine and 9.7 g (65.6 mmol) phthalimide are suspended in 220 ml THF and a solution of 10.4 ml (65.6 mmol) azodicarbonic acid diethyl ester in 50 ml THF is added dropwise within one hour under protective atmosphere and light cooling (ca. 15–25° C.). After a further three hours, the solvent is removed under vacuum and the residue is crystallized from 60 ml 1-chlorobutane. Yield: 12.9 g (45%).

Example 14A

3-(1-Diphenylmethylpiperidin-4-yl)-propanylamine 12.8 g (29.2 mmol) 2-[3-(1-diphenylmethylpiperidine-4-yl)-propyl]-isoindol-1,3-dione are suspended in 110 ml ethanol and added to 2.2 ml (58.4 mmol) hydrazine hydrate and heated to boiling for three hours. After cooling, the mixture is concentrated under vacuum. The residue is dispersed between 300 ml dichloromethane and 50 ml 10% sodium hydroxide solution. The aqueous phase is extracted twice, each with 200 ml dichloromethane. The combined organic phases are washed twice, each with 20 ml water, and dried over sodium sulfate. The solvent is removed under vacuum and the residue is processed fruther without additional purification. Yield 7.3 g (81%)

Example 15A

4-(1-Diphenylmethylpiperidin-4-yl)-butan-1-ol 120 g (620 mmol) 4-piperidin-4-yl-butan-1-ol hydrochloride are suspended in 400 ml 3,4-dihydro-2H-pyran and added to 1.5 g pyridinium tosylate and 5 ml 8 M methanolic hydrochloric acid. This is stirred for three hours and left to stand at RT overnight. After addition of 5 g potassium carbonate, this is concentrated under vacuum to dryness. The resulting 4-[4-tetrahydropyran-2-yloxy)-butyl]-piperidine is dissolved in 500 ml acetonitrile without further purification and added to 193 g (742 mmol) diphenylmethylbromide (95%) and 160 g (1157 mmol) potassium carbonate and stirred for three days at RT. The mixture is filtered and the filtrate is stirred for one day at RT with a further 20 g (76.8 mmol) diphenylmethylbromide (95%) and 16 g (115.8 mmol) potassium carbonate. The mixture is filtered and the solvent is removed under vacuum The resulting 1-diphenylmethyl-4-[4-(tetrahydropyran-2-yloxy)-butly]-piperldine is dissolved in 700 ml methanol without further purification, added to 120 ml conc. hydrochloric acid, and the mixture is left to stand for two days at RT. Subsequently, the solvent is removed under vacuum and the residue is taken up with 1500 ml water and extracted with 1500 ml acetic acid ethyl ester. The organic phase is discarded and the aqueous phase is adjusted to alkaline with sodium hydroxide and extracted with 700 ml acetic acid ethyl ester. After washing the organic phase with 200 ml water, this is dried over sodium sulfate and the solvent is removed under vacuum. The brown oil is dried under high-vacuum and processed further without purification. Yield: 145 g (72%).

Example 16A

2-[4-(1-Diphenylmethylpiperidin-4-yl)-butyl]-isoindol-1,3-dione 135.0 g (417 mmol) 4-(1-diphenylmethylpiperidin-4-yl)-butan-1-ol, 109.5 g (417 mmol) triphenylphosphine and 61.3 g (417 mmol) phthalimide are suspended in THF and 72.6 g (417 mmol) azodicarboxylic acid diethyl ester are added dropwise within 2½ hours under protective atmosphere and light cooling (ca. 15–25° C.). After a further hour, the solvent is removed under vacuum and the residue is crystallized three times from acetic acid ester (1000 ml, 1200 ml and 1100 ml). Colorless crystals with a MP of 150–152 were recovered. Yield 103 g (54.5%).

Example 17A 4-(1-Diphenylmethylpiperidin-4-yl)-butylamine 88.9 g (196 mmol) 2-[4-(1-diphenylmethylpiperidin-4-yl)-butyl]-isoindol-1,3-dione are suspended in 1000 ml ethanol and added to 22.0 g (440 mmol) hydrazine hydrate and heated to boiling for four hours. After cooling, the mixture is filtered and the solvent is removed under vacuum. The solid residue is distributed together with the filter residue under heat between 300 ml 10% sodium hydroxide solution and 300 ml acetic acid ethyl ester. The aqueous phase is extracted once again with 150 ml warm acetic acid ethyl ester. The combined organic phases are extracted twice, each with 300 ml 10% hydrochloric acid. The combined aqueous phases are adjusted to alkaline with 10% sodium hydroxide solution and extracted twice, each with 400 ml acetic acid ethyl ester. The combined organic phases are washed with 100 ml water and dried over sodium sulfate. The solvent is removed under vacuum, the residue is dried under high-vacuum and further processed without additional purification. Yield of gradually solidifying resin: 63 g (99%).

Example 18A 5-(1-Diphenylmethylpiperidin-4-yl)-pentanitrile 24.9 g (69.2 mmol) 4-(1-diphenylmethylpiperidin-4-yl)-butan-1-ol hydrochloride are suspended in 160 ml abs. dichloromethane and cooled to ca. 0° C. under moisture exclusion. At this temperature, 16.0 g (159 mmol) TEA is first added, and thereafter, a solution of 10.3 g (90.0 mmol) methanesulfonic acid chloride in a little abs dichloromethane is added dropwise. The mixture is subsequently stirred for three hours at RT and then placed in ice water. The organic phase is washed once with 50 ml water, dried over sodium sulfate and the solvent is removed under vacuum. The resulting methanesulfonic acid-4-(1-diphenylmethylpiperidin-4-yl)-butyl ester is dissolved in 120 ml DMF without further purification and added to 7.7 g (158 mmol) sodium cyanide and two drops 15-crown-5 and stirred six hours at 65° C. After cooling, the mixture is poured in ice water. The precipitated solid is drawn off and dried under high-vacuum at 40° C. The solid is processed further without additional purification Yield: 19.9 g (86%).

Example 19A 5-(1-Diphenylmethylpiperidin-4-yl)-pentylamine 19.0 g (57.1 mmol) 5-(1-diphenylmethylpiperidin-4-yl)-pentanitrile are dissolved in 240 ml dioxane/ethanol (1/1) and added to 3.2 g Raney-Nickel. The mixture is stirred at RT under hydrogen atmosphere until uptake of the theoretical amount of hydrogen. The mixture is filtered from the catalyst and the solvent is removed under vacuum. The residue is dispersed between 100 ml water and 250 ml acetic acid ethyl ester. The organic phase is dried with sodium sulfate and the solvent is removed under vacuum The resin is processed further without additional purification. Yield: 17.0 g (88%).

Example 20A 4-(1-tert-Butoxycarbonylpiperidin-4-yl)-butan-1-ol 100 g (458 mmol) 4-piperidin-4-yl-butan-1-ol hydrochloride are dissolved in 120 ml water, added to 216 ml (1550 mmol) TEA and cooled to ca. 5–10° C. 122 g (559 mmol) di-tert-butyl dicarbonate dissolved in 400 ml THF are added dropwise within four hours under further cooling. The mixture is left to stand at RT overnight without further cooling. Subsequently, the THF is largely removed under vacuum and the residue is extracted twice with 300 ml and 200 ml CHCl$_3$ and the combined organic phases are washed twice, each with 20 ml water. The solvent is removed under vacuum, the residue dried under high-vacuum and processed further without additional purification. Yield: 136 g.

Example 21A

2-[4-(1-tert-Butoxycarbonylpiperidin-4-yl)-butyl]-isoindol-1,3-dione 136.0 g (<528 mmol) 4-(1-tert-butoxycarbonylpiperidin-4-yl)-butan-1-ol (crude product), 135.3 g (516 mmol) triphenylphosphine and 75.9 g (516 mmol) phthalimide are suspended in THF and 89.9 g (516 mmol) azodicarboxylic acid diethyl ester are added dropwise within 3 hours under protective atmosphere and light cooling (ca. 15° C.). The mixture is left to stand at RT overnight without further cooling. Subsequently, the solvent is removed under vacuum and the oily residue is dissolved in 500 ml acetic acid ethyl ester and held overnight at 0° C. The sedimented precipitate is filtered and discarded. The solution is concentrated under vacuum and the oily residue is chromatographically purified over silica gel with CHCl$_3$ and crystallized from 200 ml isopropanol after drawing off the solvent. Colorless crystals with a MP of 100–102° C. were recovered; yield: 108.5g (57%).

Example 22A 4-(1-tert-butoxycarbonylpiperidin-4-yl)-butylamine 113.0 g (292 mmol) 2-[4-(1-tert-butoxycarbonylpiperldin-4-yl)-butyl]-isoindol-1,3-dione are dissolved in 600 ml ethanol and added to 29.3 g (585 mmol) hydrazine hydrate are added thereto and heated to boiling for three hours. After cooling the solution, the mixture is filtered and the filtrate is concentrated under vacuum. The residue is distributed under heat between 500 ml tolueneand 500 ml 10% sodium hydroxide solution. The organic phase is washed once with 50 ml 10% sodium hydroxide solution

Example 23A (1-Diphenylmethylazetidin-3-ylmethyl)-amine

A solution of 10 g (40 mmol) 1-diphenylmethylazetidin-3-carbonitrile in 20 ml abs. THF are added dropwise at RT to a suspension of 3.1 g (80 mmol) lithium aluminum hydride in 80 ml abs. THF and stirred overnight, 2 ml ethanol are carefully added to the batch and the batch is filtered. The filtrate is concentrated under vacuum and dispersed between $CHCl_3$ and water. The aqueous phase is extracted twice, each with 50 ml $CHCl_3$, and the combined organic phases are dried over sodium sulfate and the solvent is removed under vacuum. The residue is chromatographically purified over silica gel with $CHCl_3/CH_3OH/NH_4OH$ (90/10/0 to 90/10/1). Yield: 5.6 g (57%) of slowly solidifying resin.

Example 24A 3-(1-Benzylpiperidin-4-yloxy)-propylamine 10.0 g (40.9 mmol) 3-(1-benzylpiperidin-4-yloxy)-propionitrile are dissolved in 100 ml ethanol and added to a spatula tip of Raney-Nickel. The mixture is stirred at RT under hydrogen atmosphere until the uptake of the theoretical amount of hydrogen (ca. 2 days). The mixture is filtered from the catalyst and the solvent is removed under vacuum. The residue is distilled in a ball-pipe apparatus. Yield of colorless oil: 7.5 g (73%)

Example 25A 4-(1-Benzylpiperidin-3-ylidene)-butyronitrile 77.3 g (188.3 mmol) 3-cyanopropyl triphenylphosphonium bromide are suspended in 300 ml tolueneand added to 22.0 g (191.9 mmol) potassium-tert-butylate. The mixture is cooled to ca. 0° C. under moisture exclusion and a solution of 34.6 g (182.8 mmol) 1-benzyl-3-piperidone in 50 ml tolueneare added dropwise under cooling. The batch is left to stand overnight at ca. 0° C., subsequently diluted with 200 ml tolueneand washed twice, each with 100 ml water. The organic phase is extracted with 150 ml half-concentrated hydrochloric acid. Subsequently, the aqueous phase is made basic with 200 ml 10% sodium hydroxide solution and extracted twice, each with 250 ml toluol. The solvent is removed under vacuum and the residue is chromatographically purified over silica gel with $CHCl_3/CH_3OH$ (97/3). After drawing off the solvent, a light brown oil remains which is further processed without additional purification. Yield: 47.4 g (90%).

Example 26A 4-(1-Benzylpiperidin-3-ylidene)-butylamine 8.0 g (33.3 mmol) 4-(1-benzylpiperidin-3-ylidene)-butyronitrile are dissolved in 80 ml ethanol and added to a spatula tip of Raney-Nickel. The mixture is stirred under hydrogen atmosphere until consumption of the theoretical amount of hydrogen to be taken up (ca. 5 days). The mixture is filtered from the catalyst and the solvent is removed under vacuum. The residue is chromatographically purified Voice over silica gel with $CHCl_3/CH_3OH/NH_4OH$ (90/10/1). After drawing off the solvent, a colorless oil remains which is further processed without additional purification. Yield. 3.9 g (47%)

The active ingredients used according to the invention can be processed to the desired medicaments in the form of their acid addition salts, hydrates or solvates individually or in combination with each other or with others, optionally under addition of other active ingredients, for the indications tumor treatment or immunosuppression. In the case of the combination of active ingredients according to the invention with other medicinal forms, these can also optionally be separately present next to each other in the medicine packaging, for example as tablets next to viles, depending on the requirements.

Therefore, further subject-matter of the invention is a medicament with an amount of compounds according to the above defined general formula (I) in combination with the further cytostatic agent, cancerostatic agent, immunosuppressing agent and/or immunomodulatory agent. Therewith, a method for the production of medicaments with an amount of one or more compounds according to formula (I), optionally together with another cytostatic agent or immunosuppressive agent and optionally next to further active ingredients and additives customary and suitable for these indications together with respective pharmaceutically acceptable carriers and adjuvents for providing the finished medical form also falls within the scope of protection according to the invention.

The invention is more closely illustrated in the following by means of the production of respective medicaments suitable for the use according to the invention and the combinations according to the invention as well as by means of a series of examples for various medical forms suitable for the respective indications.

Therapeutic Administration Forms

The production of medicaments with an amount of one or more compounds according to the invention and/or their use in the application according to the invention occurs in the customary manner by means of common pharmaceutical technology methods. For this, the active ingredients as such or in the form of their salts are processed together with suitable, pharmaceutically acceptable adjuvents and carriers to medicinal forms suitable for the various indications and types of application. Thereby, the medicaments can be produced in such a manner that the respective desired release rate is obtained, for example a quick flooding and/or a sustained or depot effect.

Preparations for parenteral use, to which injections and infusions belong, are among the most important systemically employed medicaments for tumor treatment as well as for other indications.

Preferably, injections are administered for the treatment of tumors. These are prepared either in the form of vials or also as so-called ready-to-use injection preparations, for example as ready-to-use syringes or single use syringes in addition to perforation bottles for multiple withdrawals. Administration of the injection preparations can occur in the form of subcutaneous (s.c.), intramuscular (i.m.), intravenous (i.v.) or intracutaneous (i.c.) application. The respective suitable injection forms can especially be produced as solutions, crystal suspensions, nanoparticular or colloid-disperse systems, such as for example, hydrosols.

The injectable formulations can also be produced as concentrates which can be adjusted with aqueous isotonic dilution agents to the desired active ingredient dosage.

Furthermore, they can also be produced as powders, such as for example lyophilisates, which are then preferably dissolved or dispersed immediately before application with suitable diluents. The infusions can also be formulated in the form of isotonic solutions, fat emulsions, liposome formulations, microemuilsions and liquids based on mixed micells, for example, based on phospholipids. As with injection preparations infusion formulations can also be prepared in the form of concentrates to dilute. The injectable formulations can also be applied in the form of continuous infusions as in stationary as well as in out-patient therapy, for example in the form of mini-pumps Albumin, plasma expanders, surface active compounds, organic solvents, pH influencing compounds, complex forming compounds or polymeric compounds can be added to the parenteral medicinal forms, especially as substances for influencing the adsorption of the active ingredients to protein or polymers or also with the aim of decreasing the adsorption of the active ingredient to materials such as injection instruments or packaging materials, for example plastic or glass.

The active ingredients can be bound to nanoparticles in the preparations for parenteral use, for example on finely dispersed particles based on poly(meth)acrylates, polyacetates, polyglycolates, polyamino acids or polyether urethanes. The parenteral formulations can also be constructively modified as depot preparations, for example on the multiple unit principle, where the active ingredients are incorporated in a most finely distributed and/or dispersed, suspended form or as crystal suspensions, or on the single unit principle, where the active ingredient is enclosed in a medicinal form, for example, a tablet or a seed which is subsequently implanted. Often, these implantations or depot medicaments in single unit and multiple unit medicinal forms consist of so-called biodegradable polymers, such as for example, polyether urethanes of lactic and glycolic acid, polyether urethanes, polyamino acids, poly(meth)acrylates or polysaccharides.

Sterilized water, pH value influencing substances, such as for example organic and inorganic acids or bases as well as their salts, buffer substances for setting the pH value, agents for isotonicity, such as for example sodium chloride, monosodium carbonate, glucose and fructose, tensides and/or surface active substances and emulsifiers, such as for example, partial fatty acid esters of polyoxyethylene sorbitan (Tween®) or for example fatty acid esters of polyoxethylene (Cremophor®), fatty oils such as for example peanut oil, soybean oil and castor oil, synthetic fatty acid esters, such as for example ethyl oleate, isopropyl myristate and neutral oil (Miglyol®) as well as polymer adjuvents such as for example gelatin, dextran, polyvinylpyrrolidone, organic solvent additives which increase solubility, such as for example propylene glycol, ethanol, N,N-dimethylacetamide, propylene glycol or complex forming compounds such as for example citrates and urea, preservatives, such as for example hydroxypropyl benzoate and hydroxymethyl benzoate, benzy alcohol, anti-oxidants, such as for example sodium sulfite and stabilizers, such as for example EDTA, are suitable as adjuvents and carriers in the production of preparations for parenteral use.

In suspensions, addition of thickening agents to prevent the settling of the active ingredients from tensides and peptizers, to secure the ability of the sediment to be shaken, or complex formers, such as EDTA, ensues. This can also be achieved with the various polymeric agent complexes, for example with polyethylene glycols, polystyrol, carboxymethylcellulose, Pluronics® or polyethylene glycol sorbitan fate, acid esters. The active ingredient can also be incorporated in liquid formulations in the form of inclusion compounds, for example with cyclodextrins. As further adjuvents, dispersion agents are also suitable. For production of lyophilisates, builders are also used, such as for example mannite, dextran, saccharose, human albumin, lactose, PVP or gelatin varieties.

As long as the active ingredients are not incorporated in the liquid medicinal formulations in the form of a base, they are used in the form of their acid addition salts, hydrates or solvates in the preparations for parenteral use.

A further systemic application form of importance is peroral administration as tablets, hard or soft gelatin capsules, coated tablets, powders, pellets, microcapsules, oblong compressives, granules, chewable tablets, lozenges, gums or sachets. These solid peroral administration forms can also be prepared as sustained action and/or depot systems. Among these are medicaments with an amount of one or more micronized active ingredients, diffusions and erosion forms based on matrices, for example by using fats, wax-like and/or polymeric compounds, or so-called reservoir systems. As a retarding agent and/or agent for controlled release, film or matrix forming substances, such as for example ethylcellulose, hydroxypropylmethylcellulose, poly(meth)acrlate derivatives (for example Eudragit®), hydroxypropylmethylcellulose phthalate are suitable in organic solutions as well as in the form of aqueous dispersions. In this connection, so-called bio-adhesive preparations are also to be named in which the increased retention time in the body is achieved by intensive contact with the mucus membranes of the body. An example of a bio-adhesive polymer is the group of Carbomers®.

For sublingual application, compressives, such as for example non-disintegrating tablets in oblong form of a suitable size with a slow release of active ingredient, are especially suitable. For purposes of a targeted release of active ingredients in the various sections of the gastrointestinal tract, mixtures of pellets which release at the various places are employable, for example mixtures of gastric fluid soluble and small intestine soluble and/or gastric fluid resistant and large intestine soluble pellets. The same goal of releasing at various sections of the gastrointestinal tract can also be conceived by suitably produced laminated tablets with a core, whereby the coating of the agent is quickly released in gastric fluid and the core of the agent is slowly released in the small intestine milieu. The goal of controlled release at various sections of the gastrointestinal tract can also be attained by multilayer tablets. The pellet mixtures with differentially released agent can be filled into hard gelatin capsules.

Anti-stick and lubricant and separating agents, dispersion agents such as flame dispersed silicone dioxide, disintegrants, such as various starch types, PVC, cellulose esters as granulating or retarding agents, such as for example wax-like and/or polymeric compounds on the basis of Eudragit®, cellulose or Cremophor® are used as a further adjuvents for the production of compressives, such as for example tablets or hard and soft gelatin capsules as well as coated tablets and granulates.

Anti-oxidants, sweetening agents, such as for example saccharose, xylite or mannite, masking flavors, aromatics, preservatives, colorants, buffer substances, direct tableting agents, such as for example microcrystalline cellulose, starch and starch hydrolysates (for example Celutab®), lactose, polyethylene glycols, polyvinylpyrrolidone and dicalcium phosphate, lubricants, fillers, such as lactose or starch, binding agents in the form of lactose, starch varieties, such as for example wheat or corn and/or rice starch, cellulose derivatives, for example methyl cellulose, hydroxypropylcellulose or silica, talcum powder, stearates, such as for example magnesium stearate, aluminum stearate, calcium stearate, talc, siliconized talc, stearic acid, acetyl alcohol and hydrated fats are used.

In this connection, oral therapeutic systems constructed especially on osmotic principles, such as for example GIT (gastrointestinal therapeutic system) or OROS (oral osmotic system), are also to be mentioned.

Effervescent tablets or tabs, both of which represent immediately drinkable instant medicinal forms which are quickly dissolved or suspended in water are among the perorally administratable compressives. Among the perorally administratable forms are also solutions, for example drops, juices and suspensions, which can be produced according to the above given method, and can still contain preservatives for increasing stability and optionally aromatics for reasons of easier intake, and colorants for better differentiation as well as antioxidants and/or vitamins and sweeteners such as sugar or artificial sweetening agents. This is also true for inspisated juices which are formulated with water before ingestion. Ion exchange resins in combination with one or more active ingredients are also to be mentioned for the production of liquid ingestable forms.

A special release form consists in the preparation of so-called floating medicinal forms. for example based on tablets or pellets which develop gas after contact with body fluids and therefore float on the surface of the gastric fluid. Furthermore, so-called electronically controlled release systems can also be formulated by which active ingredient release can be selectively adjusted to individual needs.

A further group of systemic administration and also optionally topically effective medicinal forms are represented by rectally applicable medicaments. Among these are suppositories and enema formulations. The enema formulations can be prepared based on tablets with aqueous solvents for producing this administration form. Rectal capsules can also be made available based on gelatin or other carriers.

Hardened fat, such as for example Witepsol®, Massa Estarinum®, Novata®, coconut fat, glycerol-gelatin masses, glycerol-soap-gels and polyethylene glycols are suitable as suppository bases.

For long-term application with a systematic active ingredient release up to several weeks, pressed implants are suitable which are preferably formulated on the basis of so-called biodegradable polymers.

As a further important group of systemically active medicaments, transdermal systems are also to be emphasized which distinguish themselves, as with the above-mentioned rectal forms, by circumventing the liver circulation system and/or liver metabolism. These plasters can be especially prepared as transdermal systems which are capable of releasing the active ingredient in a controlled manner over longer or shorter time periods based on different layers and/or mixtures of suitable adjuvents and carriers. Aside from suitable adjuvents and carriers such as solvents and polymeric components, for example based on Eudragit®, membrane infiltration increasing substances and/ or permeation promoters, such as for example oleic acid, Azone®, adipinic acid derivatives, ethanol, urea, propylglycol are suitable in the production of transdermal systems of this type for the purpose of improved and/or accelerated penetration.

As topically, locally or regionally administration medicaments, the following are suitable as special formulations: vaginally or genitally applicable emulsions, creams, foam tablets, depot implants, ovular or transurethral adminstration installation solutions. For opthalmological application, highly sterile eye ointments, solutions and/or drops or creams and emulsions are suitable.

In the same manner. corresponding otological drops, ointments or creams can be designated for application to the ear. For both of the above-mentioned applications, the adminstration of semi-solid formulations, such as for example gels based on Carbopols® or other polymer compounds such as for example polyvinylpyrolidone and cellulose derivatives is also possible.

For customary application to the skin or also to the mucus membrane, normal emulsions, gels, ointments, creams or mixed phase and/or amphiphilic emulsion systems (oil/water-water/oil mixed phase) as well as liposomes and transfersomes can be named. Sodium algenate as a gel builder for production of a suitable foundation or celluolose derivatives, such as for example guar or xanthene gum, inorganic gel builders, such as for example aluminum hydroxides or bentonites (so-called thixotropic gel builder), polyacrylic acid derivatives, such as for example Carbopol®, polyvinylpyrolidone, microcrystalline cellulose or carboxymethylcellulose are suitable as adjuvents and/or carriers. Furthermore, amphiphilic low and high molecular weight compounds as well as phospholipids are suitable. The gels can be present either as hydrogels based on water or as hydrophobic organogels, for example based on mixtures of low and high molecular paraffin hydrocarbons and vaseline.

Anionic, cationic or neutral tensides can be employed as emulsifiers, for example alkalized soaps, methyl soaps, amine soaps, sulfanated compounds, cationic soaps, high fat alcohols, partial fatty acid esters of sorbitan and polyoxyethylene sorbitan, for example lanette types, wool wax, lanolin, or other synthetic products for the production of oil/water and/or water/oil emulsions.

Hydrophilic organogels can be formulated, for example, on the basis of high molecular polyethylene glycols. These gem-like forms are washable. Vaseline, natural or synthetic waxes, fatty acids, fatty alcohols, fatty acid esters, for example as mono-, di-, or triglycerides, paraffin oil or vegetable oils, hardened castor oil or coconut oil, pig fat, synthetic fats, for example based on acrylic, caprinic, lauric and stearic acid, such as for example Softisan® or triglyceride mixtures such as Miglyol® are employed as lipids in the form of fat and/or oil and/or wax-like components for the production of ointments, creams or emulsions.

Osmotically effective acids and bases, such as for example hydrochloric acid, citric acid, sodium hydroxide solution, potassium hydroxide solution, monosodium carbonate, further buffer systems, such as for example citrate, phosphate, Tris-buffer or triethanolamine are used for adjusting the pH value.

Preservatives, for example such as methyl- or propyl benzoate (parabenes) or sorbic acid can be added for increasing stability.

Pastes, powders or solutions are to be mentioned as further topically applicable forms. Pastes often contain lipophilic and hydrophilic auxiliary agents with very high amounts of fatty matter as a consistency-giving base.

Powders or topically applicable powders can contain for example starch varieties such as wheat or rice starch, flame dispersed silicon dioxide or silica, which also serve as diluents, for increasing flowability as well as lubricity as well as for preventing agglomerates.

Nose drops or nose sprays serve as nasal application forms. In this connection, nebulizers or nose creams or ointments can come to use.

Furthermore, nose spray or dry powder formulations as well as controlled dosage aerosols are also suitable for systemic administeration of the active ingredients.

These pressure and/or controlled dosage aerosols and dry powder formulations can be inhaled and/or insufflated. Administration forms of this type also certainly have importance for direct, regional application in the lung or bronchi and larynx. Thereby, the dry powder compositions can be formulated for example as active ingredient-soft pellets, as an active ingredient-pellet mixture with suitable carriers, such as for example lactose and/or glucose. For inhalation or insufflation, common applicators are suitable which are suitable for the treatment of the nose, mouth and/or pharynx. The active ingredients can also be applied by means of an ultrasonic nebulizing device. As a propellant gas for aerosol spray formulations and/or controlled dosage aerosols. tetrafluoroethane or HFC 134a and /or heptafluoropropane or HFC 227 are suitable, wherein non-fluorinated hydrocarbons or other propellants which are gaseous at normal pressure and room temperature, such as for example propane, butane or dimethyl ether can be preferred. Instead of controlled dosage aerosols, propellant-free, manual pump systems can also be used.

The propellant gas aerosols can also suitably contain surface active adjuvents, such as for example isopropyl myristate, polyoxyethylene sorbitan fatty acid ester, sorbitan trioleate, lecithins or soya lecithin.

For regional application in situ, solutions for installation, for example for transurethral administration in bladder tumors or genital tumors, or for profusion in liver tumors or other organ carcinomas are suitable.

The respective suitable medicinal forms can be produced in accordance with the prescription and procedures based on pharmaceutical-physical fundamentals as they are described for example in the following handbooks and are included in the present inventive subject-matter with respect to the production of the respective suitable medicaments:

Physical Pharmacy (A. N. Martin, J. Swarbrick, A. Cammarata), 2nd Ed., Philadelphia Pa., (1970), German version: Physikalische Pharmazie, (1987), 3rd edition, Stuttgart;

R. Voigt, M. Bornschein, Lehrbuch der pharmazeutischen Technologie, Verlag Chemie, Weinheim, (1984), 5th edition;

P. H. List, Arzneimformenlehre, Wissenschaftliche Verlagsgesellschaft mbH, Stuttgart, (1985), 4th edition;

H. Sucker, P. Fuchs, P. Speiser, Pharmazeutische Technologie, Georg Thieme Verlag, Stuttgart—New York, (1991), 2nd edition;

A. T. Florence. D. Attwood, Physicochemical Principles of Pharmacy, The Maximillan Press Ltd., Hong Kong, (1981);

L. A. Trissel, Handbook on Injectable Drugs, American Society of Hospital Pharmacists, (1994), 8th edition;

Y. W. Chien, Transdermal Controlled Systemic Medications, Marcel Dekker Inc., New York—Basel, (1987);

K. E. Avis, L. Lachmann, H. A. Liebermann, Pharmaceutical Dosage Forms: Parenteral Medications, volume 2, Marcel Dekker Inc., New York—Basel, (1986);

B. W. Müller, Controlled Drug Delivery, Paperback AP7, volume 17, Wissenschaftliche Verlagsgesellschaft mbH, Stuttgart, (1987);

H. Asch, D. Essig, P. C. Schmidt, Technologie von Salben, Suspensionen und Emulsionen, Wissenschaftliche Verlagsgesellschaft mbH, Stuttgart, (1984), H. A. Liebermann, L. Lachman, J. B. Schwartz, Pharmaceutical Dosage forms: Tablets, Volume 1, Marcel Dekker Inc., New York, 2nd Edition (1989);

D. Chulin, M. Deleuil, Y. Pourcelot, Powder Technology and Pharmaceutical Processes, in J. C. Williams, T. Allen, Handbook of Powder Technology, Elsevier Amsterdam—London—New York—Tokyo, (1994), J. T. Carstensen, Pharmaceutical Principles of Solid Dosage Forms, Technomic Publishing Co., Inc., Lancaster—Basel, (1993).

PRODUCTION EXAMPLES

Injection Therapeutics a) Parenteral Solution

| | |
|---|---|
| active ingredient used according to the invention | 5.000 g |
| acid sodium phosphate | 5.000 g |
| sodium tartrate | 12.000 g |
| benzyl alcohol | 7.500 g |
| water for injection purposes | to 1000.000 ml |

The solution is produced according to the customary method, sterilized and filled into 10 ml vials. One vial contains 50 mg of the compound according to the invention.

b) Penteral Solution

| | |
|---|---|
| active ingredient used according to the invention | 1.000 g |
| hydrochloric acid, dilute | 5.000 g |
| sodium chloride | 6.000 g |
| water for injection purposes | to 1000.000 ml |

The solution is produced according to a customary method by stirring; the medicinal form is adjusted to a suitable pH value by acid addition and subsequently filled into 100 ml vials and sterilized. A vial contains 100 mg of the compound according to the invention.

c) Parenteral Dispersion

| | |
|---|---|
| active ingredient used according to the invention | 10.000 g |
| soya lecithin | 20.000 g |
| saturated triglycerides | 100.000 g |
| sodium hydroxide | 7.650 g |
| water for injection purposes | to 1000.000 ml |

The active ingredient(s) used according to the invention is dispersed in the saturated triglycerides. Then the soya lecithin is added under stirring, and subsequent to this, the aqueous solution of sodium hydroxide is added with subsequent homogenization. The dispersion is sterilized and filled into 10 ml vials. A vial contains 50 mg of the compound according to the invention.

d) Biodegradable Parenteral Depot Medicinal Form

| | |
|---|---|
| active ingredient used according to the invention | 10.000 |
| polylactic acid/polygylcolic acid polymer | 70.000 |
| polyvinylpyrrolidone | 0.200 |
| gelatin | 2.000 |
| soya lecithin | 2.000 |
| isotonic sodium chloride solution | to 1000.000 ml |

First, the active ingredient is incorporated into the biodegradable polymer comprising polylactic acid and polyglycolic acid by a suitable method (spray drying, solvent-evaporation or phase separation) and subsequently subjected to a sterilization process. The particles are introduced into a 2-chamber ready-made syringe in which the adjuvent solution, which is also produced in a sterile manner, is filled. The biodegradable microparticles are mixed with the dispersion agent shortly before application and dispersed. The content of a ready-made syringe is measured such that this contains 200 mg of the active ingredient according to the invention.

e) Parenteral Dispersion for Subcutaneous Installation

| | |
|---|---|
| active ingredient used according to the invention | 25,000 g |
| soya lecithin | 25,000 g |
| arachis oil | 400,000 g |
| benzyl alcohol | 50,000 g |
| Miglyole ® | to 1000,000 g |

The active ingredient is dispersed together with soya lecithin and arachis oil. The benzyl alcohol is dissolved in Miglyole® and added to the dispersion. The entire dispersion is sterilized and subsequently filled into vials with 2 ml content. A vial contains 50 mg active ingredient.

f) Parenteral Perfusions Solution

The solution named under example b) can also be used for perfusion of liver for example.

According to need, instead of ampules with injection solution, so-called perforation bottles (vials), which can also be optionally preserved, and infusion solutions with an amount of one or more active ingredients according to the invention can also be made available in the customary manner under addition of buffer substances for adjustment of physiological pH value and/or the isotonicity and/or a best possible suitable pH value for the medicinal form (euhydria) and optional further required nutrients, vitamins, amino acids, stablizers and other necessary adjuvents, possibly in combination with further medicinal agents suitable for the mentioned indications.

2. Solid, Peroral Administration Medicaments a) Tablets

| | |
|---|---|
| active ingredient used according to the invention | 10,000 g |
| lactose | 5,200 g |
| starch, soluble | 1,800 g |
| hydropropylmethylcellulose | 900 g |
| magnesium stearate | 100 g |

The above components are mixed with each other and compacted in a conventional manner, wherein a tablet weight of 180 mg is set. Each tablet contains 100 mg active ingredient. If desired, the tablets obtained in this manner are coated, provided with a film coat and/or enterically coated.

b) Coated Tablet Core

| | |
|---|---|
| active ingredient used according to the invention | 10,000 g |
| flame dispersed silicon dioxide | 500 g |
| corn starch | 2,250 g |
| stearic acid | 350 g |
| ethanol | 3.0 l |
| gelatin | 900 g |
| purified water | 10.0 l |
| talcum | 300 g |

| -continued | |
|---|---|
| magnesium stearate | 180 g |

From these components, a granulate is produced which is pressed to the desired coated tablet cores. Each core contains 50 mg of active ingredient. The core can be further processed in a customary manner to coated tablets. If desired, a gastric fluid resistant or retarding film coat can be applied in a known manner.

c) Drink Suspension in Vials

| | |
|---|---|
| active ingredient used according to the invention | 0.050 g |
| glycerin | 0.500 g |
| sorbite, 70% solution | 0.500 g |
| sodium saccharinate | 0.010 g |
| methyl-p-hydroxybenzoate | 0.040 g |
| aromatic agent | q.s. |
| sterile wasser | q.s. to 5 ml |

The above-mentioned components are mixed in a customary manner to a suspension and filled in a suitable drink vial having 5 ml content.

d) Poorly Soluble Sublingual Tablets

| | |
|---|---|
| active ingredient used according to the invention | 0.030 g |
| lactose | 0.100 g |
| stearic acid | 0.004 g |
| talcum purum | 0.015 g |
| sweetener | q.s. |
| aromatic agent | q.s. |
| rice starch | q.s. to 0.500 g |

The active ingredient is compacted together with the adjuvents under high pressure to sublingual tablets, favorably in oblong form.

e) Soft Gel Capsule

| | |
|---|---|
| active ingredient used according to the invention | 0.050 g |
| fatty acid glyceride mixture (Miglyole ®) | q.s. to 0.500 g |

The active ingredient is impasted together with the fluid carrier mixture and mixed together with further adjuvents suitable for the incapsulation and filled into elastic soft gelatin capsules which are sealed.

f) Hard Gelatin Capsules

| | |
|---|---|
| active ingredient used according to the invention | 0.150 g |
| microcrystalline cellulose | 0.100 g |
| hydroxypropylmethylcellulose | 0.030 g |
| mannite | 0.100 g |
| ethylcellulose | 0.050 g |
| triethyl citrate | 0.010 g |

The active ingredient is mixed together with the adjuvents, microcrystalline cellulose, hydroxypropylmethylcellulose and mannite, wet with granulation liquid and formed into pellets. These are subsequently coated with a solution of ethylcellulose and triethyl citrate in organic solvents in a fluidized-bed apparatus. A hard gelatin capsule contains 150 mg of active ingredient.

3. Topically Administratable Medicinal Forms
a) Hydrophilic Ointment

| | |
|---|---|
| active ingredient used according to the invention | 0.500 g |
| Eucerinum ® anhydricum | 60.000 g |
| microcrystalline wax | 15.000 g |
| vaseline oil | q.s. to 100.000 g |

The above-mentioned adjuvents are melted and further processed together with the active ingredient to an ointment in a customary manner.

b) Lipophilic Ointment

| | |
|---|---|
| active ingredient used according to the invention | 10.000 g |
| propylene glycol | 50.000 g |
| paraffin, liquid | 100.000 g |
| paraffin wax | 100.000 g |
| vaseline | to 1000.000 ml |

The active ingredient(s) used according to the invention is dissolved in propylene glycol at ca. 60° C. At the same time, the lipophilic components are melted at 60–70° C. and subsequently combined with the active ingredient solution. The ointment is emulsified at first at 60–70° C. and subsequently cooled to 35–40° C. under constant emulsification and then filled in 10 g tubes. A tube contains 100 mg of the compound according to the invention.

4. Inhalation Therapeutic

Further subject-matter is a pharmaceutical formulation which is characterized in that it contians an active ingredient (s) used according to the invention as a base or a physiologically acceptable salt thereof together with carriers and/or diluents customary for this and suitable for administration by means of inhalation.

In this connection, particularly suitable physiologically acceptable salts of the active ingredients are, as already illustrated in the synthesis section, acid addition salts derived from inorganic or organic acids such as for example especially hydrochloride, hydrobromide, sulfate, phosphate, maleate, tartrate, citrate, benzoate, 4-methoxybenzoate, 2- or 4-hydroxybenzoate, 4-chlorobenzoate, p-toluolsulfonate, methanosulfonate, ascorbate, salicylate, acetate, formate, succinate, lactate, glutarate, gluconate or tricarballylate.

The administration of the active ingredient(s) used of the invention by means of inhalation occurs according to the invention in conventional ways customary for administrations of this form, for example in the form of a commercial controlled dosage aerosol or in combination with a spacer. In controlled dosage aerosols, a metering valve is delivered with whose help, a dosed amount of the composition is administered. For spraying, the present compositions can be formulated for example as aqueous solutions or suspensions and be administered by means of an atomizer. Aerosol spray formulations in which the active ingredient is either suspended with one or two stabilizers in a propellant as a carrier and/or diluent, for example tetrafluoroethane or HFC 134a and/or heptafluoropropane or HFC 227 can equally be used, whereby however. non-fluorinated hydrocarbons or other propellants which are gaseous at normal pressure and room temperature, such as propane, butane or dimethyl ether, can be preferred. Thereby, propellant-free manual pump systems or dry powder systems as desribed below can also be used.

Suitably, the propellant aerosols can also contain surface active adjuvents. such as for example isopropyl myristate, polyoxyethylene sorbitan fatty acid ester, sorbitan trioleate, lecithins, oleic acid.

For administration by means of inhalation and/or insufflation, the medicaments with an amount of compounds according to the invention can also be formulated in the form of dry powder compositions, for example as active ingredient-soft pellets or as an active ingredient-powder mixture with a suitable carrier, such as for example lactose and/or glucose. The powder compositions can be formulated and administered as single doses or as multiple doses.

The compounds according to the invention are preferably administered by means of a controlled dosage aerosol or in the form of a dry powder dosage formulation, wherein the latter preferably contains glucose and/or lactose as a carrier substance.

As applicators for inhalation of the pharmaceutical formulations containing one or more of the active ingredient(s) used according to the invention, all applicators are generally suitable which are suitable for controlled dosage aerosols and/or a dry powder dosage formulation, such as for example usual applicators for the nose, mouth and or pharynx, or also devices standing under propellant gas for the delivery of a spray (as controlled dosage aerosol or dry powder dosage formulation) as they are also used for inhalations in the nose, mouth and/or pharynx.

A further embodiment can also consist of an aqueous solution of the active ingredient(s) used according to the invention, which also optionally contains further active ingredients and/or additives, which are applied by means of an ultrasound atomizer.

| | Intended dose per stroke | per aerosol % by weight |
|---|---|---|
| a) Controlled Dosage Aerosol | | |
| active ingredient used according to the invention | 0.500 mg | 0.66 |
| stabilizer | 0.075 mg | 0.10 |
| HFC 134a | 75.500 mg | 99.24 |
| b) Controlled Dosage Aerosol | | |
| active ingredient used according to the invention | 0.250 mg | 0.32 |
| Stabilizer | 0.038 mg | 0.05 |
| HFC 227 | 79.180 mg | 99.63 |

In the examples a) and b) the micronized active ingredient is, after previous dispersion in a small amount of the stabilizer, placed in a suspension vessel in which the bulk amount of propellant gas solution is found. The corresponding suspension is dispersed by means of a suitable stirring system (for example high performance mixer or ultrasound mixer) until an ultra-fine dispersion results. The suspension is then continuously held in flux in a filling apparatus suitable for cold propellants or pressure fillings. Alternatively, the suspension can also be produced in a suitable cooled stabilizer solution in HFC 134a/227.

The examples c) to d) describe the composition and production of dosage dry powder formulations.

| c) Dosage-Dry Powder Formulation | mg/dose |
|---|---|
| active ingredient used according to the invention | 0.500 mg |
| d) Dosage-Dry Powder Formulation | |
| active ingredient used according to the invention | 0.500 mg |
| lactose Ph.Eur | to 2.5 mg or to 5.0 mg |
| e) Dosage-Dry Powder Formulation | |
| active ingredient used according to the invention | 0.250 mg |
| lactose Ph.Eur. | to 2.5 mg or to 5.0 mg |

Im example c) the active ingredient is formulated after micronization under addition of steam as pellets with an MMAD between 0,1 and 0,3 mm diameter and brought to use in a multi-dose pox der applicator.

In the examples d) and e) the active ingredient is micronized, thereafter, bulk material is mixed with the lactose in the given amounts, and subsequently, filled in a multi-dose powder inhalator.

In all of the examples set forth above, the active ingredient or the medicinal agent in the form of the respective suitable pharmaceutical acceptable salt and/or acid addition salts can be present, insofar as the base is not preferred in each case.

In the following, the pharmaceutical test results obtained in connection with the newly found indications based, in a representative manner, on the specifically structured compounds falling under formula (I) are reproduced and the experimental results are discussed.

PHARMACEUTICAL EXPERIMENTAL SECTION

1. Growth Inhibition of Human Tumor Cells

The tumor growth inhibiting activity of the substances was determined on human tumor cells in standardized in vitro test systems. In the screening tests, the substances gave $IC_{50}$-values in a concentration range of 0.1 nM bis 10 $\mu$M.

Example:

HepG2 cells plated at a density of 20,000 cells/ml in 12-well plastic dishes. Cultivation occured in Richters IMEM-ZO nutrient medium with 5% fetal calf serum (FCS) in a tissue culture incubator with a gas mixture of 5% $CO_2$ and 95% air at a temperature of 37° C. One day after plating, the culture medium was aspirated from the cells and replaced by fresh medium which contained the respective concentrations of the test substances. For the individual concentrations and the controls without test substances, three-fold batches were done for each. Three days after the beginning of treatment, the medium was again renewed with the test compounds. After six days of substance incubation, the test was ended and the protein amount in the individual wells was determined with the sulforhodamin-B-method (according to P. Skehan et al.: New Colorimetric Cytotoxicity Assay for Anticancer-Drug Screening. J. Natl. Cancer Inst 82: 1107–1112, 1990). The $IC_{50}$-values (defined as that concentration in which the cell growth was inhibited by 50%) was taken from the dose-response curves and given as a comparative measurement for the activity of the test compounds.

The following results were obtained:

| Test substance No. | $IC_{50}$-value [$\mu$M] |
|---|---|
| 46 | 0.04 |
| 75 | 0.2 |
| 81 | 0.07 |
| 84 | 0.02 |
| 95 | 0.03 |
| 97 | 0.08 |
| 104 | 0.01 |
| 143 | 0.02 |
| 171 | 0.05 |
| 174 | 0.05 |
| 186 | 0.02 |
| 198 | 0.08 |
| 219 | 0.02 |

2. Indications

The compounds of formula (1) and their salts permit a therapeutic use in malignant illnesses of humans and animals through their excellent inhibition of the growth of tumor cells. The anti-neoplastic activity of the described substances can be used for prophylactic, adjunct, palliative, and curative treatment of solid tumors, leukemic illnesses and lymphomas as well as for decreasing or preventing metastasis formation in humans and animals. The therapeutic use is possible in the following illnesses for example: gynocoloical tumors, such as of the vulva or the uterus, ovarian carcinomas, testicle tumors, prostate carcinomas, skin cancer, kidney cancer, bladder tumors. esophagus carcinomas. stomach cancer, rectal carcinomas, pancreas carcinomas, thyroid cancer, adrenal tumors, various types of leukemia and lymphomas, Hodgkin's disease. tumor illnesses of the CNS, soft-tissue sarcomas, bone sarcomas, benign and malignant mesotheliomas. especially intestine cancer, liver cancer, breasf cancer, bronchial and lung carcinomas, melanomas, acute and chronic leukemias. Benign papillomatosis tumors can also be inhibited in their growth with the named substances. The broad activity of the new compounds was tested in-vitro according to the method described under point 1. Thereby, the following $IC_{50}$-values were obtained for compound number 104.

| Cell-Line Source | $IC_{50}$-value [$\mu$M] |
|---|---|
| NCI-H69 small cell lung carcinoma | 0.02 |
| WERI-Rb-1 retinoblastoma | 0.008 |
| THP-1 monocytic leukemia | 0.02 |

With respect to the compounds used according to the invention, an independent activity profile is suggested by the findings with the observed activity against the various tumor types. Thus, tumors which are resistant to customary cytostatic agents, for example, respond entirely to these substances. In addition, based on the independent characteristics of the compounds used according to the invention, combinations of these compounds together with known chemotherapeutically used pharmaceuticals, for example cytostatic agents or immunosuppresive agents, etc., are created especially taking a possible complimentation of their properties into consideration, The integration of the presently used compounds with their specific structures in a therapy scheme is successful with one or more substances from the following classes for example: anti-metabolites (for example cytarabine, 5-fluorouracil, 6-mercaptopurine, methotrexate), alkylating agents (for example busulfan, carmustine, cisplatin, carboplatin, cyclophosphamide, dacarbazine, melphalane, thiotepa), DNA-intercalating substances and topoisomerase inhibitors (for example actinomycin D, daunorubicin, doxorubicin, mitomycin C, mitoxantrone, etoposide, teniposide, topotecan, irinotecan), spindle poisons (for example vincristine, navelbin, taxol, taxoter), hormonally active agents (for example tamoxifen, flutamide, formestan, goserelin) or other cytostatic agents with complex modes of action (for example L-asparaginase, bleomycin, hydroxyurea). Resistant tumor cells can be made sensitive again by interaction of the new compounds with a mechanism of resistance for common cytostatic agents (for example P-glycoprotein, MRP, glutathione-S-transferase, metallothionein).

A combination with other therapeutic physical measures or other measures for tumor patients, such as, for example radiotherapy, hyperthermia or immuno therapy is also possible with the compounds used according to the invention. Therefore, further subject-matter under the invention is also combinations of this type in form of new medicaments.

3. Immuno Suppressing Activity

Many anti-tumor agents have not only a cytotoxic effect on tumor cells, but also on the blood cell system. This leads to a weakening of the immune defence, which can, in turn, be specifically employed to suppress the rejection reaction after an organ transplantation for example. Therefore, a use of the main compounds, optionally in combination with other compounds effective for these indications is suitable in diseases such as psoriasis or autoimmune diseases. In order to test the possibility for a therapeutic use in illnesses of this type, the substance activity was tested on freshly isolated lymphocytes as follows:

The spleen of a Swiss mouse served as a lymphocyte source. The lymphocyte population was isolated from the spleen cell suspension over a ficoll gradient and taken up in IMEM-ZO culture medium with 0,1% dextran 70,000 and 2% fetal calf serum. The cells were plated at a density of ca. 500,000 cells/well/ml in a 12-well plate, 1 ml doubly concentrated test substance solution was pipetted per well and this was subsequently incubated in a tissue culture incubator at 37° C. and 5% $CO_2$. After 2 days, a 1 ml-aliquot with 5 μl of the fluorescent dye solutions propidium iodide (8 mg/ml) and 3,3'-dihexyloxacarbocyanin iodide (40 μg/ml) each was added per well, and incubated for 3 minutes at room temperature. Subsequently, 10,000 cells per each sample were measured on a flow-through cytometer and the percentage amount of vital cells in the population was determined. By means of the dose-response curves, $IC_{50}$-values were calculated which were also employed in the following Tables for the characterization of the individual substances:

| Test Substance No. | $IC_{50}$ [μM] |
|---|---|
| 46 | 0.03 |
| 252 | 0.0002 |
| 254 | 0.00008 |
| 306 | 0.002 |
| 315 | 0.00004 |

Hence, the special, independent class of the compounds used according to the invention is also suitable for a combination with known immunosuppressive agents from the class of macrolides, for example cyclosporin A, tacrolimus, rapamycin, or anti-metabolites, for example azathioprin or methotrexate and glucocorticoids. Combinations of this and/or medicaments with an amount of compounds used according to the invention together with known immunosuppressive agents as well as a method for their production represents further subject-matter of the invention.

The invention is in no way limited to the present respective concretely named active ingredient concentrations, dosages, combinations with one or more other cytostatic agents, tumor, inhibitors, cancerostatic agents, immunosuppressive agents or further medicinal agents suitable for the respective specific indications or the type of tumor to treated or immunological illness. ect.

What is claimed is:

1. A method of inhibiting tumor cell growth in a human or animal body comprising administering an effective amount of a pharmaceutical composition, wherein the pharmaceutical composition includes a compound of general formula (I) and pharmaceutically acceptable salts of formula (I)

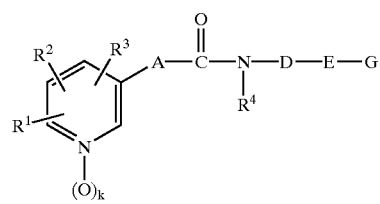

wherein $R^1$ is selected from the group consisting of hydrogen, halogen, cyano, $C_1$–$C_6$-alkyl, $C_3$–$C_6$-alkenyl, $C_3$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkylaminocarbonyl, $C_3$–$C_{13}$-dialkylaminocarbonyl, carboxy, phenyl, phenoxy, phenylthio, $NR^5R^6$, and bridged $R^1R^2$ wherein $R^5$ is selected from the group consisting of hydrogen, $C_1$–$C_6$-alkyl, $C_3$–$C_6$-alkenyl and $C_3$–$C_6$-alkinyl, $R^6$ is selected from the group consisting of hydrogen, $C_1$–$C_6$-alkyl, $C_3$–$C_6$-alkenyl and $C_3$–$C_6$-alkinyl, $R^2$ is selected from the group consisting of hydrogen, halogen, cyano, $C_1$–$C_6$-alkyl, trifluoromethyl, hydroxy, $C_1$–$C_6$-alkoxy, benzyloxy, $C_1$–$C_7$-alkanoyloxy, and bridged $R^1R^2$;

wherein bridged $R^1R^2$ is where $R^1R^2$ are adjacent and form a bridge which is selected from the group consisting of —$(CH_2)_4$— and —$(CH=CH)_2$— and —$CH_2O$—$CR^7R^8$—O—, wherein $R^7$ is selected from the group consisting of hydrogen and $C_1$–$C_6$-alkyl and $R^8$ is selected from the group consisting of hydrogen and $C_1$–$C_6$-alkyl, $R^3$ is selected from the group consisting of hydrogen, halogen, $C_1$–$C_6$-alkyl, trifluoromethyl and $C_1$–$C_6$-hydroxyalkyl;

$R^4$ is selected from the group consisting of hydrogen, $C_1-C_6$-alkyl, $C_3-C_6$-alkenyl, $C_3-C_6$-alkinyl, $C_3-C_6$-cycloalkyl, hydroxy, $C_1-C_6$-alkoxy and benzyloxy;

k is 0 or 1,

A is selected from the group consisting of $C_1-C_6$-alkylene, a substituted $C_1-C_6$-alkylene which is substituted once to three-fold by $C_1-C_3$-alkyl, hydroxy, $C_1-C_3$-alkoxy, fluorine or phenyl, a 1,2-cyclopropylene and an isosterically substituted $C_2-C_6$-alkylene, which has a methylene unit which is isosterically replaced by O, S, $NR^9$, CO, SO or $SO_2$, wherein the isosteric replacement, with the exception of =CO, is not adjacent to the amide group, and wherein $R^9$ is selected from the group consisting of hydrogen, $C_1-C_6$-alkyl, $C_3-C_6$-alkenyl, $C_3-C_6$-alkinyl, $C_1-C_6$-acyl and $C_1-C_6$-alkylsulfonyl, D is selected from $C_1-C_{10}$-alkylene, a substituted $C_1-C_{10}$-alkylene which is substituted once or twice by $C_1-C_6$-alkyl, hydroxy, or $C_1-C_6$-alkoxy, a $C_2-C_{10}$-alkenylene, a substituted $C_2-C_{10}$-alkenylene which is substituted once or twice by $C_1-C_6$-alkyl, hydroxy, $C_1-C_6$-alkoxy, an E double bonded $C_2-C_{10}$-alkenylene which has a double bond to ring E, an E double bonded substituted $C_2-C_{10}$-alkenylene which has a double bond to ring E, a $C_3-C_{10}$-alkinylene, a substituted $C_3-C_{10}$-alkinylene which is substituted once or twice by $C_1-C_6$-alkyl, hydroxy, or $C_1-C_6$-alkoxy, and an isosterically replaced $C_1-C_{10}$-alkylene, $C_2-C_{10}$-alkenylene or $C_3-C_{10}$-alkinylene, having an isosterically replaced group having one to three methylene units which are each isosterically replaced by O, S, $NR^{10}$, CO, SO or $SO_2$, wherein $R^{10}$ has the same meaning as $R^9$, but is selected independently therefrom, E is

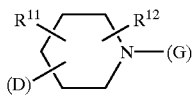

$R^{11}$ is selected from the group consisting of hydrogen, $C_1-C_6$-alkyl, hydroxy, hydroxymethyl, carboxy and $C_2-C_7$-alkoxycarbonyl, and $R^{12}$ is selected from the group consisting of hydrogen, $C_1-C_6$-alkyl and an oxo group adjacent to the nitrogen atom, or $R^{11}$ and $R^{12}$ together form a $C_1-C_3$-alkylene bridge under formation of a bi-cyclic ring system, G is selected from the group consisting of hydrogen, G1, G2, G3, G4 and G5, wherein G1 is

wherein r is an integer from 1 to 3 or 0, s is 0 or 1, $R^{13}$ is selected from the group consisting of hydrogen, $C_1-C_6$-alkyl, $C_3-C_6$-alkenyl, $C_3-C_6$-alkinyl, $C_3-C_8$-cycloalkyl, benzyl, phenyl, anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group, $R^{14}$ has the same meaning as $R^{13}$, but is selected independently thereof, $R^{15}$ is selected from the group consisting of hydrogen, hydroxy, methyl, benzyl, phenyl, anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group, G2 is selected from the group consisting of

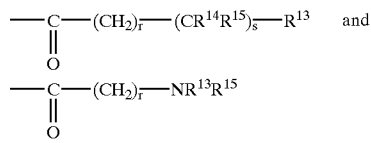

wherein the substituents $R^{13}$ and $R^{15}$ have the above meaning,

G3 is $-SO_2-(CH_2)_rR^{13}$ and

G4 is

wherein $Ar^1$ is selected from the group consisting of phenyl, and naphthyl, $Ar^2$ is selected from the group consisting of phenyl, and naphthyl, and G5 is $-COR^{16}$ wherein $R^{16}$ is selected from the group consisting of trifluoromethyl, $C_1-C_6$-alkoxy, $C_3-C_6$-alkenyloxy, and benzyloxy, and wherein aromatic rings in the substituents $R^1$, $R^2$, $R^4$, $R^{13}$, $R^{14}$, $R^{15}$, $R^{16}$, $Ar^1$ and $Ar^2$ are substituted and unsubstituted, the substituted rings in $R^1$, $R^2$, $R^4$, $R^{13}$, $R^{14}$, $R^{15}$, $R^{16}$, $Ar^1$ and $Ar^2$ having substitutents which are independently selected from halogen, cyano, $C_1-C_6$-alkyl, trifluoromethyl, $C_3-C_8$-cycloalkyl, phenyl, benzyl, hydroxy, $C_1-C_6$-alkoxy, benzyloxy, phenoxy, mercapto, $C_1-C_6$-alkylthio, carboxy, $C_1-C_6$-alkoxycarbonyl, benzyloxycarbonyl, nitro, amino, mono-$C_1-C_6$-alkylamino, di-($C_1-C_6$-alkyl)-amino, and substituted $C_1-C_6$ alkoxy which is entirely or partially substituted by fluorine, wherein two adjacent groups on the aromatic ring may form an additional ring over a methylenedioxy bridge.

2. A method of inhibiting tumor cell growth according to claim 1, wherein the composition is administered by a method selected from the group consisting of subcutaneously, intramuscularly, intravenously, intracutaneous, orally, sublingually, transdermally, topically and combinations thereof.

3. A method of inhibiting tumor cell growth according to claim 1, wherein the method is effective for inhibiting tumors selected from the group consisting of gynacological tumors, ovarian carcinomas, testicle tumors, esophagus carcinomas, stomach cancer, rectal carcinomas, pancreas carcinomas, thyroid cancer, adrenal tumors, leukemia, lymphomas, Hodgkin's disease, CNS tumors, soft-tissue sarcomas, bone sarcomas, benign and malignant mesotheliomas, intestine tumors, liver tumors, breast tumors, bronchial and lung carcinomas, melanomas, benign papillomatosis tumors, and combinations thereof.

4. A method of inhibiting tumor cell growth according to claim 1, wherein the pharmaceutical composition is combined with a compound selected from the group consisting of pharmaceutically acceptable carriers, adjuvants, additives, and mixtures thereof.

5. A method of inhibiting tumor cell growth according to claim 1, wherein DEG is selected from the group consisting of

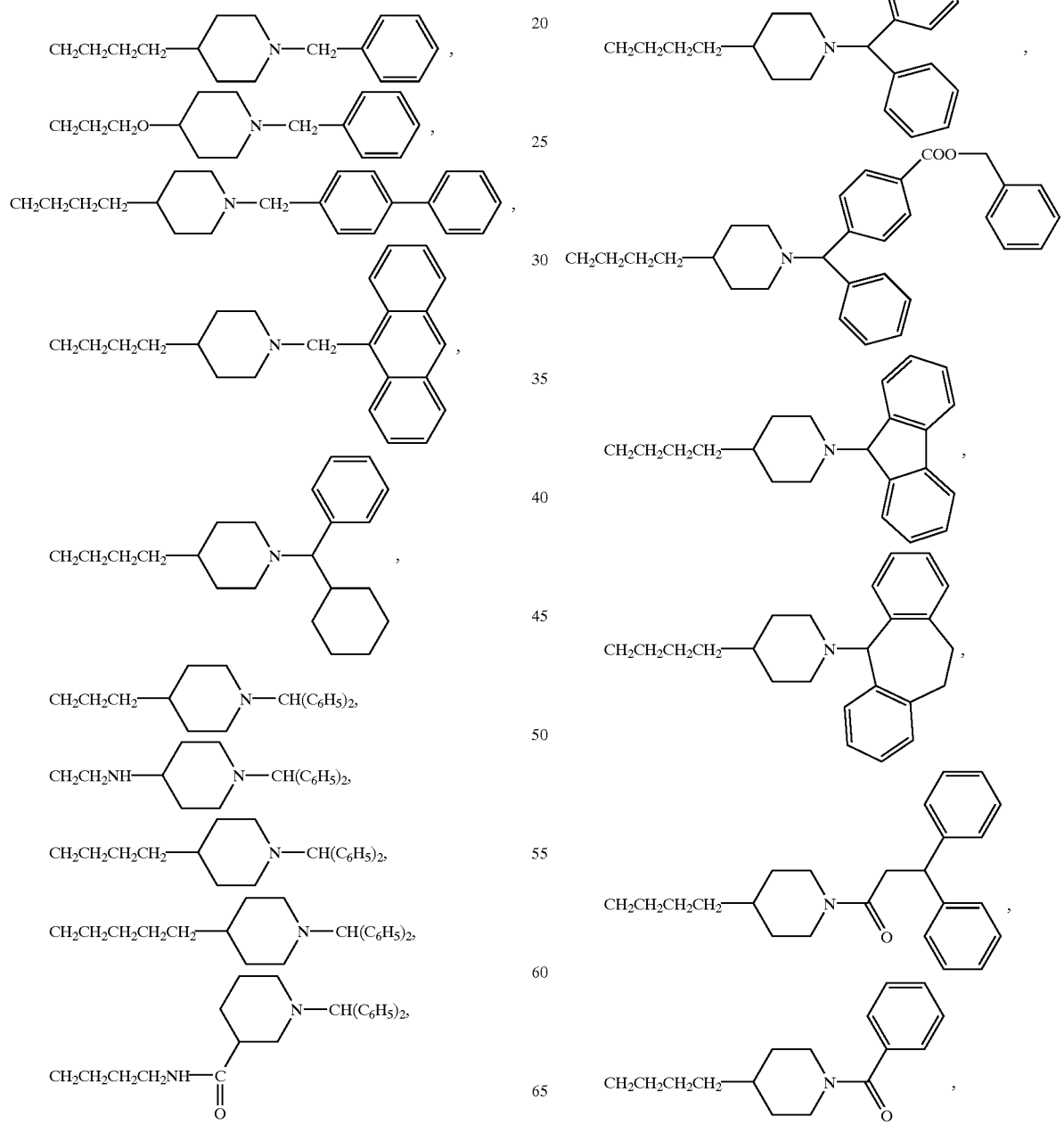

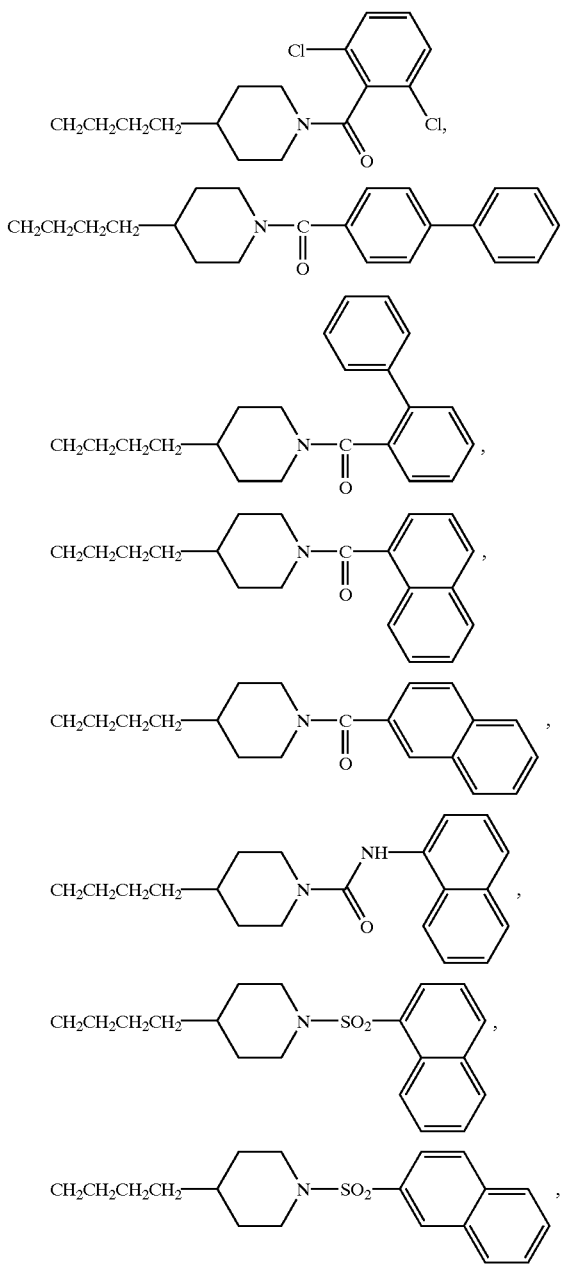

and

6. A method of inhibiting tumor cell growth in a human or animal body comprising administering an effective amount of a pharmaceutical composition, wherein the pharmaceutical composition includes a compound of general formula (I) and pharmaceutically acceptable salts of formula (I)

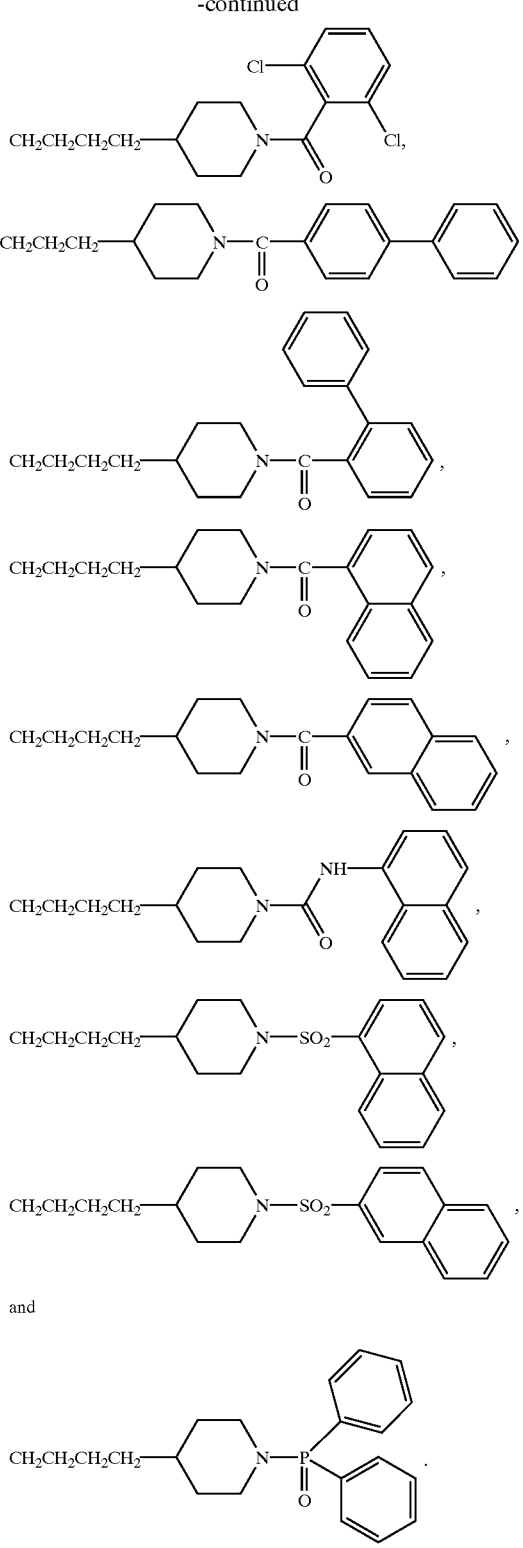

wherein
R¹ is selected from the group consisting of hydrogen, fluorine, methyl, trifluoromethyl and hydroxy,
R² and R³ are hydrogen,
R⁴ is hydrogen or hydroxy,
A is selected from the group consisting of ethylene, propylene, butylene, substituted ethylene substituted by hydroxy or one or two fluorine, substituted propylene substituted by hydroxy or one or two fluorine, and substituted butylene substituted by hydroxy or one or two fluorine,
D is selected from the group consisting of $C_2$–$C_6$-alkylene an E double bonded $C_2$–$C_6$-alkylene which has a double bond to ring E,
E is piperidine,
G is selected from the group consisting of benzyl, phenethyl, fluorenylmethyl, anthrylmethyl, diphenylmethyl, fluorenyl, dihydrodibenzocycloheptenyl, acetyl, pivaloyl, phenylacetyl, diphenylacetyl, diphenylpropionyl, naphthylacetyl, benzoyl, naphthoyl, anthrylcarbonyl, oxofluorenylcarbonyl, oxodihydroanthrylcarbonyl, dioxodihydroanthrylcarbonyl, naphthylaminocarbonyl, dibenzylaminocarbonyl, benzylphenylaminocarbonyl, diphenylaminocarbonyl, methanesulfonyl, phenylsulfonyl, p-toluolsulfonyl, naphthylsulfonyl, and diphenylphosphinoyl,
wherein aromatic rings in G may be substituted independently of each other by one to three substituents which are independently selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-alkoxy, benzyloxy, phenoxy, mercapto, $C_1$–$C_6$-alkylthio, carboxy, $C_1$–$C_6$-alkoxycarbonyl, benzyloxycarbonyl, nitro, amino, mono-$C_1$–$C_6$-alkylamino, di-($C_1$–$C_6$-alkyl)-amino, substituted $C_1$–$C_6$-alkoxy which is entirely or partially substituted by fluorine, wherein two adjacent groups in the ring in may form an additional ring over a methylenedioxy bridge.

7. A method of inhibiting tumor cell growth according to claim 6, wherein the composition is administered by a method selected from the group consisting of subcutaneously, intramuscularly, intravenously, intracutaneous, orally, sublingually, transdermally, topically and combinations thereof.

8. A method of inhibiting tumor cell growth according to claim 6, wherein the method is effective for inhibiting tumors selected from the group consisting of gynacological tumors, ovarian carcinomas, testicle tumors, esophagus carcinomas, stomach cancer, rectal carcinomas, pancreas carcinomas, thyroid cancer, adrenal tumors, leukemia, lymphomas, Hodgkin's disease, CNS tumors, soft-tissue sarcomas, bone sarcomas, benign and malignant mesotheliomas, intestine tumors, liver tumors, breast tumors, bronchial and, lung carcinomas, melanomas, benign papillomatosis tumors, and combinations thereof.

9. A method of inhibiting tumor cell growth according to claim 6, wherein the pharmaceutical composition is combined with a compound selected from the group consisting of pharmaceutically acceptable carriers, adjuvants, additives, and mixtures thereof.
10. A method of inhibiting tumor cell growth according to claim 6, wherein DEG is selected from the group consisting of
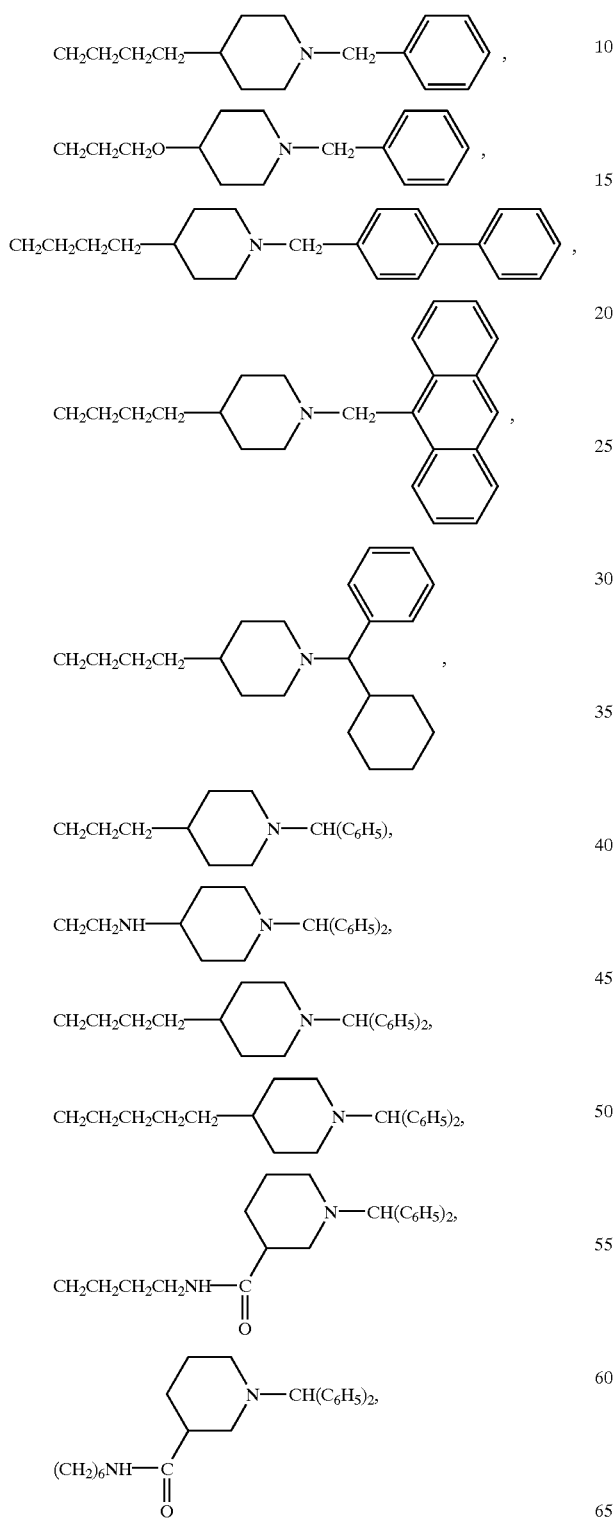
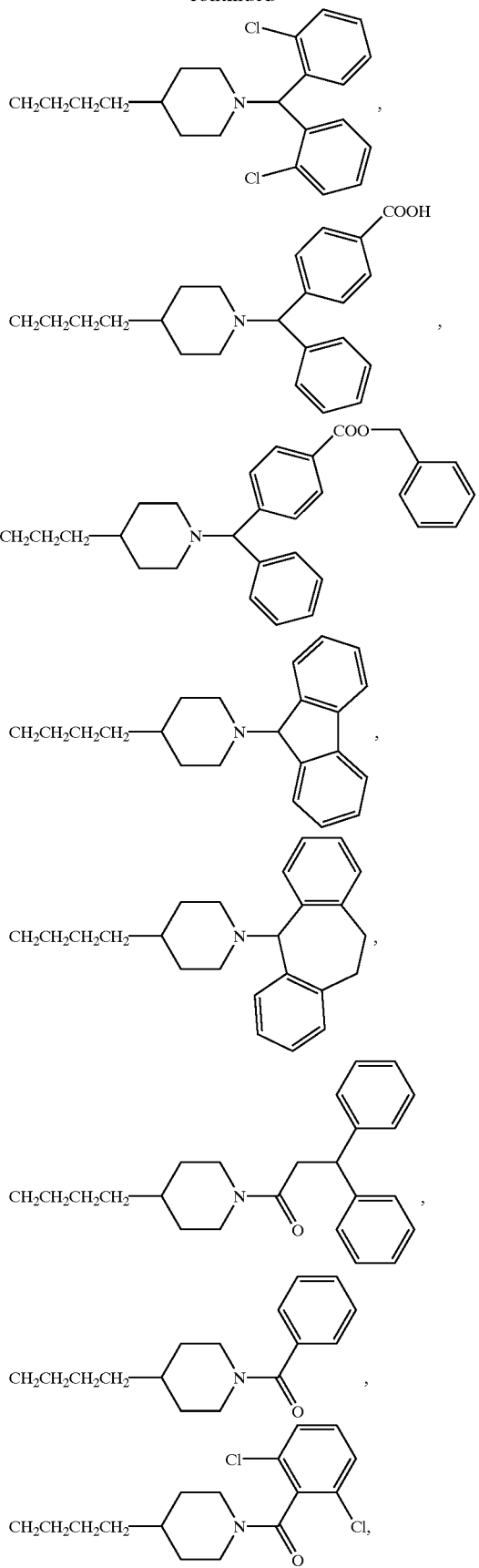

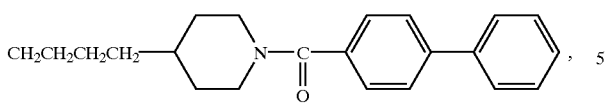

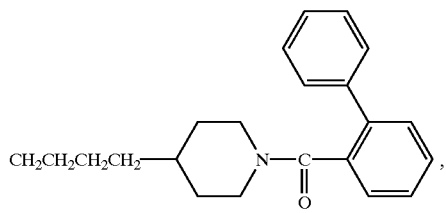

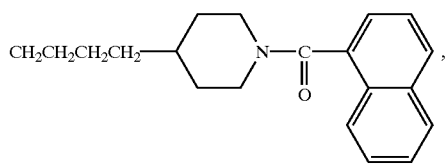

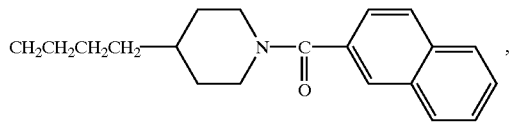

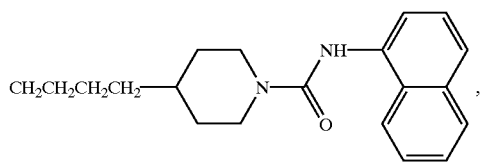

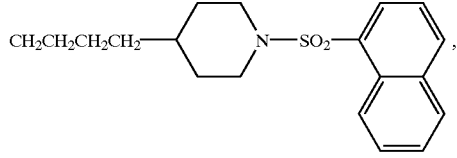

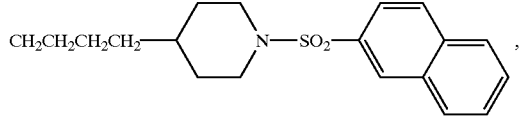

and

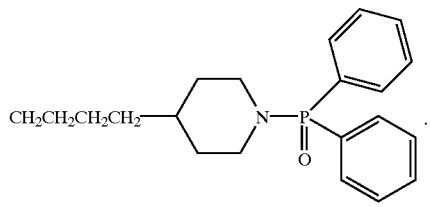

11. A method of suppressing autoimmune diseases in a human or animal body comprising administering to the human or animal body an effective amount of a pharmaceutical composition, wherein the pharmaceutical composition includes a compound of general formula (I) and pharmaceutically acceptable salts of formula (I)

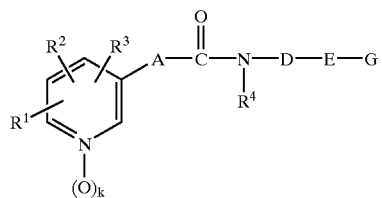

(I)

wherein $R^1$ is selected from the group consisting of hydrogen, halogen, cyano, $C_1$–$C_6$-alkyl, $C_3$–$C_6$-alkenyl, $C_3$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkylaminocarbonyl, $C_3$–$C_{13}$-dialkylaminocarbonyl, carboxy, phenyl, phenoxy, phenylthio, $NR^5R^6$, and bridged $R^1R^2$ wherein $R^5$ is selected from the group consisting of hydrogen, $C_1$–$C_6$-alkyl, $C_3$–$C_6$-alkenyl and $C_1$–$C_6$-alkinyl, $R^6$ is selected from the group consisting of hydrogen, $C_1$–$C_6$-alkyl, $C_3$–$C_6$-alkenyl and $C_3$–$C_6$-alkinyl, $R^2$ is selected from the group consisting of hydrogen, halogen, cyano, $C_1$–$C_6$-alkyl, trifluoromethyl, hydroxy, $C_1$–$C_6$-alkoxy, benzyloxy, $C_1$–$C_7$-alkanoyloxy, and bridged $R^1R^2$;

wherein bridged $R^1R^2$ is where $R^1R^2$ are adjacent and form a bridge which is selected from the group consisting of —$(CH_2)_4$— and —$(CH=CH)_2$— and —$CH_2O$—$CR^7R^8$—O—, wherein $R^7$ is selected from the group consisting of hydrogen and $C_1$–$C_6$-alkyl and $R^8$ is from the group consisting of hydrogen and $C_1$–$C_6$-alkyl, $R^3$ is selected from the group consisting of hydrogen, halogen, $C_1$–$C_6$-alkyl, trifluoromethyl and $C_1$–$C_6$-hydroxyalkyl;

$R^4$ is selected from the group consisting of hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy and benzyloxy;

k is 0 or 1,

A is selected from the group consisting of $C_1$–$C_6$-alkylene, a substituted $C_1$–$C_6$-alkylene which is substituted once to three-fold by $C_1$–$C_3$-alkyl, hydroxy, $C_1$–$C_3$-alkoxy, fluorine or phenyl, a 1,2-cyclopropylene and an isosterically substituted $C_2$–$C_6$-alkylene, which has a methylene unit which is isosterically replaced by O, S, $NR^9$, CO, SO or $SO_2$, wherein the isosteric replacement, with the exception of =CO, is not adjacent to the amide group, and wherein $R^9$ is selected from the group consisting of hydrogen, $C_1$–$C_6$-alkyl, $C_3$–$C_6$-alkenyl, $C_3$–$C_6$-alkinyl, $C_1$–$C_6$-acyl and $C_1$–$C_6$-alkylsulfonyl, D is selected from the group consisting of $C_1$–$C_{10}$-alkylene, a substituted $C_1$–$C_{10}$-alkylene which is substituted once or twice by $C_1$–$C_6$-alkyl, hydroxy, or $C_1$–$C_6$-alkoxy, a $C_2$–$C_{10}$-alkenylene, a substituted $C_2$–$C_{10}$-alkenylene which is substituted once or twice by $C_1$–$C_6$-alkyl, hydroxy, $C_1$–$C_6$-alkoxy, an E double bonded $C_2$–$C_{10}$-alkenylene which has a double bond to ring E, a $C_3$–$C_{10}$-alkinylene, a substituted $C_3$–$C_{10}$-alkinylene which is substituted once or twice by $C_1$–$C_6$-alkyl, hydroxy, or $C_1$–$C_6$-alkoxy, and an isoterically replaced group selected from the group consisting of $C_1$–$C_{10}$-alkylene, $C_2$–$C_{10}$-alkenylene or $C_3$–$C_{10}$-alkinylene, the isoterically replaced group having one to three methylene units are each isoterically replaced by O, S, $NR^{10}$, CO, SO or $SO_2$, wherein $R^{10}$ has the same meaning as $R^9$, but is selected independently therefrom, E is

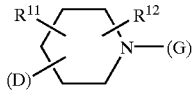

$R^{11}$ is selected from the group consisting of hydrogen, $C_1$–$C_6$-alkyl, hydroxy, hydroxymethyl, carboxy and $C_2$–$C_7$-alkoxycarbonyl, and $R^{12}$ is selected from the group consisting of hydrogen, $C_1$–$C_6$-alkyl and an oxo group adjacent to the nitrogen atom, or $R^{11}$ and $R^{12}$ together form a $C_1$–$C_3$-alkylene bridge under formation of a bi-cyclic ring system, G is selected from the group consisting of hydrogen, G1, G2, G3, G4 and G5, wherein G1 is

wherein r is an integer from 1 to 3 or 0, s is 0 or 1, $R^{13}$ is selected from the group consisting of hydrogen, $C_1$–$C_6$-alkyl, $C_3$–$C_6$-alkenyl, $C_3$–$C_6$-alkinyl, $C_3$–$C_8$-cycloalkyl, benzyl, phenyl, anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group, $R^{14}$ has the same meaning as $R^{13}$, but is selected independently thereof, $R^{15}$ is selected from the group consisting of hydrogen, hydroxy, methyl, benzyl, phenyl, anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group, G2 is selected from the group consisting of

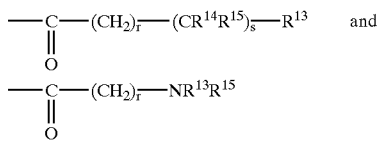

wherein the substituents $R^{13}$ and $R^{15}$ have the above meaning,

G3 is $-SO_2-(CH_2)_r R^{13}$ and

G4 is

wherein $Ar^1$ is selected from the group consisting of phenyl, and naphthyl, $Ar^2$ is selected from the group consisting of phenyl, and naphthyl, and G5 is $-COR^{16}$ wherein $R^{16}$ is selected from the group consisting of trifluoromethyl, $C_1$–$C_6$-alkoxy, $C_3$–$C_6$-alkenyloxy, and benzyloxy and wherein aromatic rings in the substituents $R^1$, $R^2$, $R^4$, $R^{13}$, $R^{14}$, $R^{15}$, $R^{16}$, $Ar^1$ and $Ar^2$ are substituted and unsubstituted the substituted rings in $R^1$, $R^2$, $R^4$, $R^{13}$, $R^{14}$, $R^{15}$, $R^{16}$, $Ar^1$ and $Ar^2$ having substitutents which are independently selected from halogen, cyano, $C_1$–$C_6$-alkyl, trifluoromethyl, $C_3$–$C_8$-cycloalkyl, phenyl, benzyl, hydroxy, $C_1$–$C_6$-alkoxy, and substituted $C_1$–$C_6$ alkoxy which is entirely or partially substituted by fluorine, benzyloxy, phenoxy, mercapto, $C_1$–$C_6$-alkylthio, carboxy, $C_1$–$C_6$-alkoxycarbonyl, benzyloxycarbonyl, nitro, amino, mono-$C_1$–$C_6$-alkylamino, and di-($C_1$–$C_6$-alkyl)-amino, wherein two adjacent groups on the aromatic ring may form an additional ring over a methylenedioxy bridge.

12. A method of suppressing autoimmune disease according to claim 11, wherein the composition is administered by a method selected from the group consisting of subcutaneously, intramuscularly, intravenously, intracutaneous, orally, sublingually, transdermally, topically and combinations thereof.

13. A method of suppressing autoimmune disease according claim 11, wherein the pharmaceutical composition is combined with a compound selected from the group consisting of pharmaceutically acceptable carriers, adjuvants, additives, and mixtures thereof.

14. A method of suppressing autoimmune disease according to claim 11 wherein DEG is selected from the group consisting of

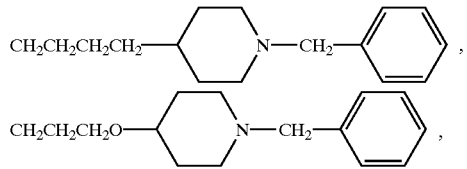

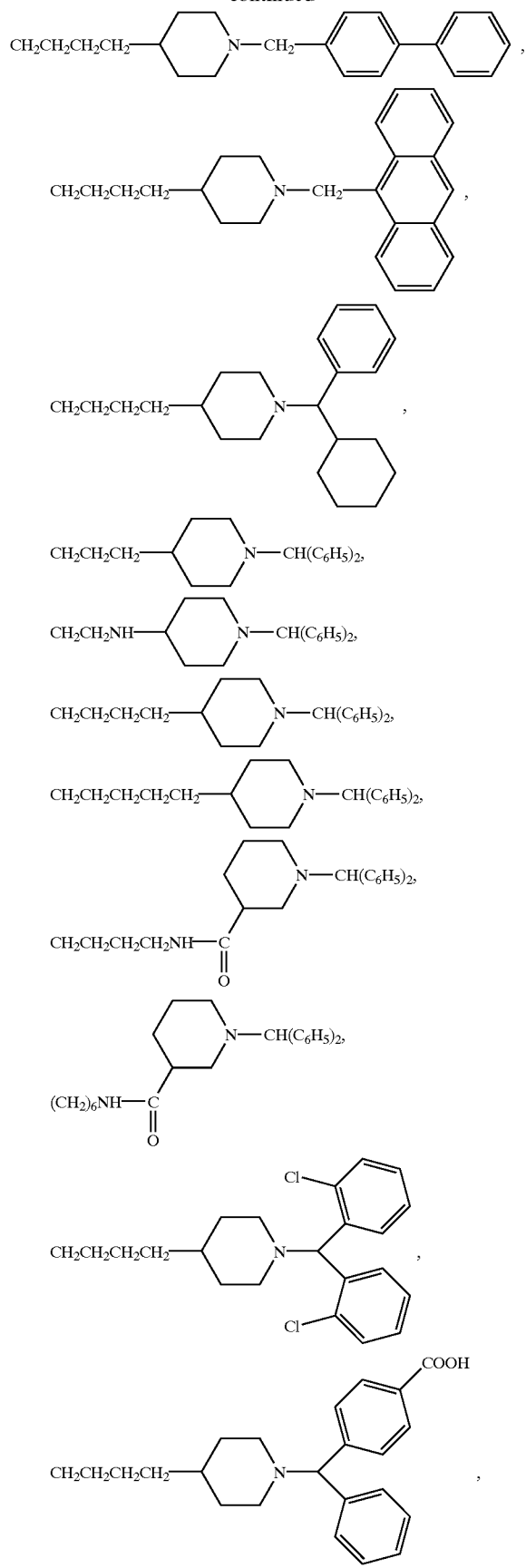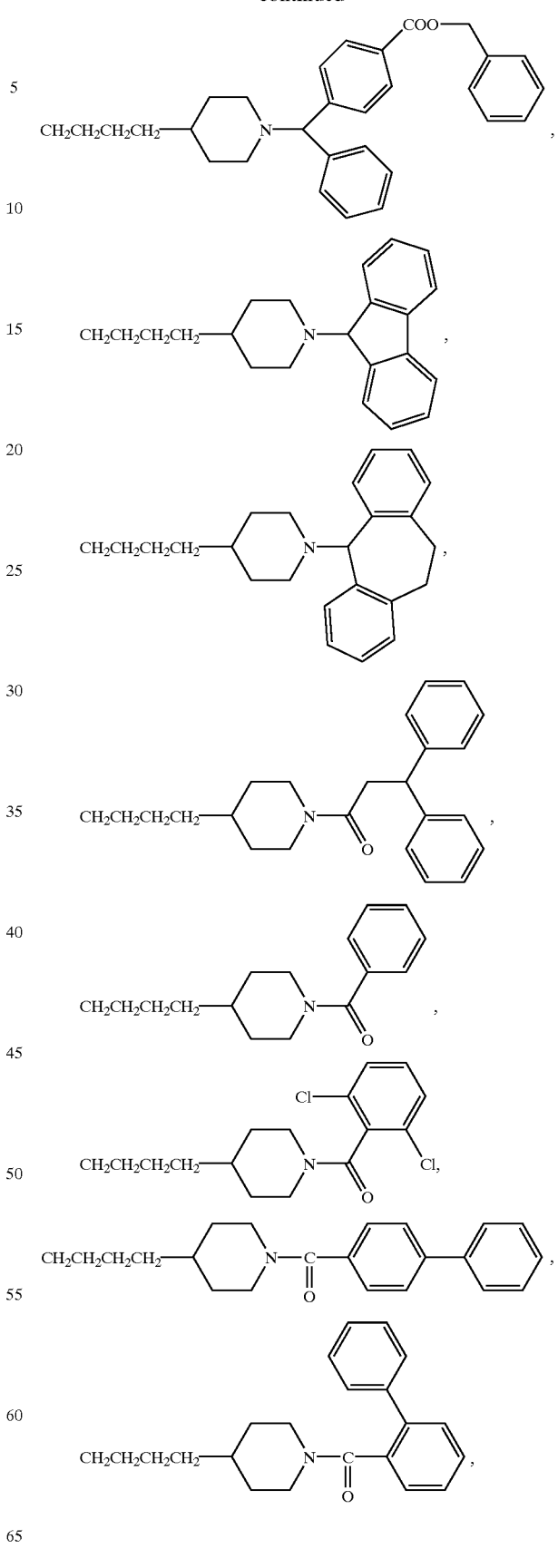

-continued

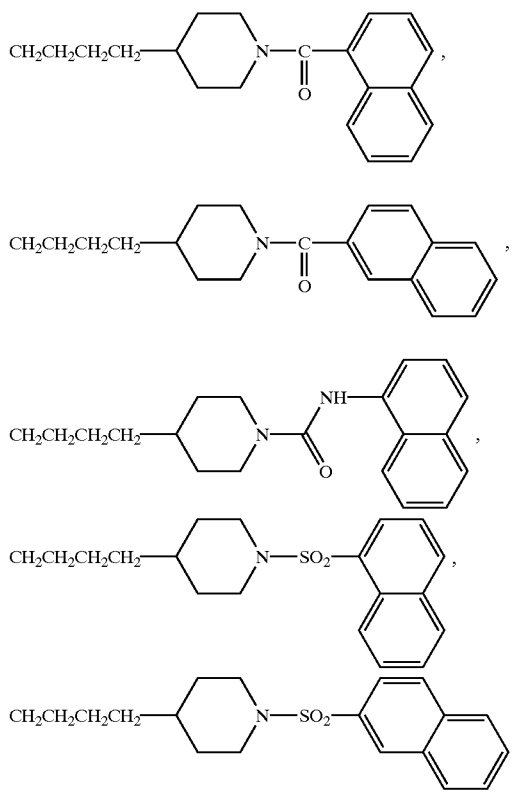

and

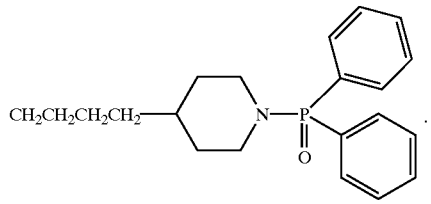

15. A method of suppressing autoimmune diseases in a human or animal body comprising administering to the human or animal body an effective amount of a pharmaceutical composition, wherein the pharmaceutical composition includes a compound of general formula (I) and pharmaceutically acceptable salts of formula (I)

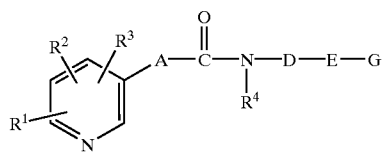

wherein
R$^1$ is selected from the group consisting of hydrogen, fluorine, methyl, trifluoromethyl and hydroxy,
R$^2$ and R$^3$ are hydrogen,
R$^4$ is hydrogen or hydroxy,
A is selected from the group consisting of ethylene, propylene, butylene, substituted ethylene substituted by hydroxy or one or two fluorine, substituted propylene substituted by hydroxy or one or two fluorine, and substituted butylene substituted by hydroxy or one or two fluorine, D is selected from the group consisting of $C_2$–$C_6$-alkylene and an E double bonded $C_2$–$C_6$-alkylene which has a double bond to ring E,
E is piperidine,
G is selected from the group consisting of benzyl, phenethyl, fluorenylmethyl, anthrylmethyl, diphenylmethyl, fluorenyl, dihydrodibenzocycloheptenyl, acetyl, pivaloyl, phenylacetyl, diphenylacetyl, diphenylpropionyl, naphthylacetyl, benzoyl, naphthoyl, anthrylcarbonyl, oxofluorenylcarbonyl, oxodihydroanthrylcarbonyl, dioxodihydroanthrylcarbonyl, naphthylaminocarbonyl, dibenzylaminocarbonyl, benzylphenylaminocarbonyl, diphenylaminocarbonyl, methanesulfonyl, phenylsulfonyl, p-toluolsulfonyl, naphthylsulfonyl, and diphenylphosphinoyl,
wherein aromatic rings in G may be substituted independently of each other by one to three substituents which are independently selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-alkoxy, substituted $C_1$–$C_6$-alkoxy which is entirely or partially substituted by fluorine, benzyloxy, phenoxy, mercapto, $C_1$–$C_6$-alkylthio, carboxy, $C_1$–$C_6$-alkoxycarbonyl, benzyloxycarbonyl, nitro, amino, mono-$C_1$–$C_6$-alkylamino and di-($C_1$–$C_6$-alkyl)-amino wherein two adjacent groups in the ring may form an additional ring over a methylenedioxy bridge.

16. A method of suppressing autoimmune disease according to claim 15, wherein the composition is administered by a method selected from the group consisting of subcutaneously, intramuscularly, intravenously, intracutaneous, orally, sublingually, transdermally, topically and combinations thereof.

17. A method of suppressing autoimmune disease according to claim 15, wherein the pharmaceutical composition is combined with a compound selected from the group consisting of pharmaceutically acceptable carriers, adjuvants, additives, and mixtures thereof.

18. A method of suppressing autoimmune disease according to claim 15 wherein DEG is selected from the group consisting of

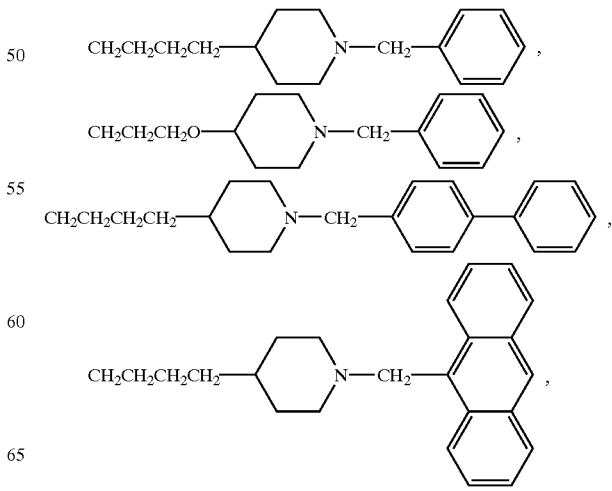

221
-continued
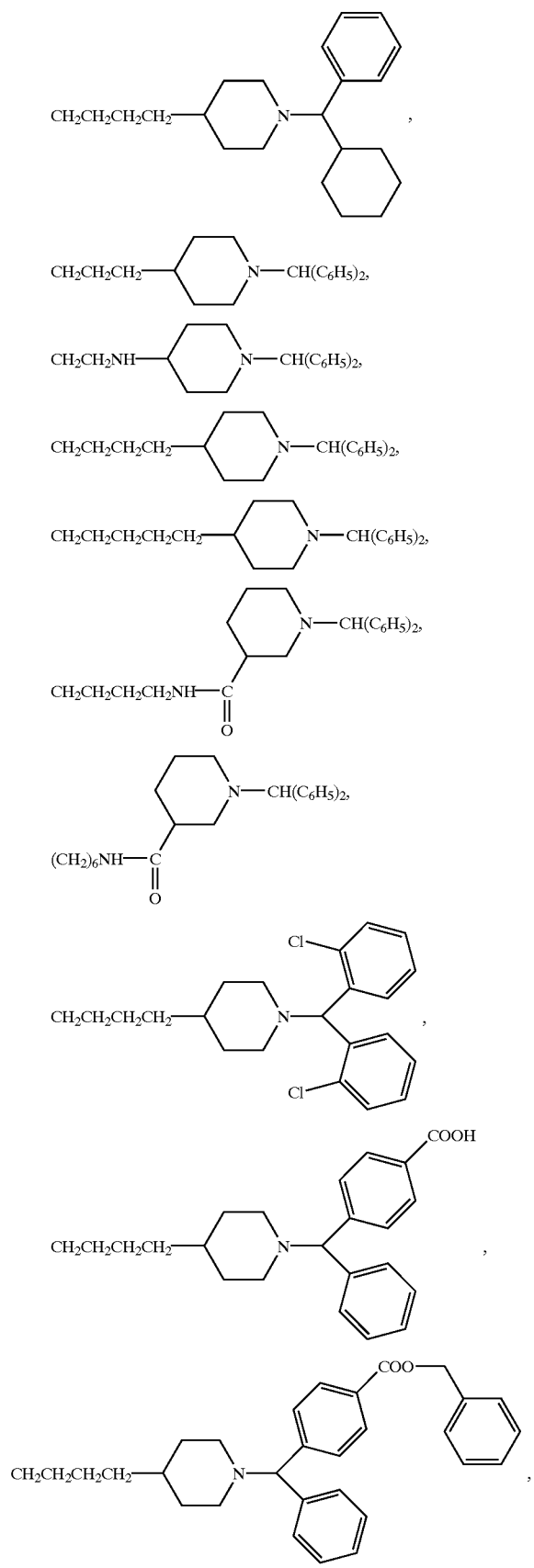
222
-continued
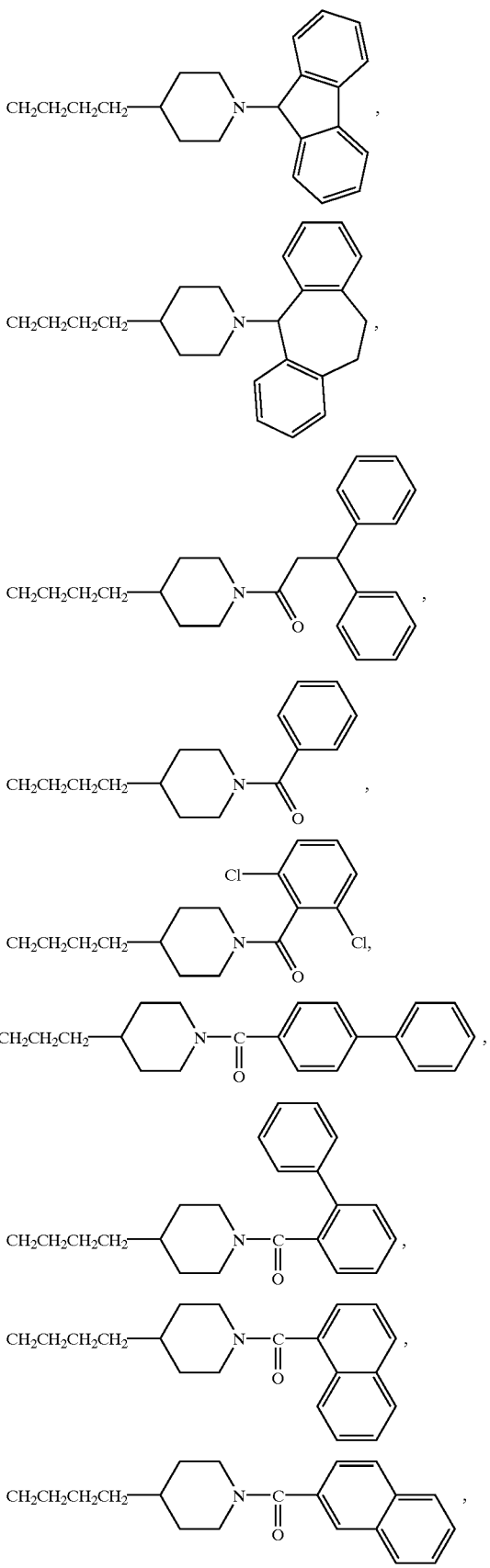

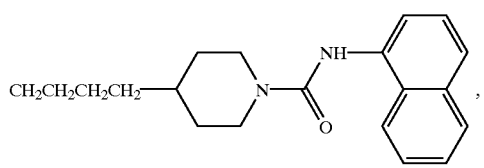
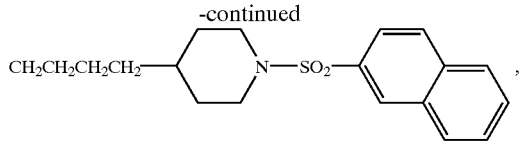
and
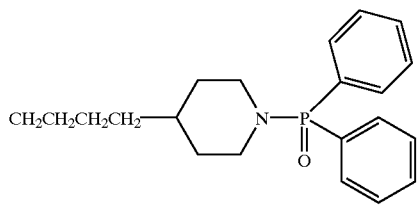
* * * * *